United States Patent
Xu et al.

(10) Patent No.: US 9,834,548 B2
(45) Date of Patent: Dec. 5, 2017

(54) PYRIDAZINE COMPOUNDS AS JAK INHIBITORS

(71) Applicant: Portola Pharmaceuticals, Inc., South San Francisco, CA (US)

(72) Inventors: Qing Xu, Foster City, CA (US); Yonghong Song, Foster City, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/118,433

(22) PCT Filed: Feb. 12, 2015

(86) PCT No.: PCT/US2015/015687
§ 371 (c)(1),
(2) Date: Aug. 11, 2016

(87) PCT Pub. No.: WO2015/123453
PCT Pub. Date: Aug. 20, 2015

(65) Prior Publication Data
US 2017/0174673 A1  Jun. 22, 2017

Related U.S. Application Data

(60) Provisional application No. 61/939,859, filed on Feb. 14, 2014.

(51) Int. Cl.
C07D 417/12 (2006.01)
C07D 237/24 (2006.01)
C07D 409/12 (2006.01)
C07D 401/12 (2006.01)
C07D 403/12 (2006.01)
C07D 401/14 (2006.01)
C07D 403/14 (2006.01)
C07D 409/14 (2006.01)
C07D 405/14 (2006.01)

(52) U.S. Cl.
CPC ......... *C07D 417/12* (2013.01); *C07D 237/24* (2013.01); *C07D 401/12* (2013.01); *C07D 401/14* (2013.01); *C07D 403/12* (2013.01); *C07D 403/14* (2013.01); *C07D 405/14* (2013.01); *C07D 409/12* (2013.01); *C07D 409/14* (2013.01)

(58) Field of Classification Search
CPC .. C07D 417/12; C07D 237/24; C07D 401/12; C07D 401/14; C07D 403/12; C07D 403/14; C07D 405/14; C07D 409/12; C07D 409/14
See application file for complete search history.

(56) References Cited

U.S. PATENT DOCUMENTS

| 6,797,706 | B1 | 9/2004 | Hisamichi et al. | |
|---|---|---|---|---|
| 7,576,072 | B2 | 8/2009 | Wallace et al. | |
| 8,138,339 | B2* | 3/2012 | Bauer | A61K 31/4985 540/601 |
| 2009/0318407 | A1* | 12/2009 | Bauer | A61K 31/4985 514/210.18 |
| 2012/0130073 | A1* | 5/2012 | Jia | C07D 239/48 544/296 |
| 2013/0178478 | A1 | 7/2013 | Hermann et al. | |
| 2013/0203763 | A1 | 8/2013 | Liang | |
| 2015/0284367 | A1* | 10/2015 | Bhagirath | C07D 213/72 514/252.03 |

FOREIGN PATENT DOCUMENTS

| WO | WO-2013/054351 A1 | 4/2013 |
|---|---|---|
| WO | WO-2014/060371 A1 | 4/2014 |
| WO | WO-2014/074661 A1 | 5/2014 |

OTHER PUBLICATIONS

International Search Report dated May 14, 2015 for International Application No. PCT/US2015/015687, filed Feb. 12, 2015, 3 pages.

* cited by examiner

*Primary Examiner* — Alexander R Pagano
(74) *Attorney, Agent, or Firm* — Mintz Levin Cohn Ferris Glovsky and Popeo, P.C.

(57) ABSTRACT

In one aspect, the invention provides a compound according to formula I, as well as tautomers, pharmaceutically acceptable salts, and hydrates thereof. Pharmaceutical compositions, methods of inhibiting Janus kinases (JAKs), and methods for treating a condition or disorder mediated at least in part by JAK kinase activity are also described.

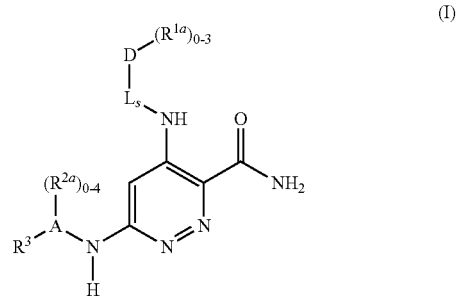

38 Claims, 9 Drawing Sheets

(I)

PYRIDAZINE COMPOUNDS AS JAK INHIBITORS

CROSS-REFERENCES TO RELATED APPLICATIONS

The present application is a national stage entry, filed under 35 U.S.C. §371, of International Application No. PCT/US2015/015687, filed on Feb. 12, 2015, which claims priority to U.S. Provisional Patent Application No. 61/939,859, filed on Feb. 14, 2014, the entirety of which applications are incorporated herein by reference.

BACKGROUND OF THE INVENTION

Field of the Invention

This invention is directed to pyridazine-3-carboxamide compounds which act as inhibitors of Janus kinases (JAKs). This invention is also directed to pharmaceutical compositions containing the pyridazine-3-carboxamide compounds and methods of using the compounds or compositions for the treatment of conditions in which modulation of the JAK pathway or inhibition of JAK kinases are therapeutically relevant such as inflammatory, autoimmune disorders, as well as cancer. The diseases or conditions involving inflammation or immune responses, such as rheumatoid arthritis, psoriasis, Crohn's disease, asthma, rhinitis, inflammatory bowel disease, colitis, transplant rejection, etc. The invention is also directed to methods of making the compounds described herein.

State of the Art

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, Alzheimer's disease and hormone-related diseases. As a consequence, there have been substantial efforts in medicinal chemistry to find inhibitors of protein kinases for use as therapeutic agents.

Janus kinases (or JAKs) are a family of cytoplasmic protein tyrosine kinases including JAK1, JAK2, JAK3 and tyrosine kinase 2 (TYK2). The JAKs play a crucial role in cytokine-dependent regulation of proliferation and function of cells involved in immune response. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal transducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important for lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes, rheumatoid arthritis, lupus, psoriasis), and inflammation (e.g., asthma, allergic reactions). Conditions which can benefit from JAK3 inhibition are discussed in greater detail below. Recent data on JAK inhibition has been reported in kidney allograft patients treated with CP-690,550 and showed that markers of allogeneic response (interferon gamma) can be reduced (Van Gurp E A et al (2009) Transplantation 87:79-86).

Various groups have implicated JAK-STAT signaling in chondrocyte biology Li et al. (*J Immunol*. 2001. 166:3491-3498) showed that Oncostatin M induces MMP and TIMP3 gene expression in primary chondrocytes by activation of JAK/STAT and MAPK signaling pathways. Osaki et al (*Biochem J*. 2003. 369:103-115) showed that interferon-gamma mediated inhibition of collagen II in chondrocytes involves JAK/STAT signaling. Therefore, these observations suggest a role for JAK kinase activity in cartilage hemostasis and therapeutic opportunities for JAK kinase inhibition in Osteoarthritis. Additionally JAK family has been linked to cancers, in particular leukemias e.g. acute myeloid leukemia, acute lymphoblastic leukemia or solid tumors e.g. uterine leiomyosracoma and prostate cancer (e.g., Constantinescu, et al. *Trends in Biochemical Sciences*. 2007. 33(3): 122-131). These results indicate inhibitors of JAK may also have utility in the treatment of cancers.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel compounds for use in the treatment of conditions in which targeting of the JAK pathway or inhibition of JAK kinases are therapeutically useful.

While progress has been made in this field, there remains a need in the art for compounds that inhibit JAK kinases, as well as for methods for treating conditions in a patient, such as rheumatoid arthritis, psoriasis, Crohn's disease, multiple sclerosis, asthma, acute myeloid leukemias (AML), solid tumors, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

In one aspect, the invention provides a compound according to formula I:

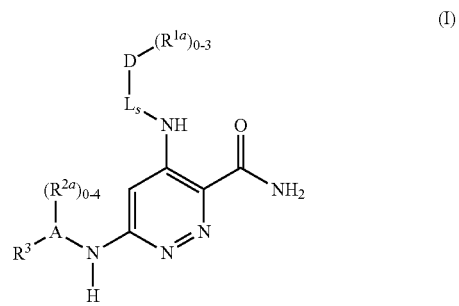

or a tautomer thereof or a pharmaceutically acceptable salt or hydrate thereof, wherein:
D is selected from $C_{1-8}$ alkyl, $C_{6-10}$ aryl, $C_{3-8}$ cycloalkyl, and 5- to 6-membered heteroaryl,
each $R^{1a}$ is independently selected from halo, hydroxy, cyano, $C_{1-8}$ alkyl, $C_{1-8}$ alkoxy, $C_{3-8}$ cycloalkyl, $C_{6-10}$ aryl, 5- to 6-membered heteroaryl, and 5- to 8-membered heterocyclyl, or two $R^{1a}$ moieties, together with the atoms to which they are attached, form a fused 5- to 6-membered ring;
L is selected from 5- to 6-membered heterocyclyl, —C(R)$_2$—, and —[C(R)$_2$]$_2$—, wherein each R is independently selected from H and $C_{1-4}$ alkyl;
the subscript s is 0 or 1;
A is selected from $C_{6-10}$ aryl and 5- to 6-membered heteroaryl,
each $R^{2a}$ is independently selected from halo, hydroxy, cyano, $C_{1-8}$ alkyl, $C_{1-8}$ alkoxy, $C_{6-10}$ aryl, and 5- to 6-membered heterocyclyl, or two $R^{2a}$ moieties, together with the atoms to which they are attached, form a fused 5- to 6-membered ring;
$R^3$ is selected from hydrogen, $C_{1-8}$ alkyl, $C_{1-8}$ haloalkyl, $C_{1-8}$ alkoxy, $R^{3a}$—(SO)—($R^{3b}$)$_t$—, $R^{3a}$—(SO)$_2$—($R^{3b}$)$_t$—, $R^{3c}$—(CO)—($R^{3d}$)$_t$—, ($C_{3-8}$ cycloalkyl)-($R^{3e}$)$_t$—, and (5- to 8-membered heterocyclyl)-($R^{3e}$)$_t$—; wherein
$R^{3a}$ is selected from OH, $C_{1-8}$ alkyl, and N(R$^0$)$_2$, wherein each R$^0$ is independently H or $C_{1-4}$ alkyl;
$R^{3b}$ is selected from $C_{1-8}$ alkylene, and —NR$^0$—, wherein R$^0$ is H or $C_{1-4}$ alkyl;
$R^{3c}$ is selected from $C_{1-8}$ alkyl, $C_{3-8}$ cycloalkyl, $C_{1-8}$ alkoxy, 5- to 8-membered heterocyclyl, and N(R$^0$)$_2$, wherein each R$^0$ is independently H or $C_{1-4}$ alkyl;
$R^{3d}$ is selected from $C_{1-8}$ alkylene, and —NR$^0$—, wherein R$^0$ is H or $C_{1-4}$ alkyl;
$R^{3e}$ is selected from $C_{1-8}$ alkylene, and $C_{1-8}$ heteroalkylene; and subscript t is 0 or 1;
and wherein each heteroaryl group and each heterocyclic group are substituted with from 0 to 3 moieties independently selected from halo, cyano, $C_{1-4}$ alkyl, ($C_{1-4}$ alkyl)-(CO)—, and (R$^4$)$_2$N—(CO)— wherein each R$^4$ is independently selected from H and $C_{1-4}$ alkyl.

In a related aspect, the invention provides a composition containing a compound of the invention in combination with a pharmaceutically acceptable carrier or diluent. The invention also provides a kit having a composition of the invention, packaging, and instructions for use.

In another aspect, the invention provides a method for inhibiting JAK kinase or a signal transduction pathway mediated at least in part by JAK kinase activity. The method includes the step of contacting a cell with a compound of the invention.

In another aspect, the invention provides a method for treating a condition or disorder mediated at least in part by JAK kinase activity in a subject. The method includes the step of administering to a subject in need of such treatment a therapeutically effective amount of a composition of the invention.

DETAILED DESCRIPTION OF THE INVENTION

I. Definitions

Figure 1:
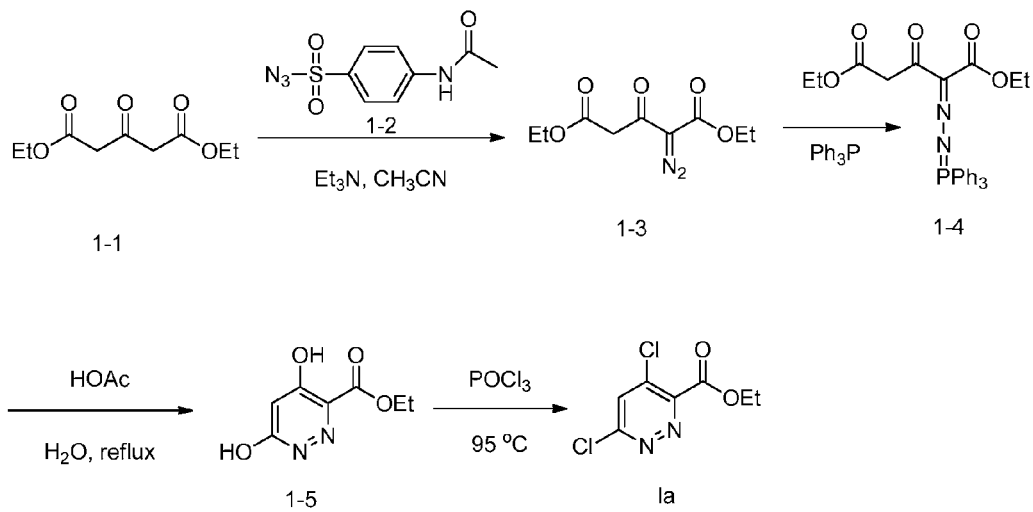
FIG. 1 shows a synthetic route for the preparation of a pyridazine intermediate compound.

It is noted here that as used in this specification and the appended claims, the singular forms "a," "an," and "the" include plural reference unless the context clearly dictates otherwise.

"Alkoxy" refers to —O(alkyl) where alkyl as defined herein. Representative examples of alkoxy groups include methoxy, ethoxy, t-butoxy, and the like.

"Alkyl," by itself or as part of another substituent, means, unless otherwise stated, a straight or branched chain, fully saturated aliphatic hydrocarbon radical having the number of carbon atoms designated. For example, "$C_{1-8}$ alkyl" refers to a hydrocarbon radical straight or branched, containing from 1 to 8 carbon atoms that is derived by the removal of one hydrogen atom from a single carbon atom of a parent alkane. Alkyl includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" refers to a linear monovalent hydrocarbon radical or a branched monovalent hydrocarbon radical having the number of carbon atoms indicated in the prefix and containing at least one double bond, but no more than three double bonds. For example, $C_{2-8}$ alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those hydrocarbon groups having one triple bond and one double bond. For example, $C_{2-8}$ alkynyl is meant to include ethynyl, propynyl and the like.

"Amino" refers to a monovalent radical —$NH_2$.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Aryl groups include aromatic ring(s) fused to non-aromatic cycloalkyl groups and where the point of attachment to the remainder of the molecule can be through any suitable ring atom of any ring. Thus the phrase includes, but is not limited to, groups such as phenyl, anthracenyl, naphthyl by way of example. Non-limiting examples of aryl groups include phenyl, 1-naphthyl, 2-naphthyl and 4-biphenyl.

"Bond" when used as an element in a Markush group means that the corresponding group does not exist, and the groups of both sides are directly linked.

"Cycloalkyl" refers to a saturated or partially saturated cyclic group of from 3 to 14 carbon atoms and no ring heteroatoms and having a single ring or multiple rings including fused, bridged, and spiro ring systems. The term "cycloalkyl" includes cycloalkenyl groups, a partially saturated cycloalkyl ring having at least one site of >C=C<ring unsaturation. Examples of cycloalkyl groups include, for instance, adamantyl, cyclopropyl, cyclobutyl, cyclopentyl, cyclooctyl, and cyclohexenyl. "$C_{u'-v'}$cycloalkyl" refers to cycloalkyl groups having u' to v' carbon atoms as ring members. "$C_{u'-v'}$cycloalkenyl" refers to cycloalkenyl groups having u' to v' carbon atoms as ring members.

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocyclyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" includes any ring having at least one planar resonance structure where 2n+2 pi electrons are delocalized about the ring. Non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two fused rings.

The term "heterocyclyl" or "heterocycloalkyl" refers to a cycloalkyl group containing at least one ring heteroatom and optionally one or more oxo substituents. As used herein, the term "heteroatom" is meant to include oxygen (O), nitrogen (N), and sulfur (S), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, piperidine, morpholine, piperazine, isoxazoline, pyrazoline, imidazoline, pyrrolidine, and the like.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "halo$C_{1-8}$alkyl" is meant to include difluoromethyl, trifluoromethyl, 2,2,2-trifluoroethyl, 4-chlorobutyl, 3-bromopropyl, and the like. The term "haloalkenyl", and "haloalkynyl" refers to alkenyl and alkynyl radicals having one or more halogen atoms. Additionally, term "haloalkoxy" refers to an alkoxy radical substituted with one or more halogen atoms. In one group of embodiments, the haloalkyl, haloalkenyl, haloalkynyl, and haloalkoxy groups have from one to 5 or from one to 3 halo atoms. Examples of haloalkoxy groups include difluoromethoxy and trifluoromethoxy. In one group of embodiments, the halo atoms of the haloalkenyl and haloalkynyl groups are attached to the aliphatic portions of these groups.

The terms "optional" or "optionally" as used throughout the specification means that the subsequently described event or circumstance may but need not occur, and that the description includes instances where the event or circumstance occurs and instances in which it does not. For example, "heteroaryl group optionally substituted with an alkyl group means that the alkyl may but need not be present, and the description includes situations where the heteroaryl group is substituted with an alkyl group and situations where the heteroaryl group is not substituted with the alkyl group.

The term "oxo" includes a mono —O⁻ or divalent =O oxygen atom.

In each of the above embodiments designating a number of atoms e.g. "$C_{1-8}$" is meant to include all possible embodiments that have one fewer atom. Non-limiting examples include $C_{1-4}$, $C_{1-5}$, $C_{1-6}$, $C_{1-7}$, $C_{2-8}$, $C_{2-7}$, $C_{3-8}$, $C_{3-7}$ and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science,* 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refer to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, masks, reduces or prevents the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

"Tautomer" refers to alternate forms of a molecule that differ in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

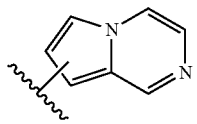

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2$H), tritium ($^3$H), iodine-125 ($^{125}$I) or carbon-14 ($^{14}$C). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an alkyl group that is substituted with alkoxy, "hydroxyalkyl" refers to an alkyl group that is substituted with hydroxyl, and (phenyl)C$_{1-8}$alkyl refers to an alkyl group that is substituted with phenyl. For these substituents, the point of attachment is at the alkyl group.

It is understood that the definitions and formulas provided herein are not intended to include impermissible substitution patterns (e.g., methyl substituted with 5 fluoro groups). Such impermissible substitution patterns are well known to the skilled artisan.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of JAK" and related terms and phrases refer to a condition or disorder associated with inappropriate, e.g., less than or greater than normal, activity of JAK and at least partially responsive to or affected by modulation of JAK (e.g., JAK antagonist or agonist results in some improvement in patient well-being in at least some patients). Inappropriate functional activity of JAK might arise as the result of expression of JAK in cells which normally do not express the receptor, greater than normal production of JAK, or slower than normal metabolic inactivation or elimination of JAK or its active metabolites, increased expression of JAK or degree of intracellular activation (leading to, e.g., inflammatory and immune-related disorders and conditions) or decreased expression of JAK. A condition or disorder associated with JAK may include a "JAK-mediated condition or disorder".

As used herein, the phrases "a condition or disorder mediated at least in part by JAK kinase activity", and related phrases and terms refer to a condition or disorder characterized by inappropriate, e.g., greater than normal, JAK activity. Inappropriate JAK functional activity might arise as the result of JAK expression in cells which normally do not express JAK or increased JAK expression or degree of intracellular activation (leading to, e.g., inflammatory and immune-related disorders and conditions). A condition or disorder mediated at least in part by JAK or JAK kinase activity may be completely or partially mediated by inappropriate JAK functional activity. However, a condition or disorder mediated at least in part by JAK kinase activity is one in which modulation of JAK results in some effect on the underlying condition or disorder (e.g., an JAK antagonist results in some improvement in patient well-being in at least some patients).

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The terms "modulate", "modulation" and the like refer to the ability of a compound to increase or decrease the function and/or expression of JAK, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with JAK, either directly or indirectly, and/or the up-regulation or down-regulation of the expression of JAK, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or down-regulate signal transduction. Activators or agonists are compounds that, e.g., bind to, stimulate, increase, open, activate, facilitate, enhance activation, activate, sensitize or up-regulate signal transduction. The ability of a compound to inhibit the function of JAK can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Subject" refers to human and non-human animals, especially mammals. Examples subjects include, but are not limited to, humans, cows, dogs, cats, goats, sheep, pigs and rabbits.

II. Pyridazine Compounds

In a first aspect, the invention provides a compound according to formula I:

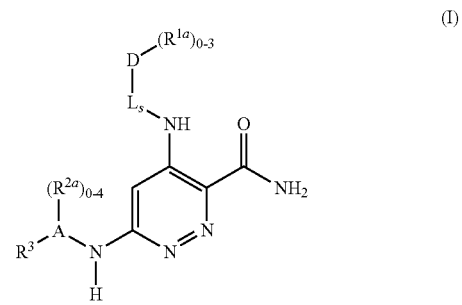

(I)

or a tautomer thereof or a pharmaceutically acceptable salt or hydrate thereof,
wherein:
D is selected from $C_{1-8}$ alkyl, $C_{6-10}$ aryl, $C_{3-8}$ cycloalkyl, and 5- to 6-membered heteroaryl,
each $R^{1a}$ is independently selected from halo, hydroxy, cyano, $C_{1-8}$ alkyl, $C_{1-8}$ alkoxy, $C_{3-8}$ cycloalkyl, $C_{6-10}$ aryl, 5- to 6-membered heteroaryl, and 5- to 8-membered heterocyclyl, or two $R^{1a}$ moieties, together with the atoms to which they are attached, form a fused 5- to 6-membered ring;
L is selected from 5- to 6-membered heterocyclyl, —C(R)$_2$—, and —[C(R)$_2$]$_2$—, wherein each R is independently selected from H and $C_{1-4}$ alkyl;
the subscript s is 0 or 1;
A is selected from $C_{6-10}$ aryl and 5- to 6-membered heteroaryl,
each $R^{2a}$ is independently selected from halo, hydroxy, cyano, $C_{1-8}$ alkyl, $C_{1-8}$ alkoxy, $C_{6-10}$ aryl, and 5- to 6-membered heterocyclyl, or two $R^{2a}$ moieties, together with the atoms to which they are attached, form a fused 5- to 6-membered ring;
$R^3$ is selected from hydrogen, $C_{1-8}$ alkyl, $C_{1-8}$ haloalkyl, $C_{1-8}$ alkoxy, $R^{3a}$—(SO)—($R^{3b}$)$_t$—, $R^{3a}$—(SO)$_2$—($R^{3b}$)$_t$—, $R^{3c}$—(CO)—($R^{3d}$)$_t$—, ($C_{3-8}$ cycloalkyl)-($R^{3e}$)$_t$—, and (5- to 8-membered heterocyclyl)-($R^{3e}$)$_t$—; wherein
$R^{3a}$ is selected from OH, $C_{1-8}$ alkyl, and N($R^0$)$_2$, wherein each $R^0$ is independently H or $C_{1-4}$ alkyl;
$R^{3b}$ is selected from $C_{1-8}$ alkylene, and —NR$^0$—, wherein $R^0$ is H or $C_{1-4}$ alkyl;
$R^{3c}$ is selected from $C_{1-8}$ alkyl, $C_{3-8}$ cycloalkyl, $C_{1-8}$ alkoxy, 5- to 8-membered heterocyclyl, and N($R^0$)$_2$, wherein each $R^0$ is independently H or $C_{1-4}$ alkyl;
$R^{3d}$ is selected from $C_{1-8}$ alkylene, and —NR$^0$—, wherein $R^0$ is H or $C_{1-4}$ alkyl;
$R^{3e}$ is selected from $C_{1-8}$ alkylene, and $C_{1-8}$ heteroalkylene; and
the subscript t is 0 or 1;
and wherein each heteroaryl group and each heterocyclic group are substituted with from 0 to 3 moieties independently selected from halo, cyano, $C_{1-4}$ alkyl, $(C_{1-4}$ alkyl)-(CO)—, and $(R^4)_2N$—(CO)— wherein each $R^4$ is independently selected from H and $C_{1-4}$ alkyl.

In one group of embodiments, A is $C_{6-10}$ aryl. In one group of embodiments, A is phenyl.

In one group of embodiments, A is 5- to 6-membered heteroaryl. In one group of embodiments, A is selected from pyrazinyl, pyrazolyl, pyridinyl, and thiazolyl.

In one group of embodiments, each $R^{2a}$ is independently selected from halo, $C_{1-8}$ alkyl, and $C_{1-8}$ alkoxy, or two $R^{2a}$ moieties, together with the atoms to which they are attached, form a fused 5- to 6-membered ring.

In one group of embodiments, D is $C_{1-8}$ alkyl. In one group of embodiments, D is selected from methyl and isopropyl. In one group of embodiments, D is $C_{6-10}$ aryl which is substituted with from 0 to 3 $R^{1a}$. In one group of embodiments, D is phenyl. In one group of embodiments, D is $C_{3-8}$ cycloalkyl. In one group of embodiments, D is selected from cyclobutyl, cyclopentyl, and cyclohexyl.

In one group of embodiments, D is 5- to 6-membered heteroaryl. For example, D can be:

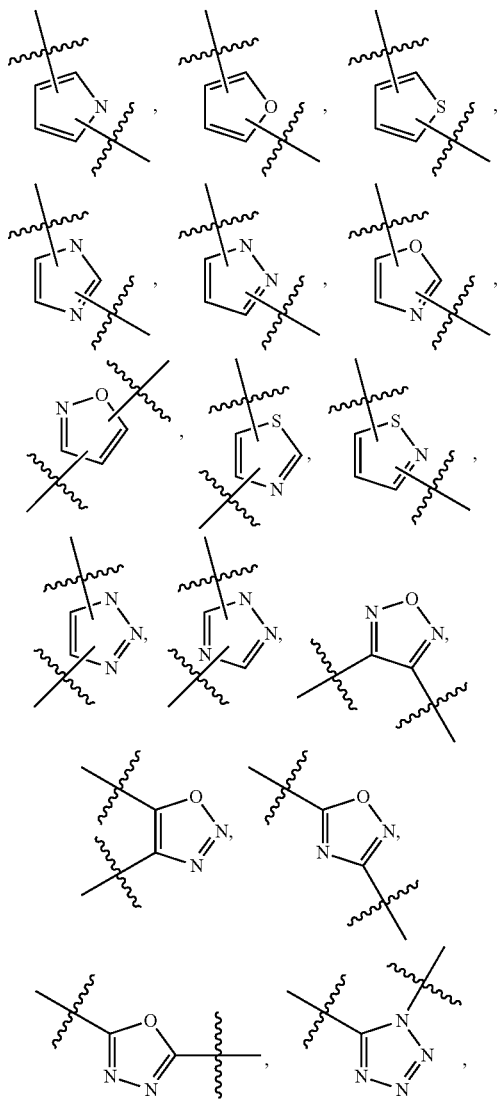

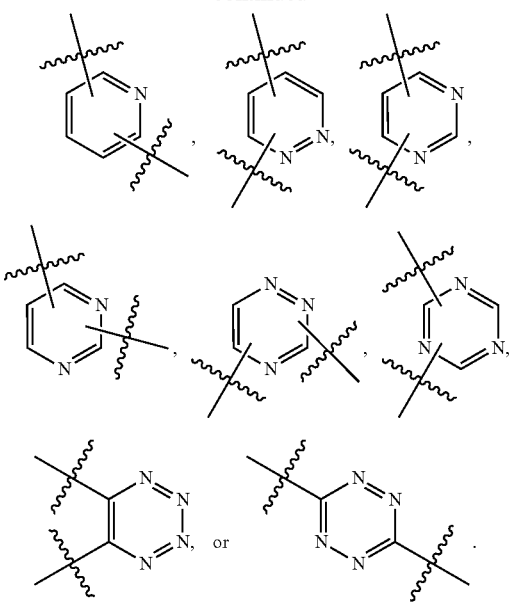

For the radicals described herein, a bond overlapping a ring is intended to show that the bond can be connected to the ring at any point where the valency of a ring atom will allow. Heteroatoms depicted with "open" sites are intended to show that the heteroatom can serve as the point of connection for the radical; alternatively, the heteroatom can be substituted with hydrogen as necessary to fill the valency requirements of the heteroatom. For example, a pyrazolyl radical depicted as:

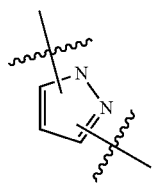

is intended to show that the radical can be connected as:

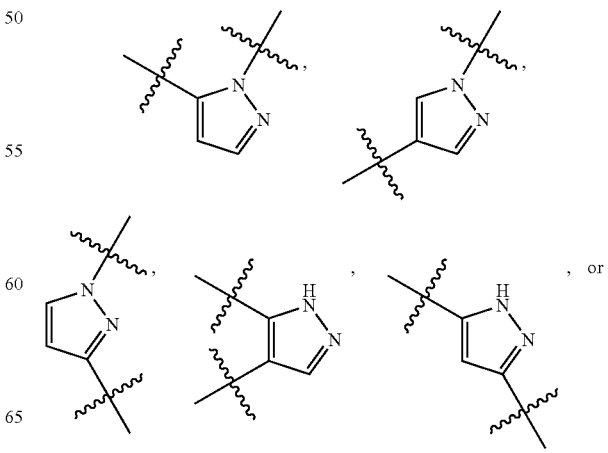

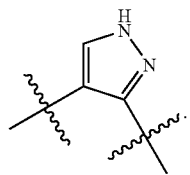
In certain embodiments, D is selected from:
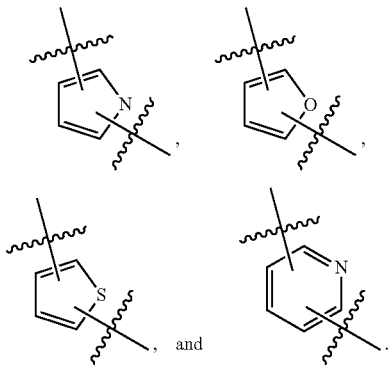
In one group of embodiments, D is selected from pyridinyl and thiophenyl.
In certain embodiments, each $R^{1a}$ is independently selected from cyano, chloro, fluoro, methyl, and methoxy.
In certain embodiments, each $R^{1a}$ is 5- to 6-membered heteroaryl or 5- to 8-membered heterocyclyl. For example, each $R^{1a}$ can independently be:
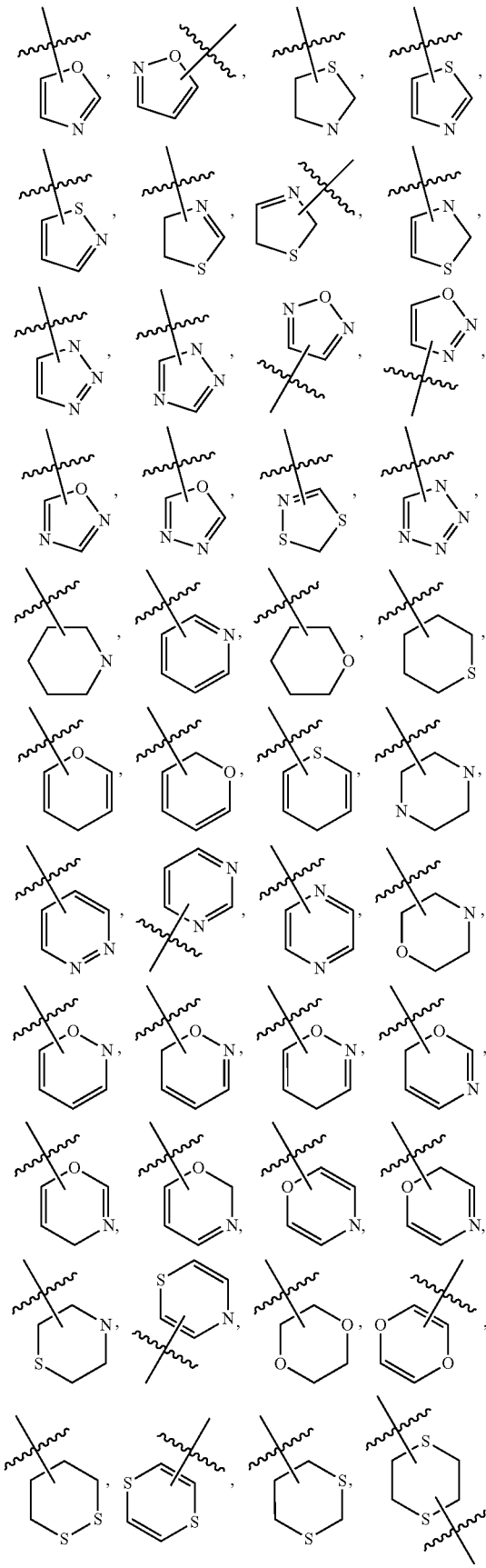

-continued

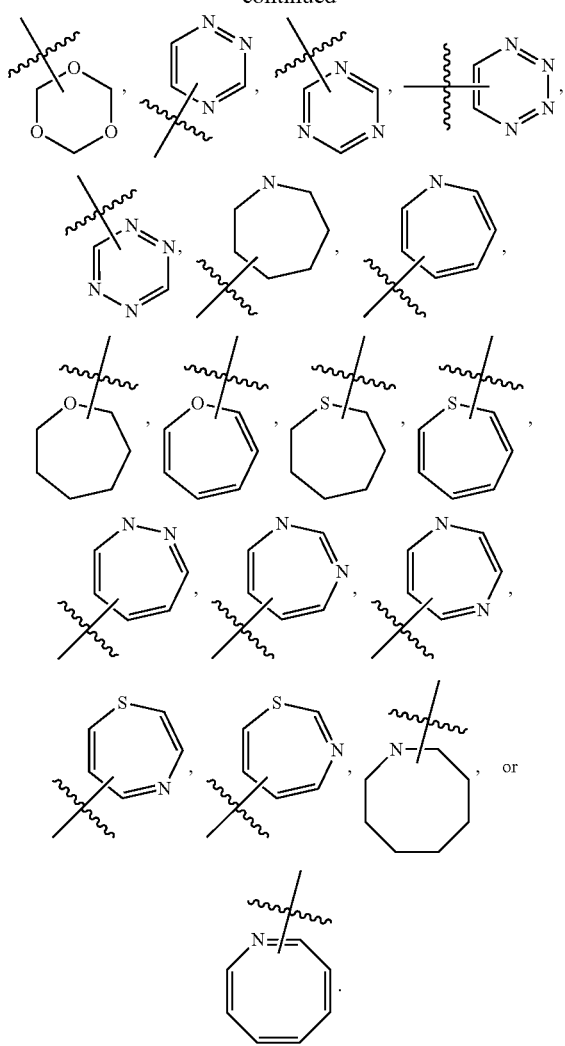

In certain embodiments, each $R^{1a}$ is independently selected from the group consisting of:

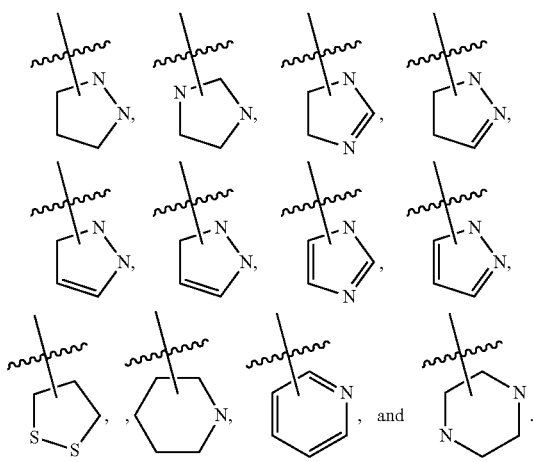

In certain embodiments, $R^{1a}$ is independently selected from imidazolyl and pyridinyl.

In certain embodiments, two $R^{1a}$ moieties, together with the atoms to which they are attached, form a fused 5- to 6-membered ring. For example, the moiety —D—$(R^{1a})_2$ can be:

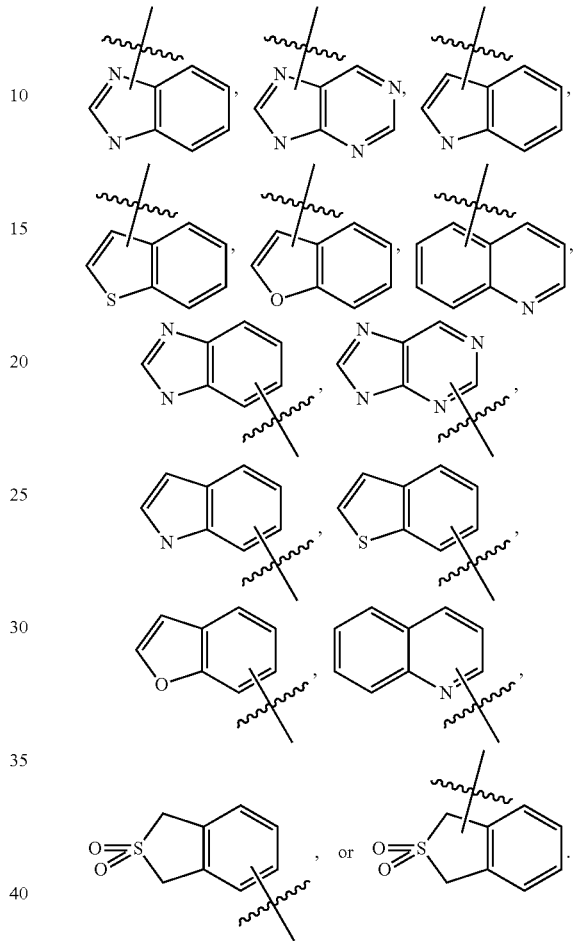

In one group of embodiments, each $R^{1a}$ is independently selected from cyano, chloro, fluoro, methyl, methoxy, imidazolyl, and pyridinyl, or two $R^{1a}$ moieties, together with the atoms to which they are attached, form a fused 5- to 6-membered ring.

In certain embodiments, $R^3$ is selected from $C_{1-8}$ alkyl, $C_{1-8}$ haloalkyl, and $C_{1-8}$ alkoxy.

In certain embodiments, $R^3$ is selected from $R^{3a}$—(SO)—$(R^{3b})_t$— and $R^{3a}$—$(SO)_2$—$(R^{3b})_t$—. In such embodiments, $R^{3a}$ is selected from OH, $C_{1-8}$ alkyl, and $N(R^0)_2$; the subscript t is 0 or 1; and $R^{3b}$ is selected from the group consisting of $C_{1-8}$ alkylene, and —$NR^0$—. In such embodiments, $R^0$ is H or $C_{1-4}$ alkyl In certain embodiments, $R^3$ is $R^{3c}$—(CO)—$(R^{3d})_t$—. In such embodiments, $R^{3c}$ is selected from the group consisting of $C_{1-8}$ alkyl, $C_{3-8}$ cycloalkyl, $C_{1-8}$ alkoxy, 5- to 8-membered heterocyclyl, and $N(R^0)_2$. In such embodiments, the subscript t is 0 or 1 and $R^{3d}$ is selected from $C_{1-8}$ alkylene and —$NR^0$—. In such embodiments, $R^0$ is H or $C_{1-4}$ alkyl.

In certain embodiments, $R^3$ is selected from ($C_{3-8}$ cycloalkyl)-$(R^{3e})_t$— and (5- to 8-membered heterocyclyl)-$(R^{3e})_t$—. In such embodiments, the subscript t is 0 or 1 and $R^{3e}$ is selected from $C_{1-8}$ alkylene, and $C_{1-8}$ heteroalkylene.

In one group of embodiments, $R^3$ is selected from $C_{1-8}$ alkyl, $C_{1-8}$ haloalkyl, and $C_{1-8}$ alkoxy. In one group of embodiments, $R^3$ is selected from $R^{3a}$—(SO)—$(R^{3b})_t$—, $R^{3a}$—(SO)$_2$—$(R^{3b})_t$—, and $R^{3c}$—(CO)—$(R^{3d})_t$—. In one group of embodiments, $R^3$ is selected from $(C_{3-8}$ cycloalkyl$)$-$(R^{3e})_t$— and (5- to 8-membered heterocyclyl)-$(R^{3e})_t$—.

In one group of embodiments, $R^3$ is selected from:

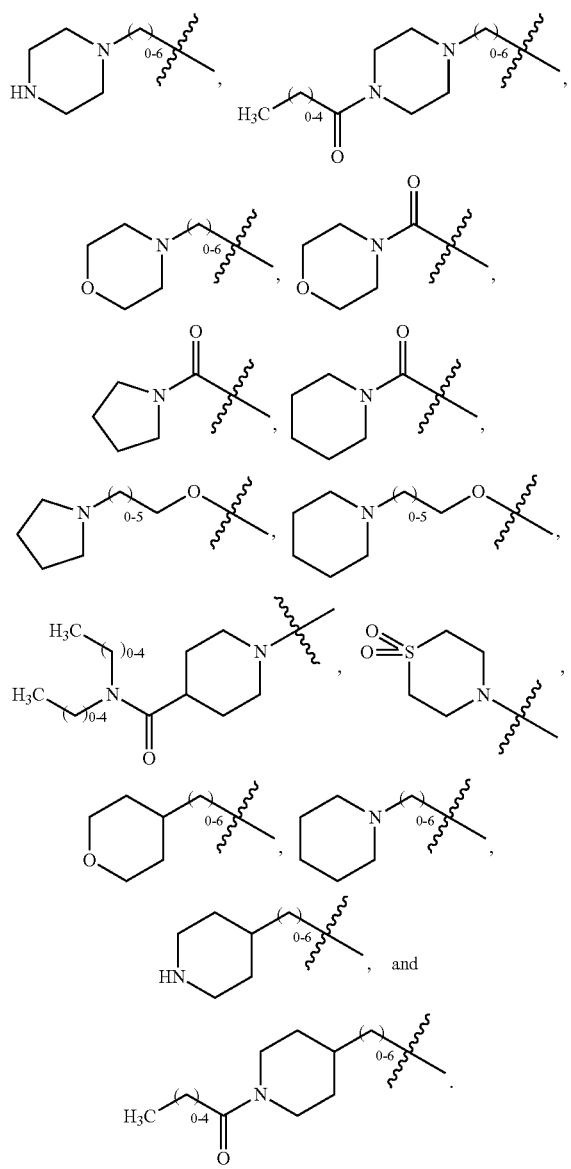

In one group of embodiments, $R^3$ is selected from:

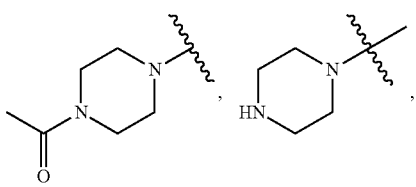

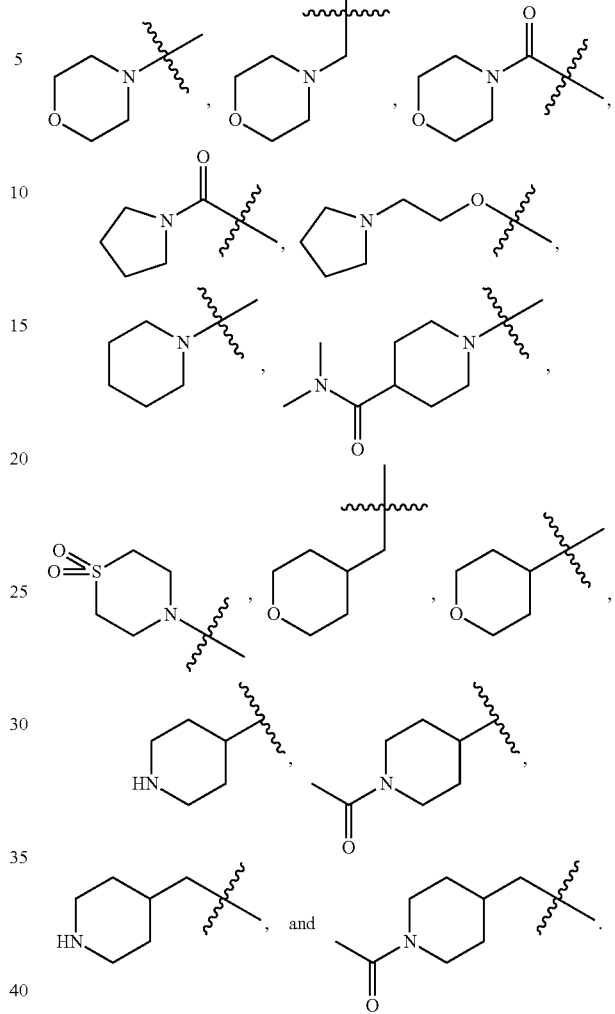

In one group of embodiments, the subscript s is 0. In one group of embodiments, the subscript s is 1 and L is selected from —C(R)$_2$— and —[C(R)$_2$]$_2$—. In one group of embodiments, the subscript s is 1 and L is —CH$_2$—.

In one group of embodiments, L is 5- to 6-membered heterocyclyl. In certain embodiments, L is selected from:

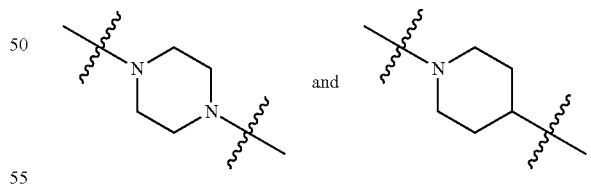

In one group of embodiments, A is 5- to 6-membered heteroaryl. For example, A can be:

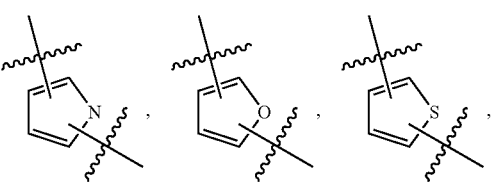

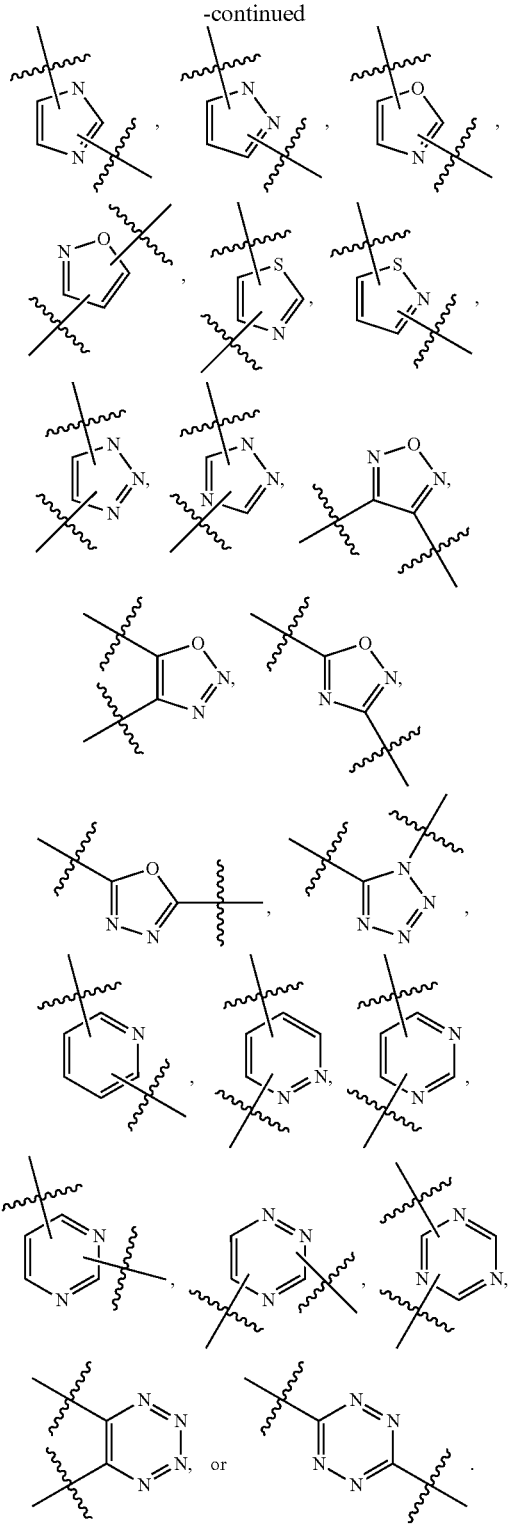

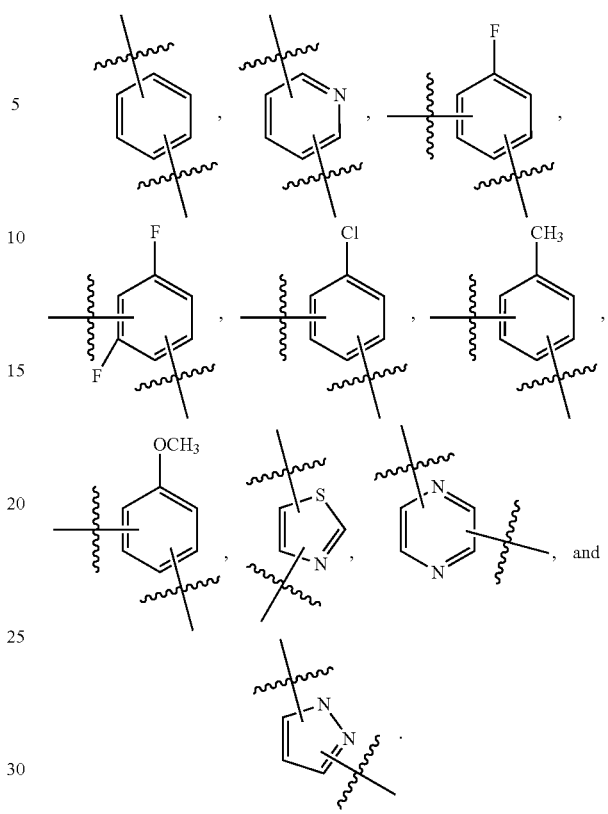

In such embodiments, A can be substituted with from 0 to 2 $R^{2a}$, and each $R^{2a}$ is independently selected from halo, $C_{1-4}$ alkyl, and $C_{1-4}$ alkoxy; or two $R^{2a}$ moieties, together with the carbon atoms to which they are attached, form a fused 5- to 6-membered ring.

In certain embodiments, the moiety —A($R^{2a}$)$_{0-4}$— is selected from:

In one group of embodiments, A is phenyl which is substituted with from 0 to 2 $R^{2a}$, and each $R^{2a}$ is independently selected from halo, $C_{1-4}$ alkyl, and $C_{1-4}$ alkoxy; or two $R^{2a}$ moieties, together with the carbon atoms to which they are attached, form a fused 5- to 6-membered ring.

In one group of embodiments, D is selected from methyl, ethyl, n-propyl, isopropyl, n-butyl, tert-butyl, sec-butyl, cyclobutyl, cyclopentyl, cyclohexyl, phenyl, pyridinyl, and thiophenyl, each of which is substituted with from 0 to 2 $R^{1a}$, wherein each $R^{1a}$ is independently selected from halo, hydroxy, cyano, $C_{1-8}$ alkyl, $C_{1-8}$ alkoxy, $C_{3-8}$ cycloalkyl, $C_{6-10}$ aryl, 5- to 6-membered heteroaryl, and 5- to 8-membered heterocyclyl, or two $R^{1a}$ moieties, together with the atoms to which they are attached, form a fused 5- to 6-membered ring.

In one group of embodiments, $R^3$ is selected from acetamido; (N-methylacetamido); dimethylcarbamoyl; N-methylcyclopropanecarboxamido; (N-methyl)methoxycarboxamido; (methylsulfonyl)methyl; (methylsulfinyl)methyl; (morpholino)methyl; methylsulfonyl; 1-(methylsulfonyl)ethyl; 1-methyl-1-(methylsulfonyl)ethyl; 2-(methylsulfonyl)ethyl; (methylsulfonyl)methylamino; morpholino; 4-acetylpiperazin-1-yl; piperazin-1-yl; 4-propionylpiperazin-1-yl; 4-(dimethylcarbamoyl)piperidin-1-yl; 1-propionylpiperidin-4-yl; 1,1-dioxidothiomorpholino; morpholine-4-carbonyl; pyrrolidine-1-carbonyl; and 2-(pyrrolidin-1-yl)ethoxy.

In one group of embodiments, A is phenyl with 0 $R^{2a}$ moieties.

In one group of embodiments, A is selected from pyrazolyl, pyridinyl, and thiazolyl.

In one group of embodiments, D is selected from phenyl, pyridinyl, and piperidinyl, each of which is substituted with from 0 to 2 $R^{1a}$, wherein each $R^{1a}$ is independently selected from halo, cyano, 5- to 6-membered heteroaryl, and 5- to 6-membered heterocyclyl, or two $R^{1a}$ moieties, together with the atoms to which they are attached, form a fused 5- to 6-membered ring.

In one group of embodiments, $R^3$ is selected from hydrogen; methyl; ethyl; isopropyl; cyclopentyl; cyclopropylmethyl; 2-(dimethylamino)-2-oxoethyl; (tetrahydro-2H-pyran-4-yl)methyl; 1-(dimethylcarbamoyl)piperidin-4-yl)methyl; morpholino; morpholine-4-carbonyl; pyrrolidone-1-carbonyl; 1-propionylpiperidin-4-yl; piperazin-1-yl; and 4-acetylpiperazin-1-yl.

In one group of embodiments, the compound is selected from:

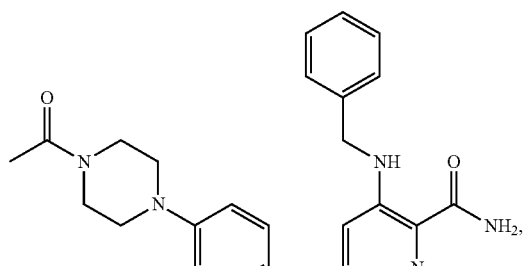

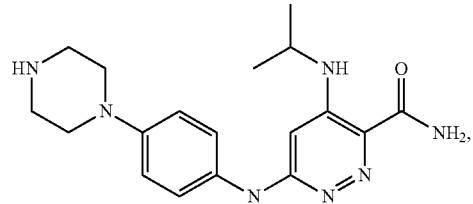

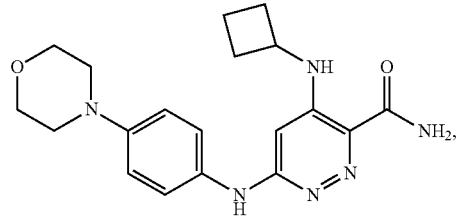

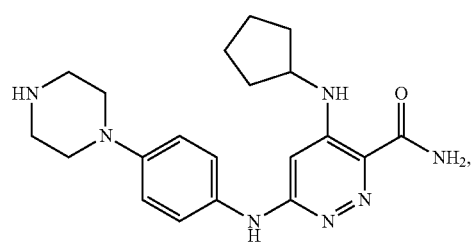

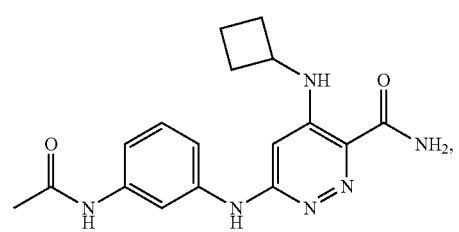

-continued

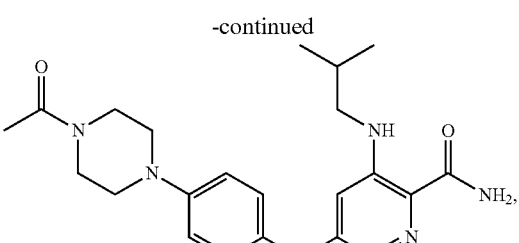

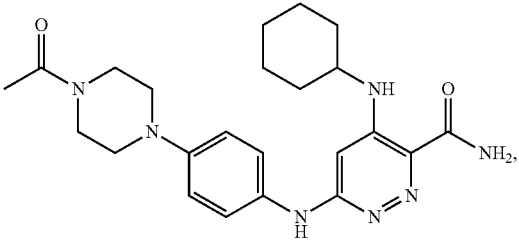

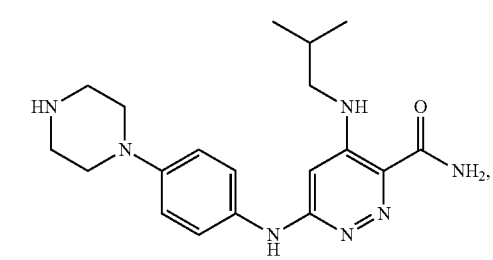

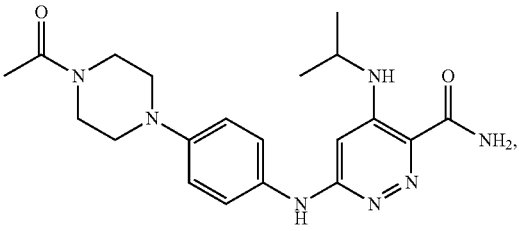

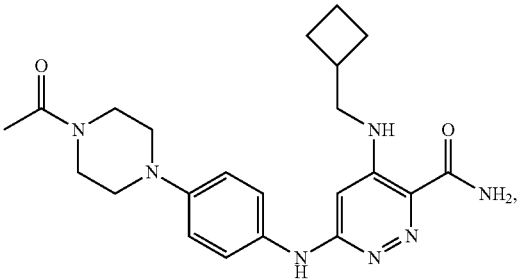

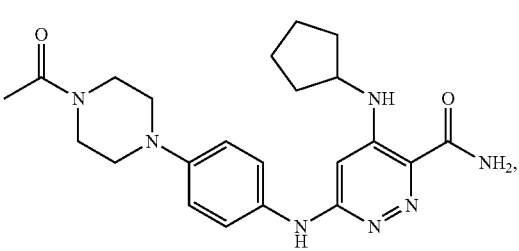

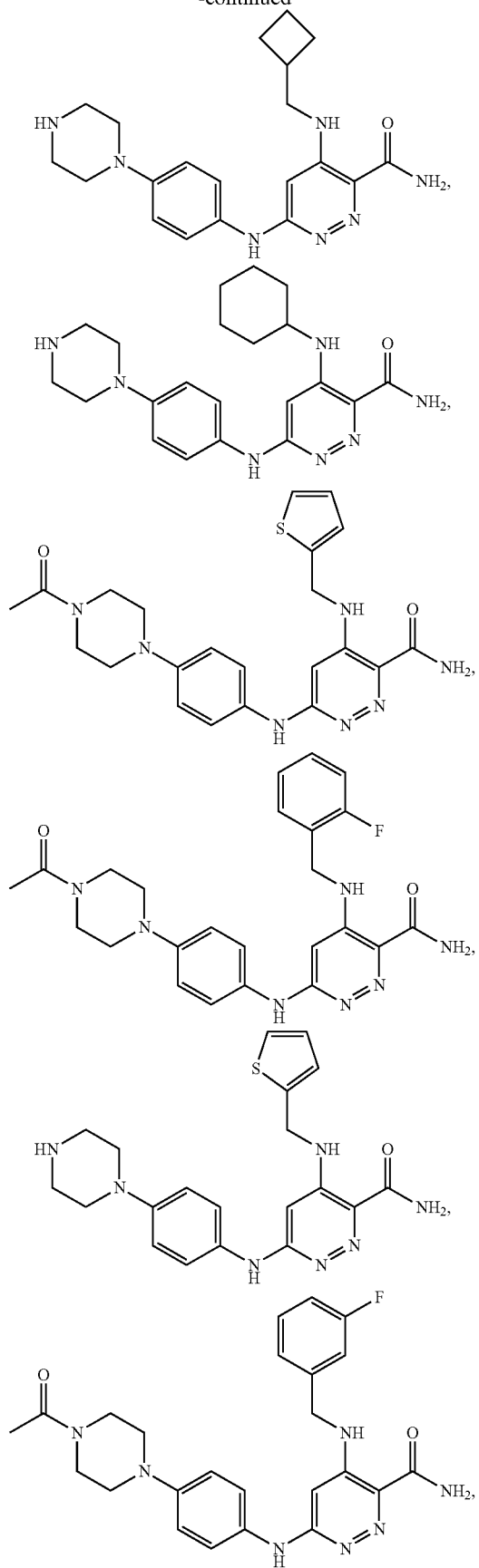
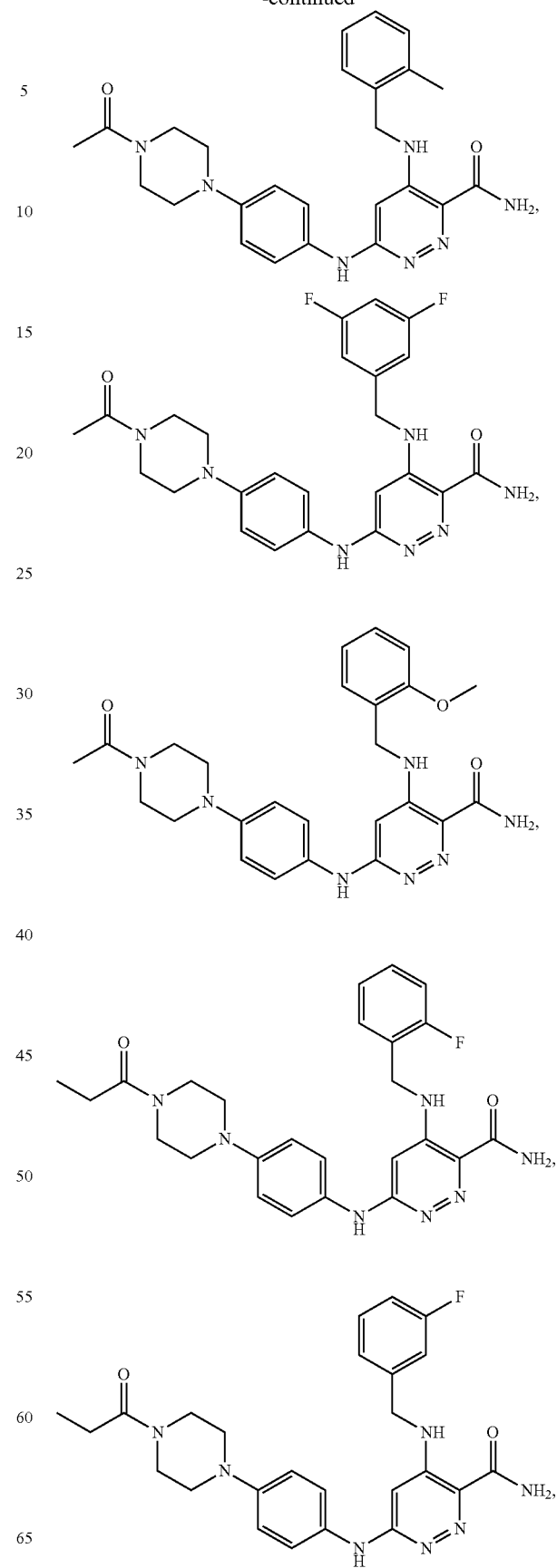

27
-continued
28
-continued
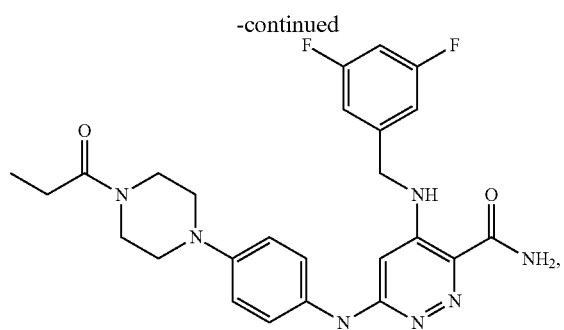
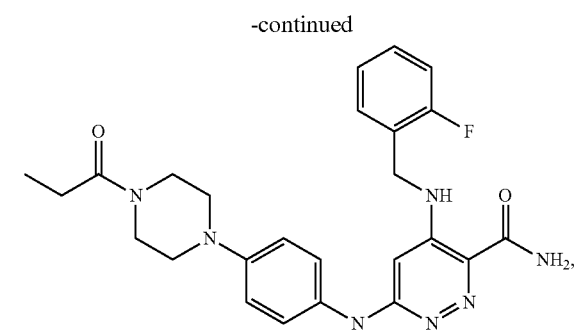
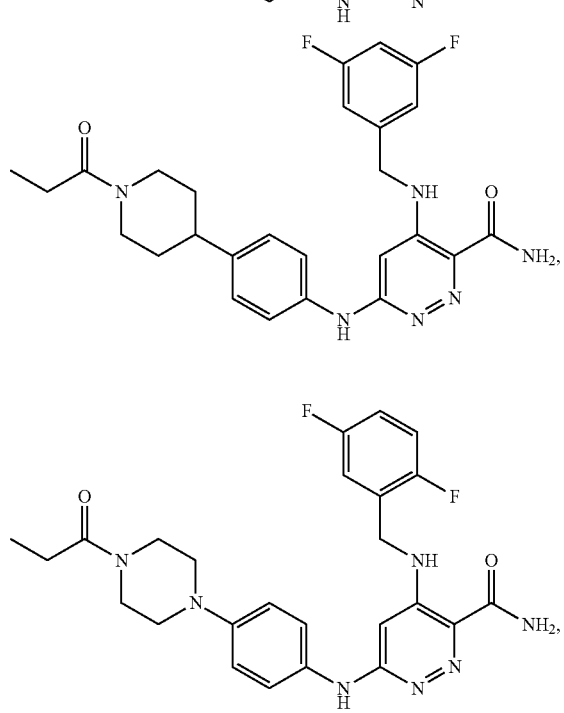
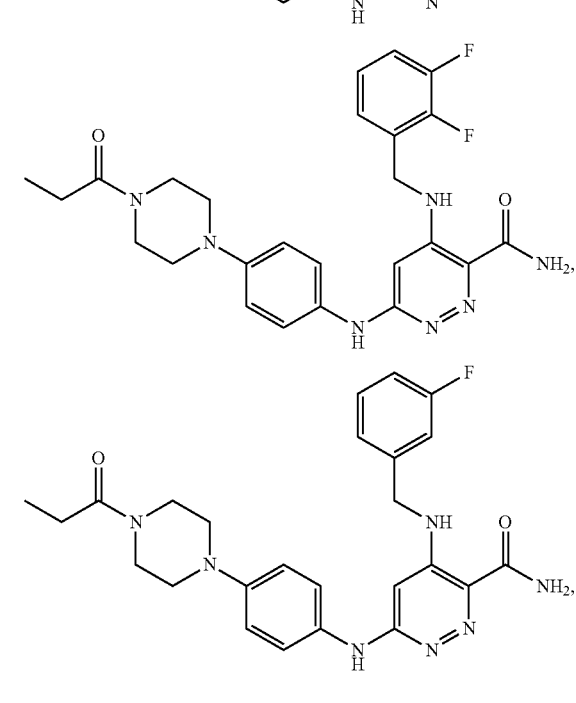
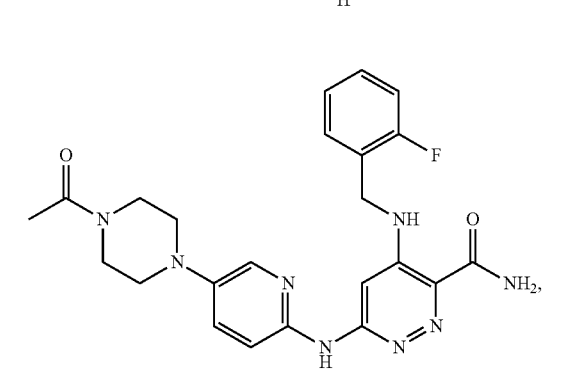
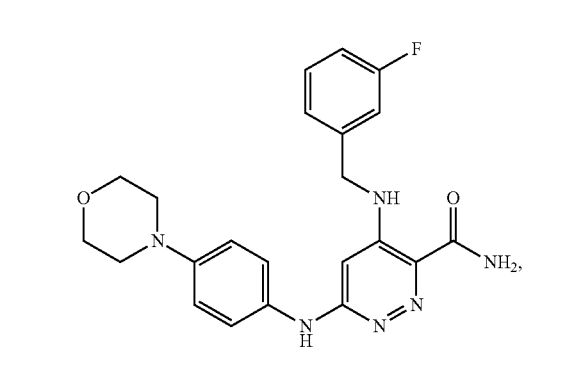
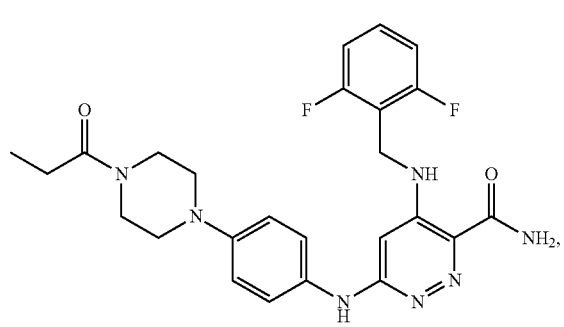
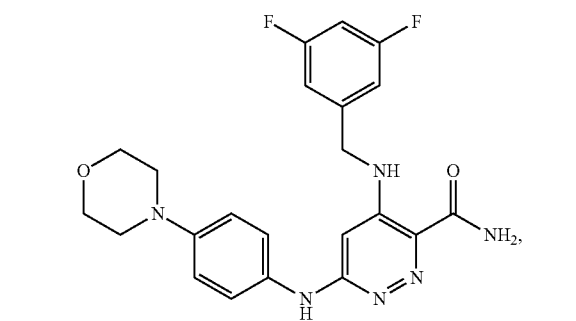

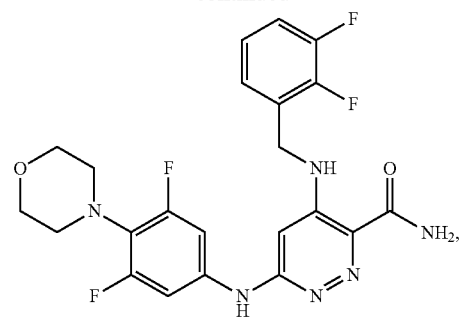
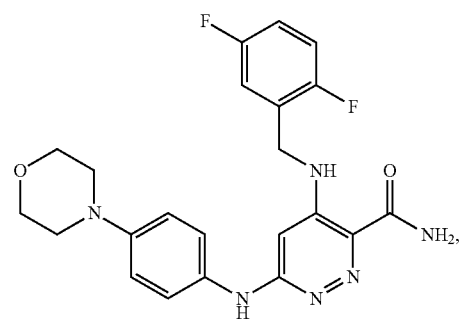
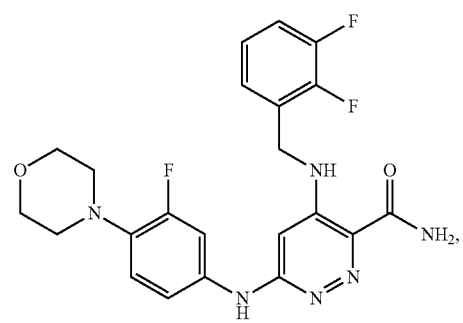
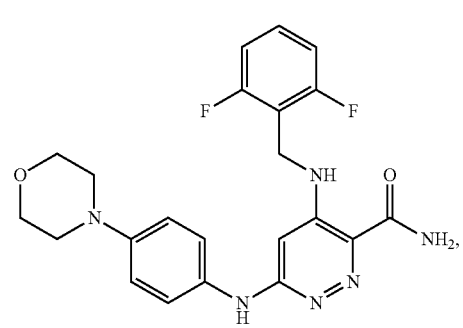
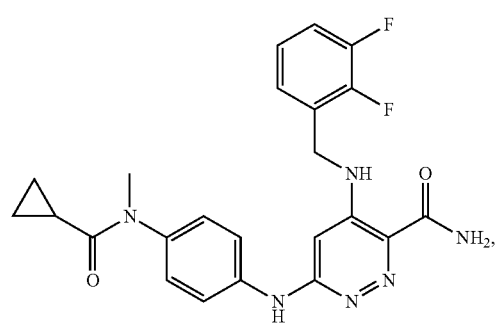
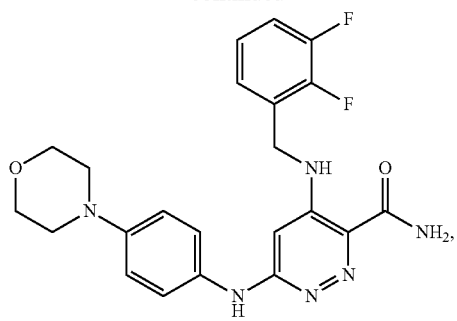
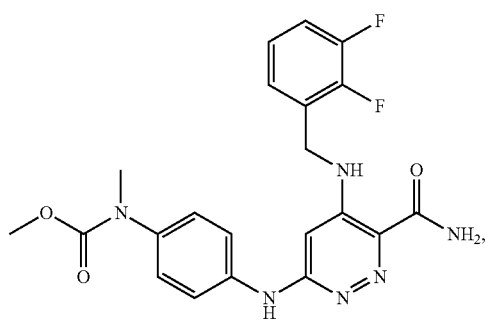
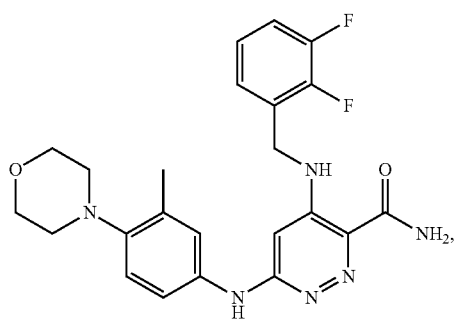
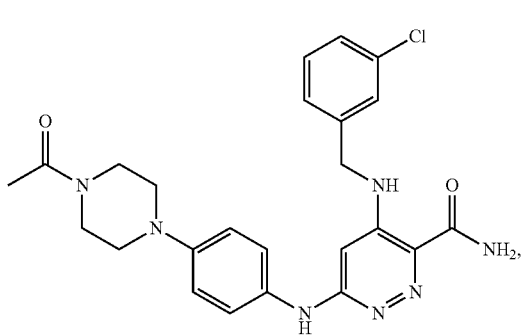
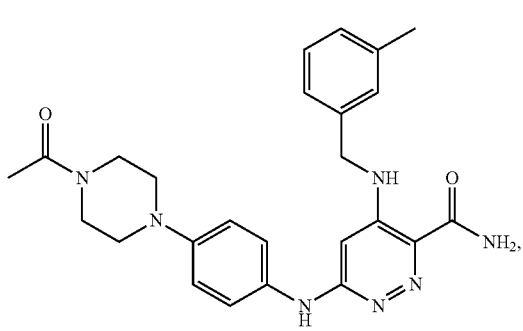

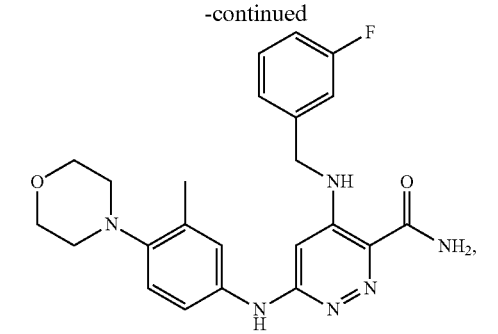
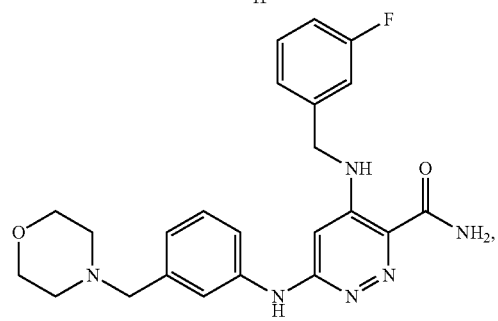
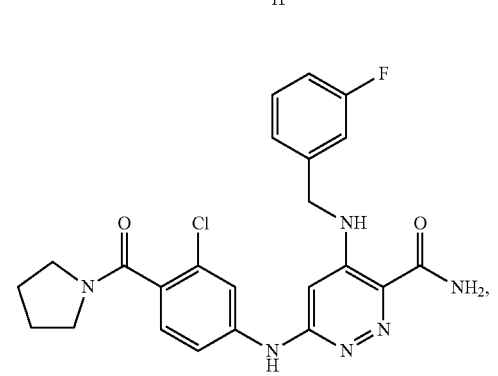
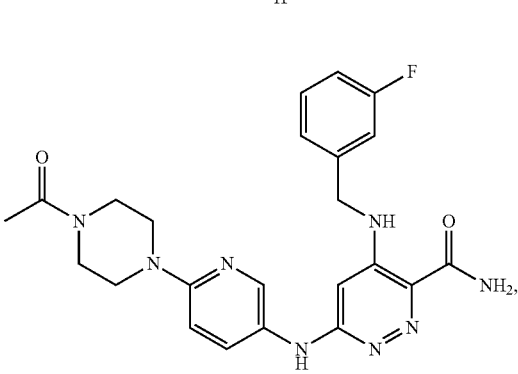
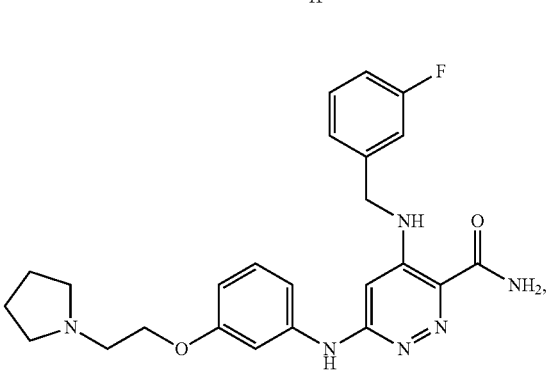
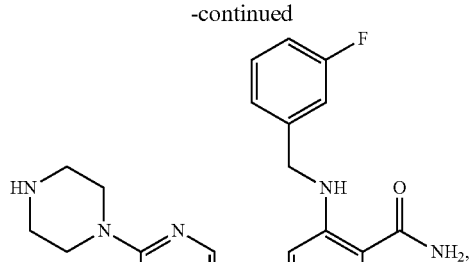
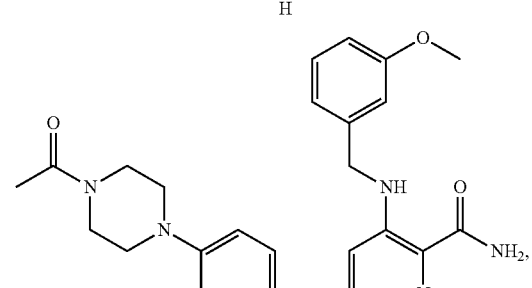
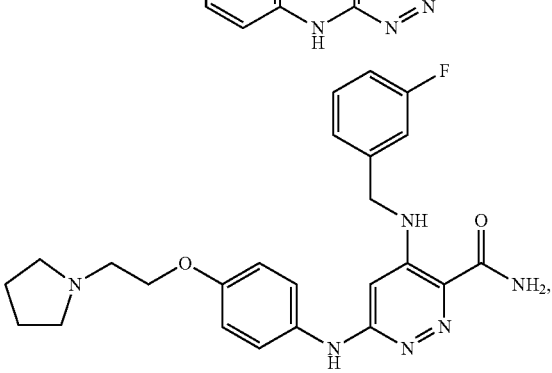
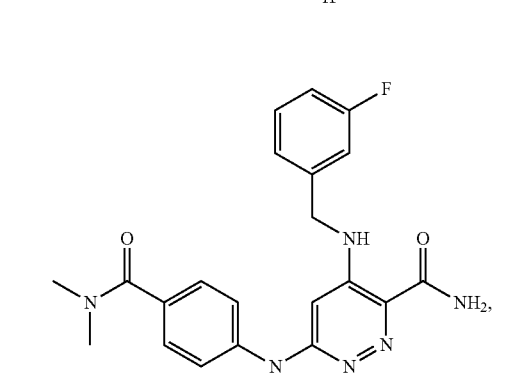
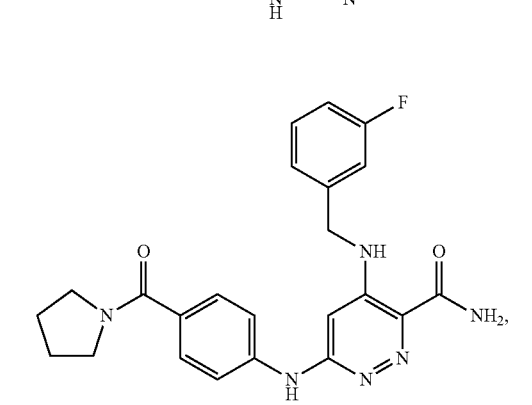

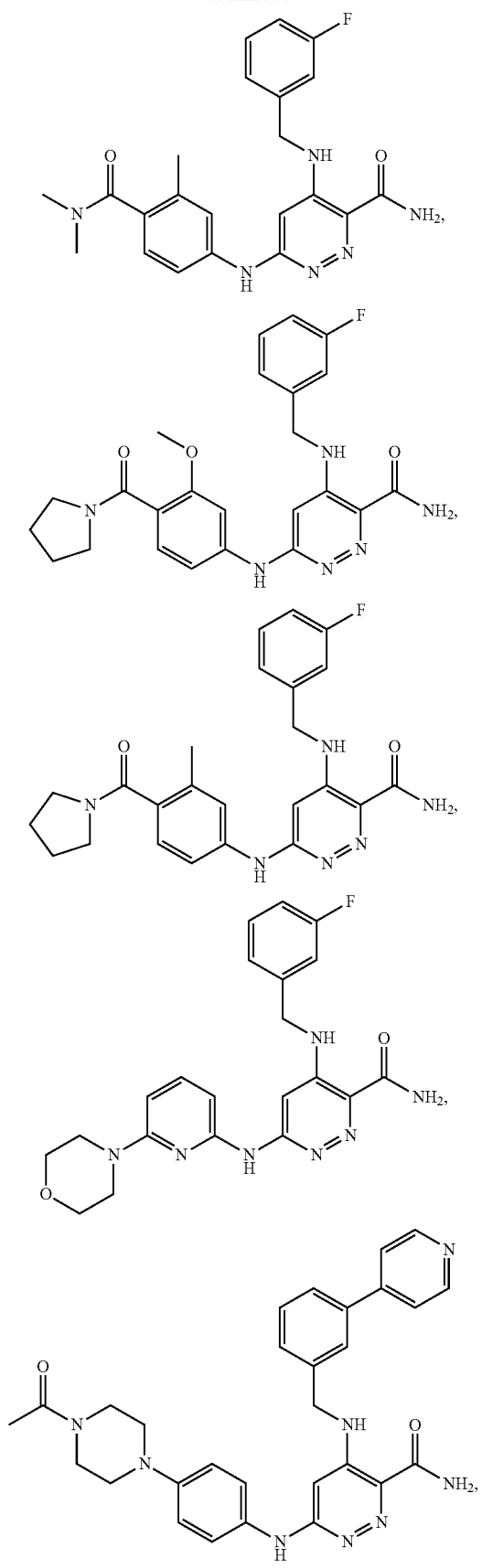
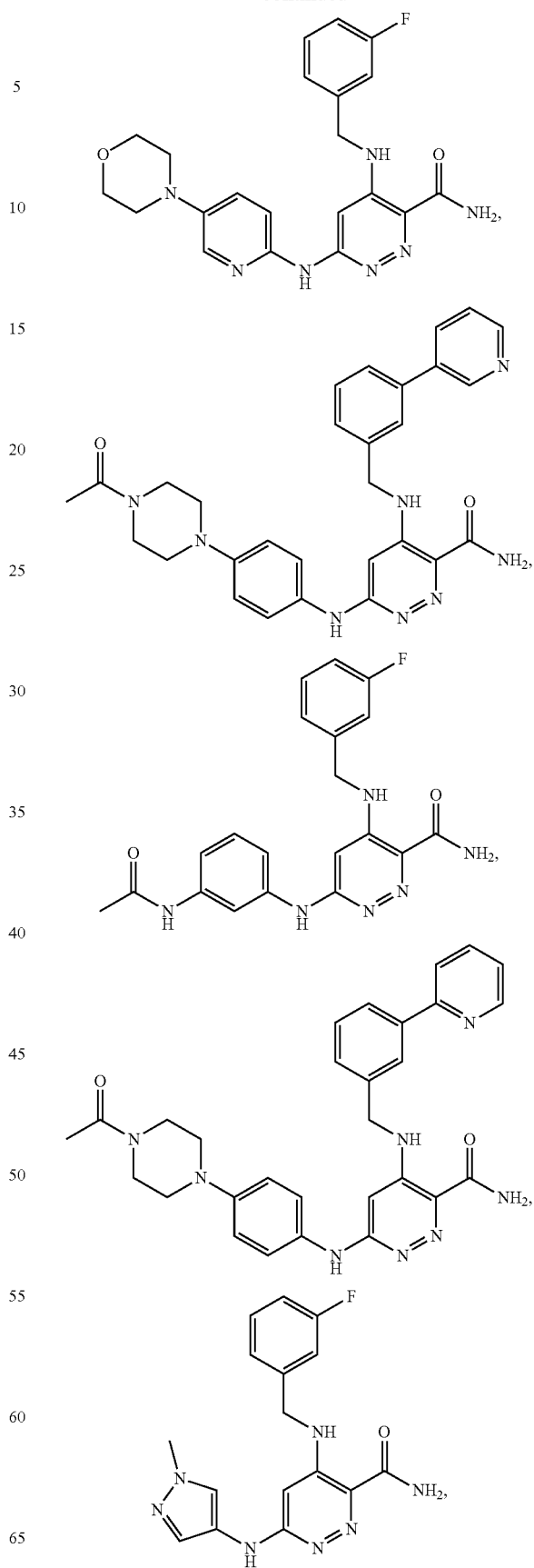

35
-continued
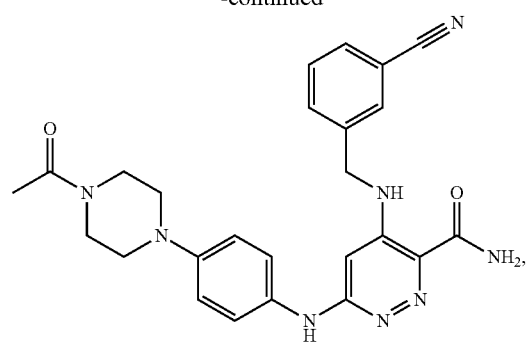
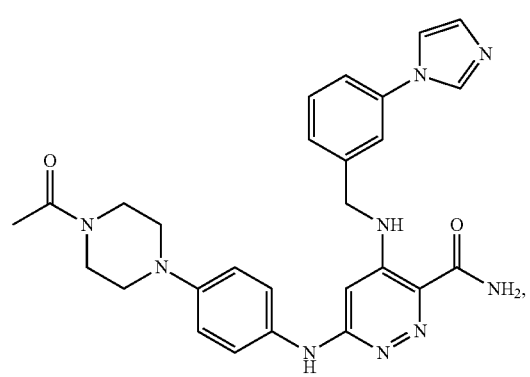
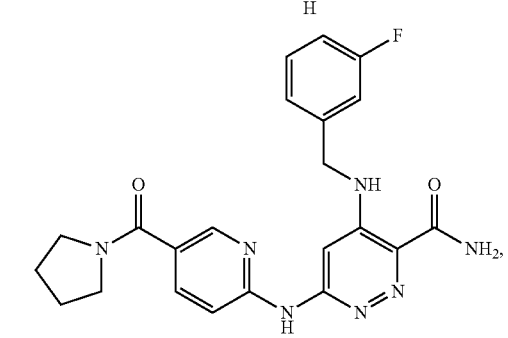
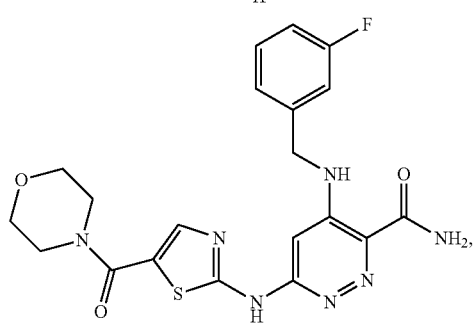
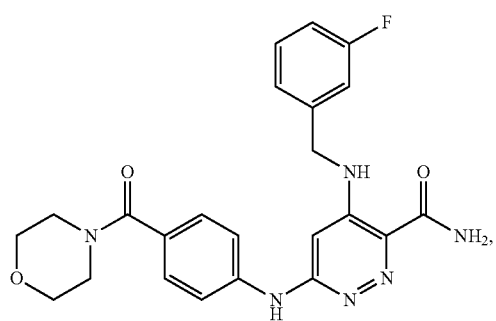
36
-continued
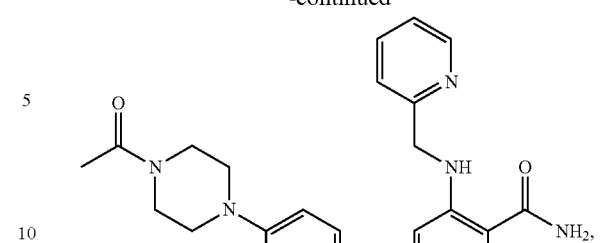
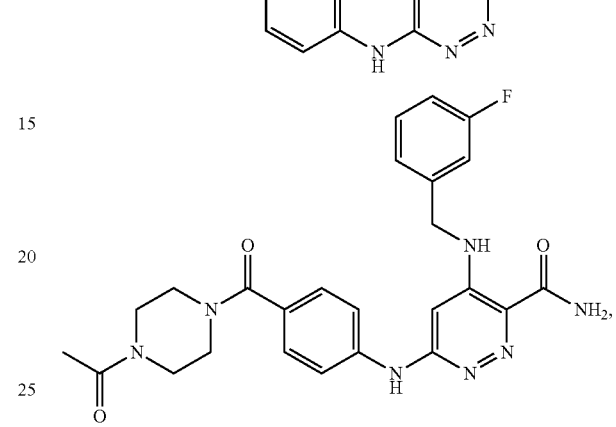
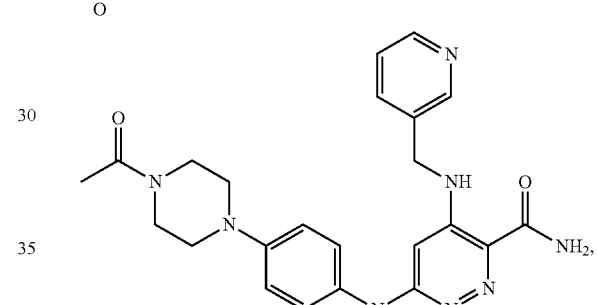
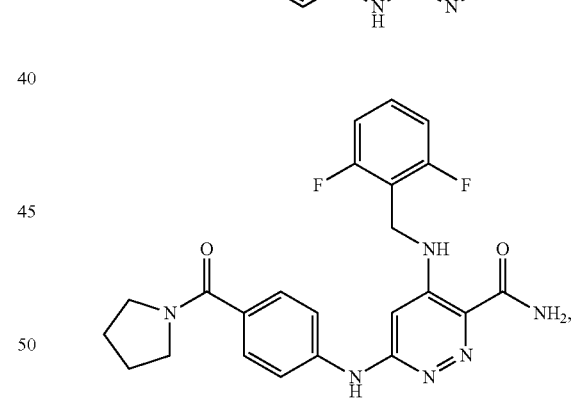
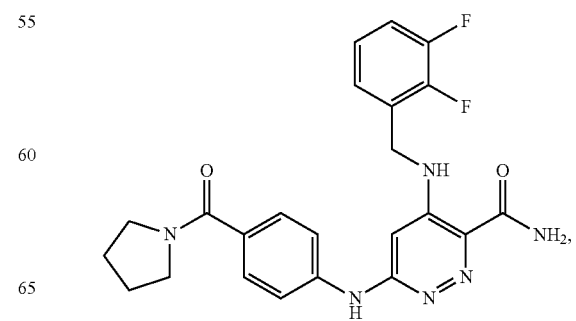

37
-continued
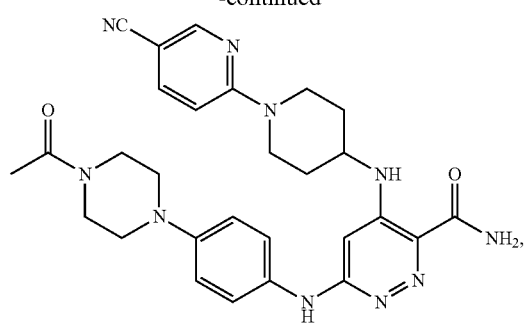
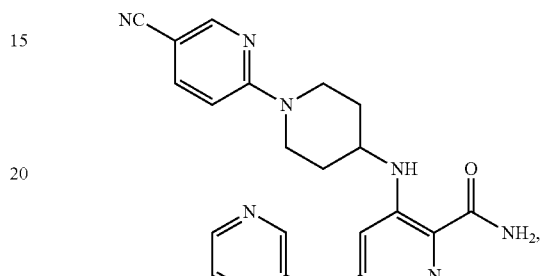
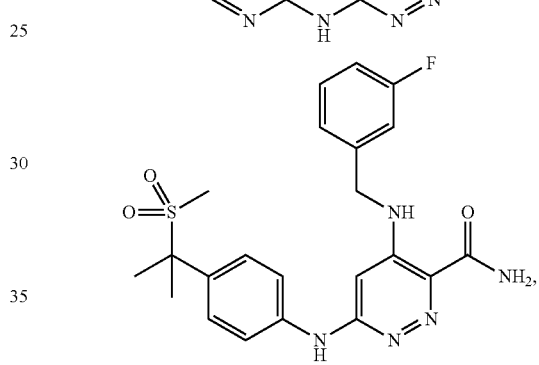
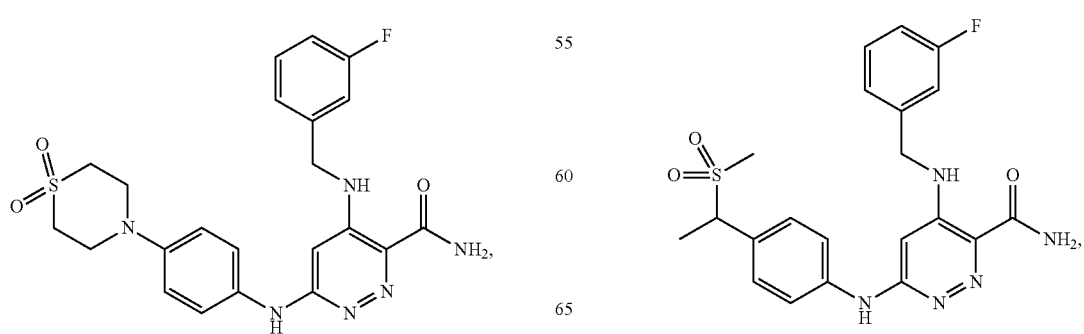
38
-continued
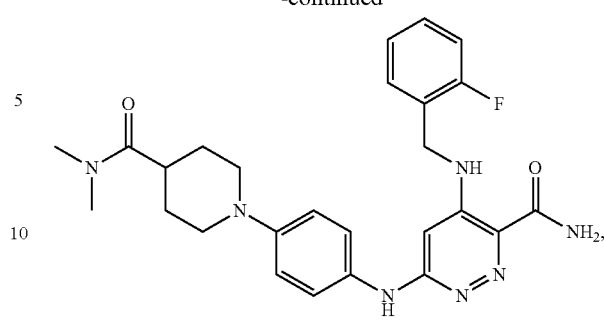
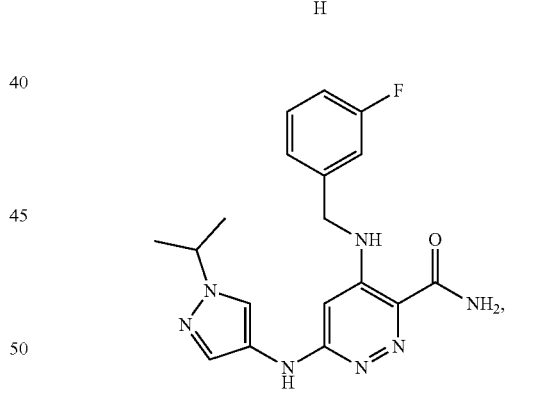

-continued
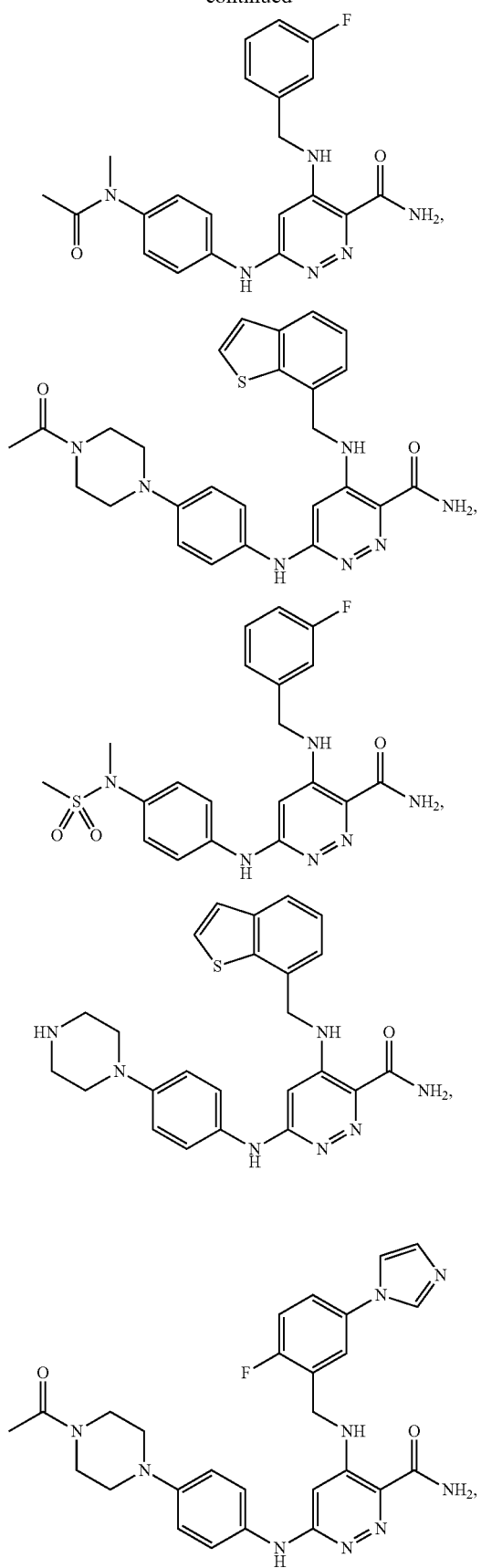
-continued
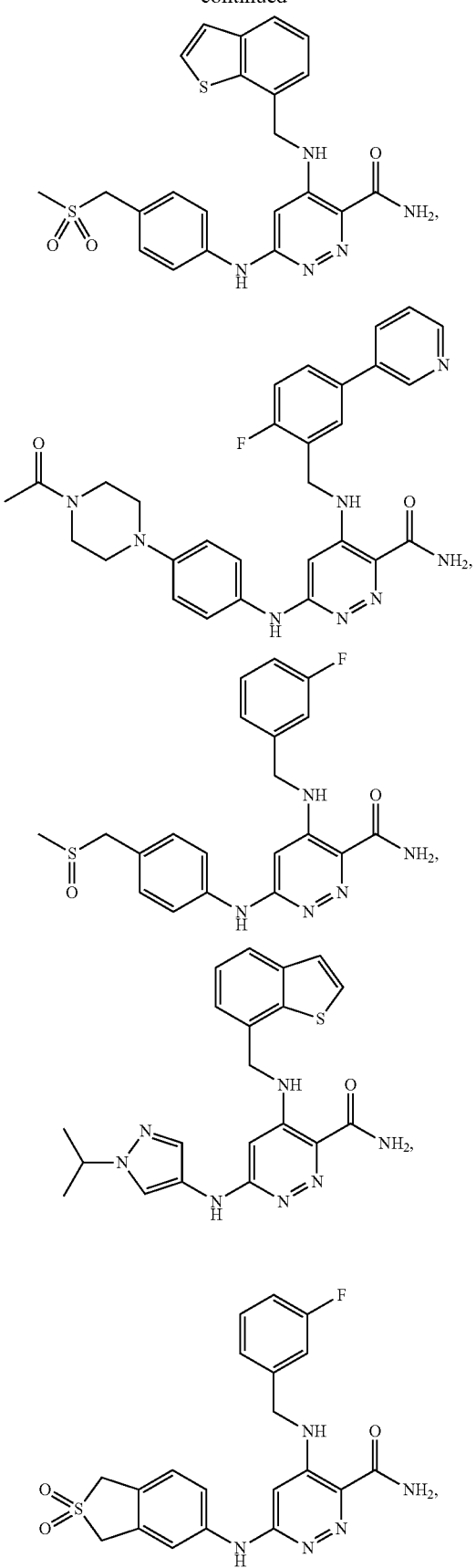

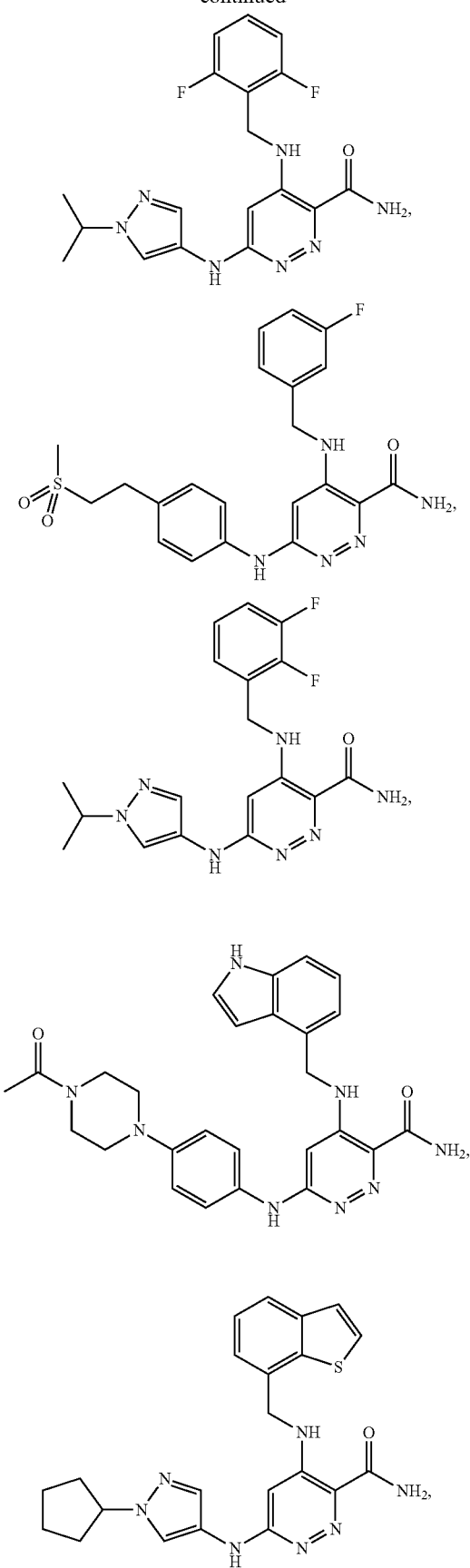
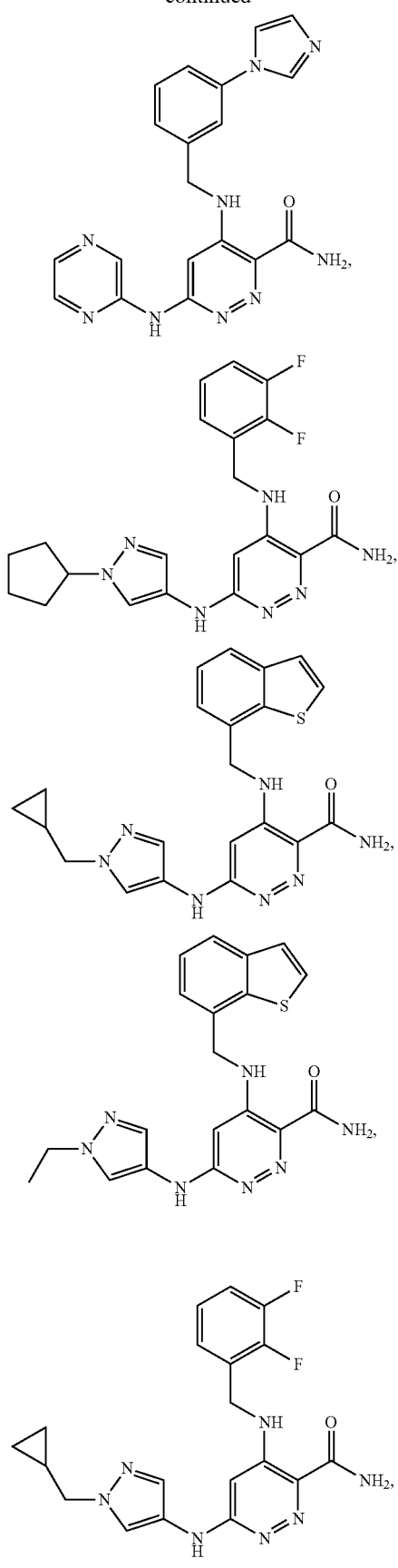

43
-continued
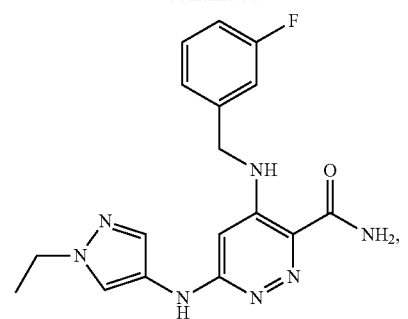
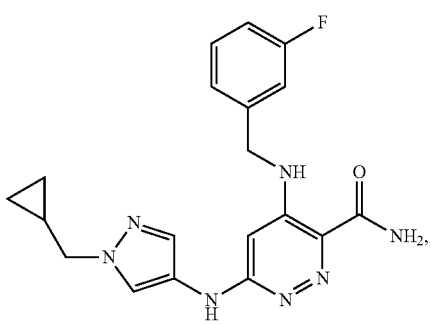
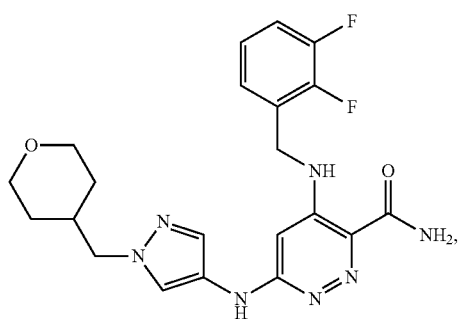
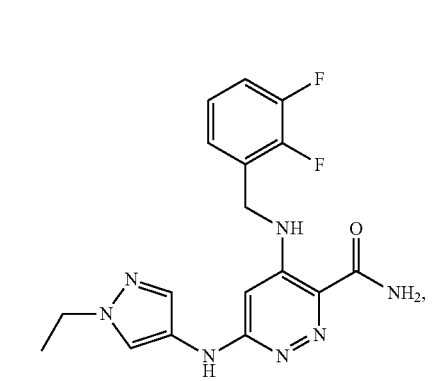
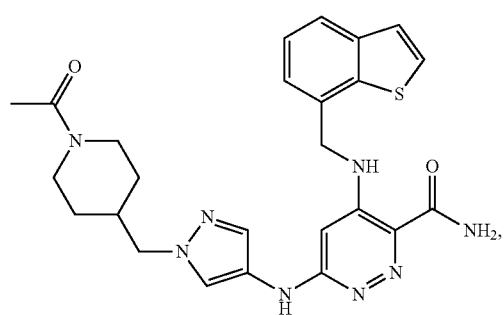
44
-continued
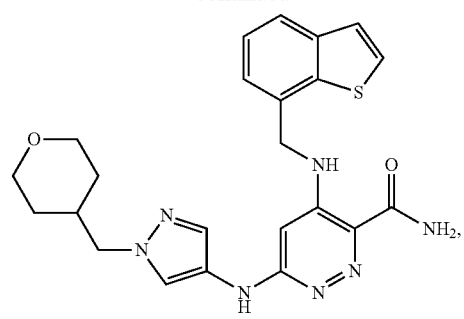
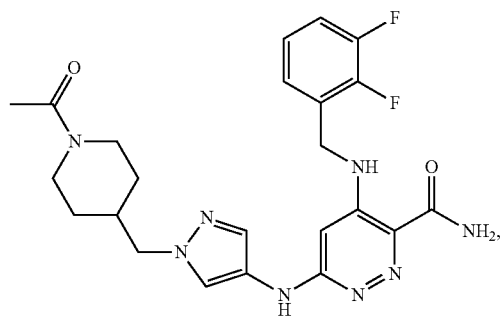
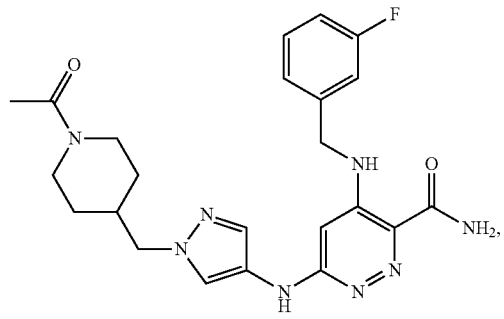
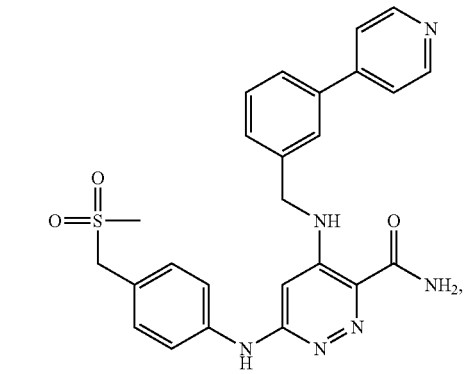
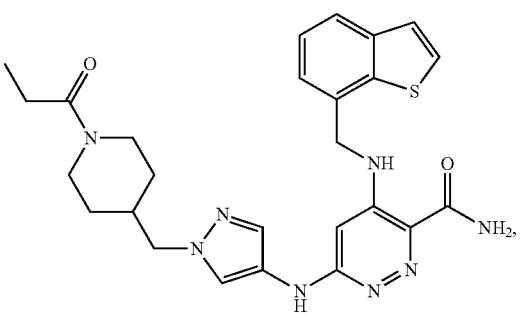

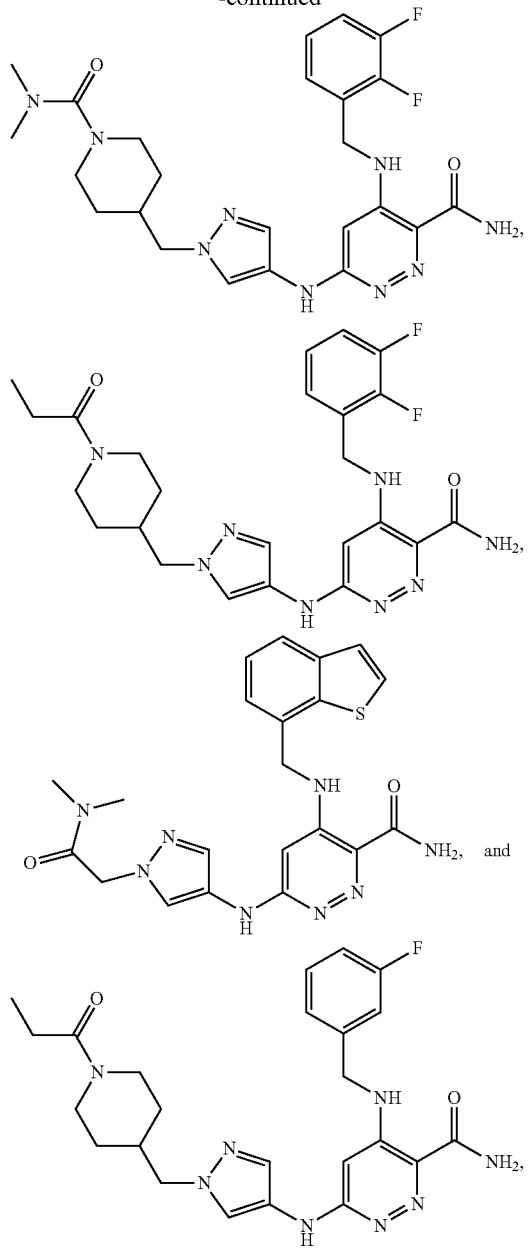
or a pharmaceutically acceptable salt thereof
In one group of embodiments, the compound is selected from:
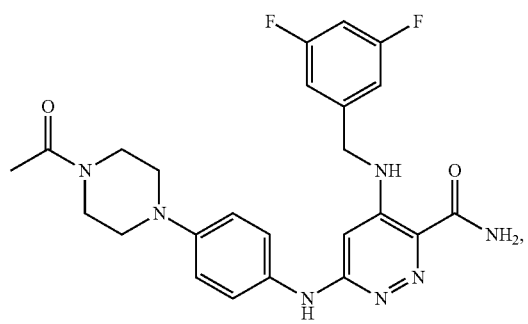
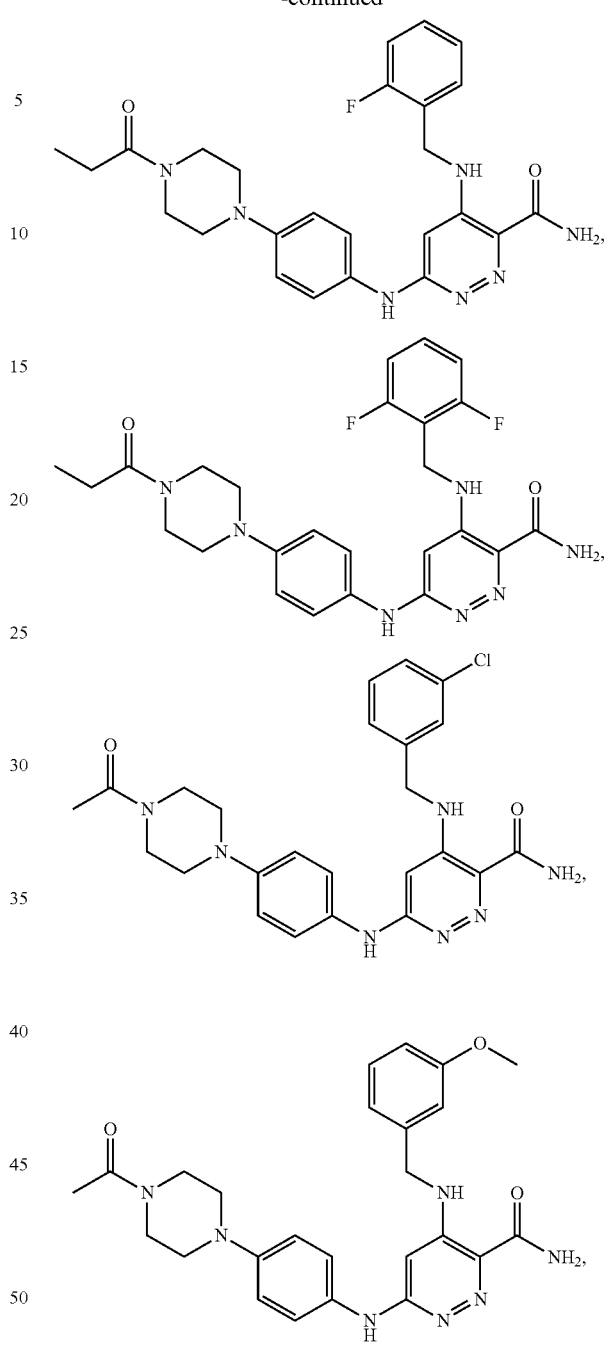
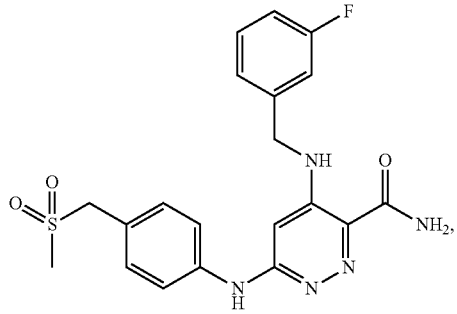

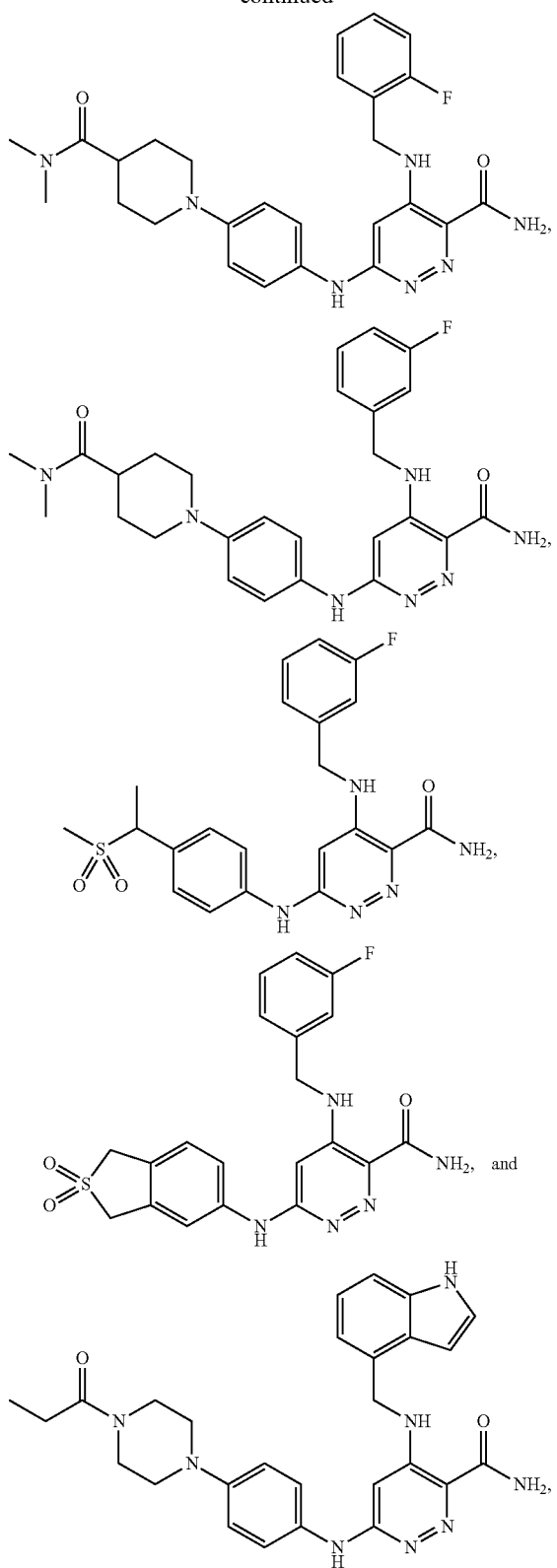

or a pharmaceutically acceptable salt thereof

The compounds of the present invention can be prepared by known organic synthesis techniques, including the methods described in more detail in the Examples. In general, the compounds of structure (I) above may be made by the FIGS. 1-4, wherein all substituents are as defined above unless indicated otherwise.

The pyridazine core can be prepared by a method including a diaza-Wittig reaction as shown in FIG. 1. Keto-diester 1-1 can be converted to the corresponding diazo compound 1-3, which can further be converted to dihydroxy pyridazine 1-5 by treatment with triphenylphosphine and heating under acidic conditions. Dichloro pyridazine Ia can be prepared from the dihydroxy intermediate using phosphoryl chloride. Dichloro pyridazine Ia can be used to prepare a number of compounds according to Formula I.

Figure 2:
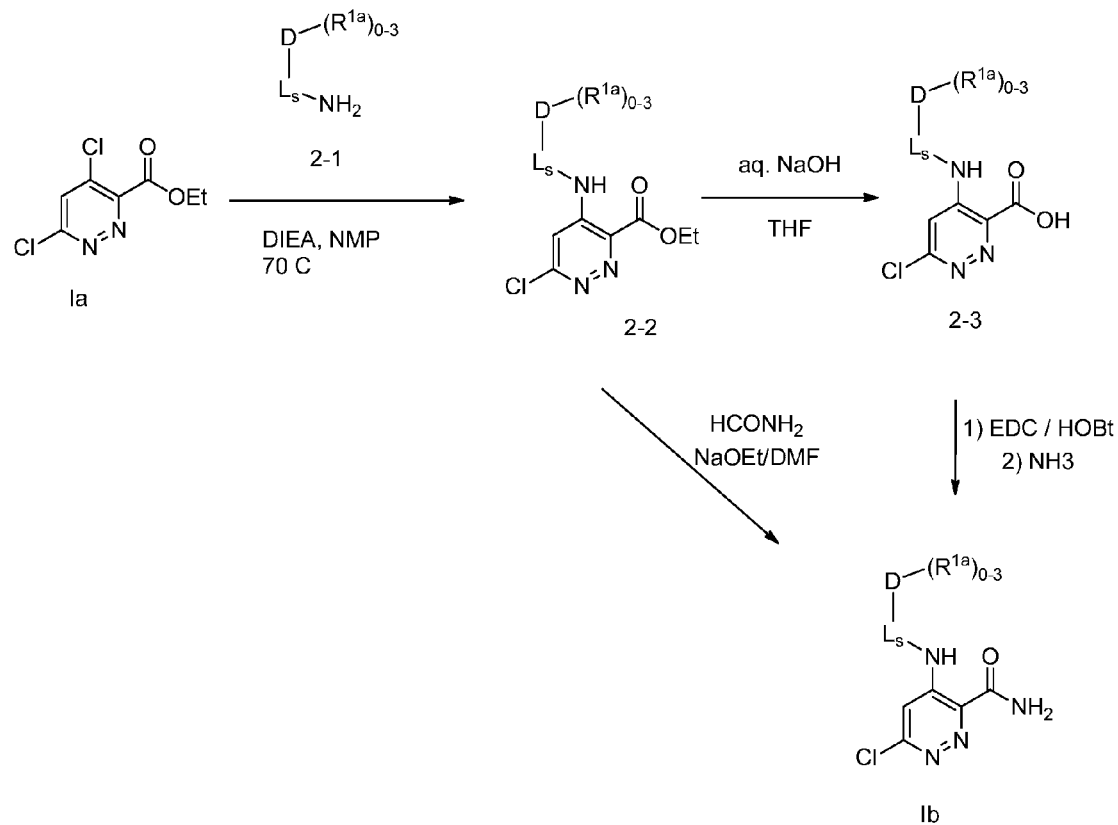
FIG. 2 shows a synthetic route for the preparation of a pyridazine intermediate compound.

As shown in FIG. 2, an appropriate amine 2-1 can be installed at the 4 position of the pyridazine core to provide intermediate 2-2. The ethyl ester moiety can be converted to the corresponding carboxamide Ib via base hydrolysis followed by carbodiimide coupling with ammonia. Alternatively, the ester can be converted to the carboxamide in a single step using formamide in the presence of an alkoxide.

Figure 3:
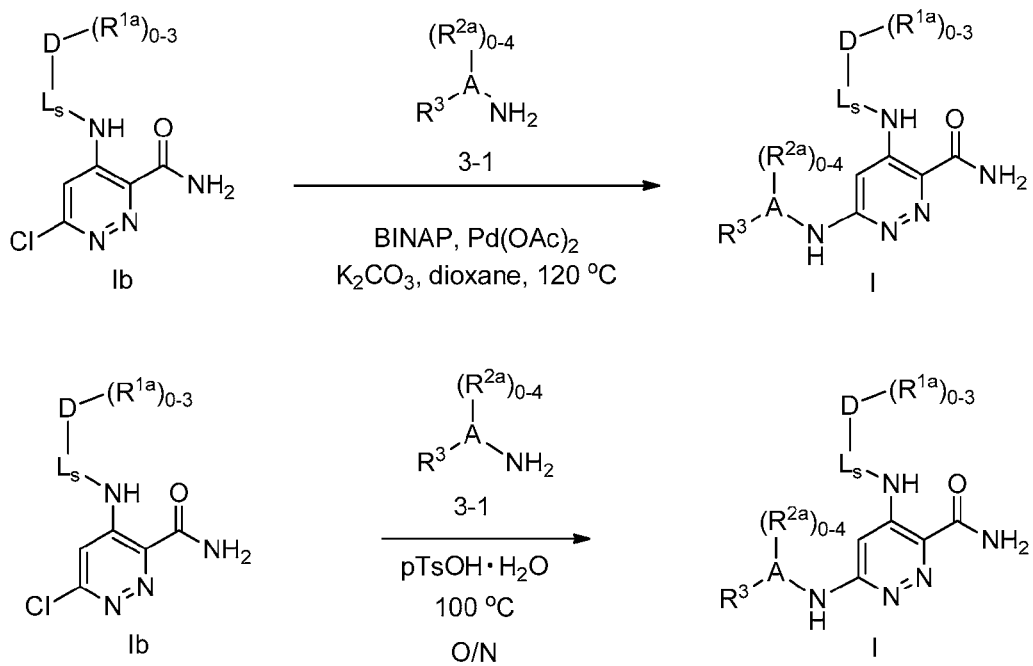
FIG. 3 shows synthetic routes for the preparation of a pyridazine compounds of the invention.

As shown in FIG. 3, an amine 3-1 can be reacted with carboxamide Ib to form a compound of Formula I. The reaction can be catalyzed using a transition metal complex, such as a palladium complex, or a suitable acid.

Figure 4:
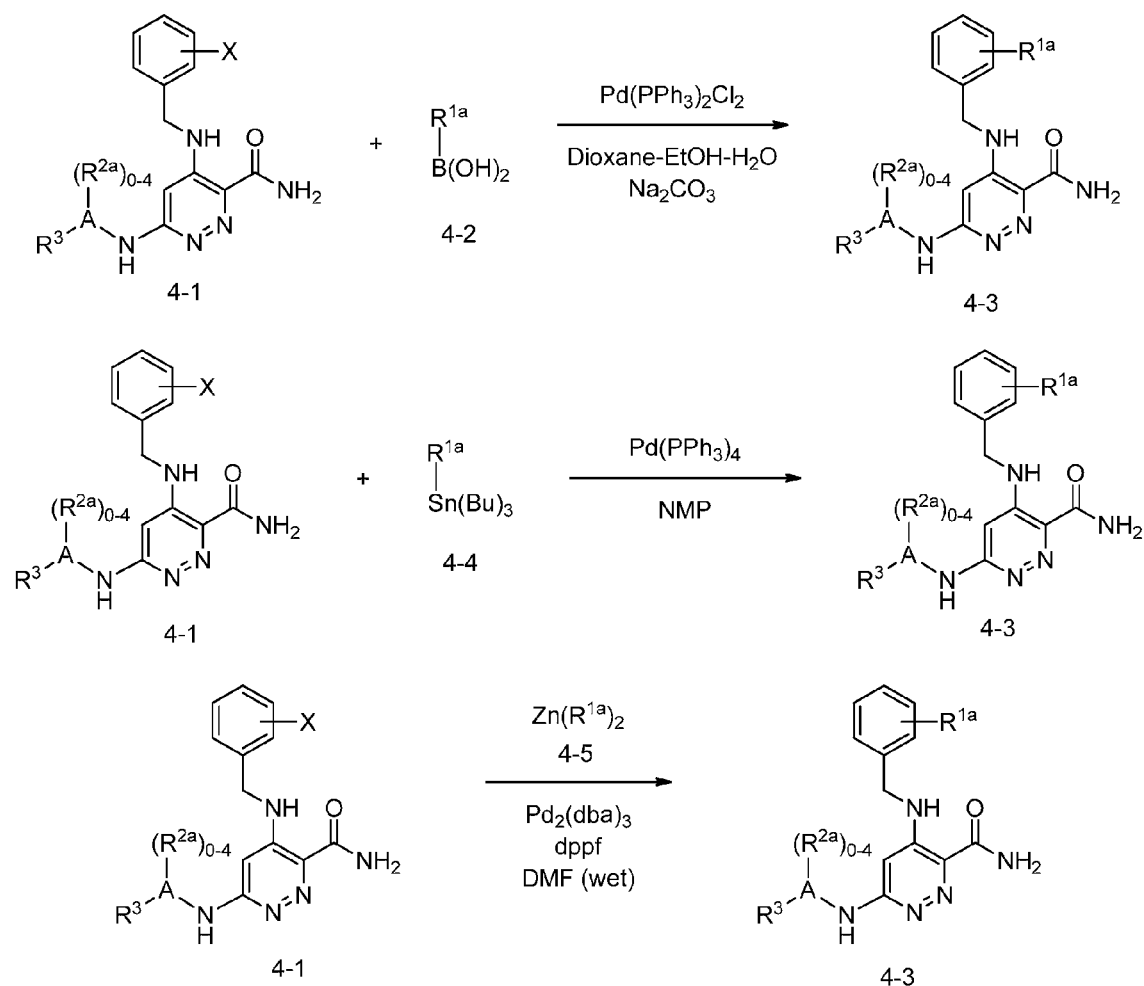
FIG. 4 shows palladium-catalyzed transformation of a common intermediate to provide various compounds of the invention.

In certain embodiments, the "D" moiety of Formula I can be further elaborated after it is appended to the pyridazine core. As shown in FIG. 4, for example, one or more $R^{1a}$ moieties can be added to a suitably-functionalized benzylamine moiety (benzylamine corresponding to the D-L-NH— moiety of Formula I). The $R^{1a}$ moieties can be introduced using a palladium catalyst and suitable boronic acid, a suitable organotin compound, or a suitable organozinc compound.

One of skill in the art will appreciate that the compounds of Formula I can be made by still other methods known to one of skill in the art (see, for example, *Comprehensive Organic Transformations* Richard C. Larock, 1999).

The compounds of the present invention can generally be utilized as free bases. Alternatively, the compounds of this invention can be used in the form of acid addition salts as described below.

III. Compositions

In another aspect, the invention provides a composition comprising a compound of the invention in combination with a pharmaceutically acceptable carrier or diluent.

Depending on the intended mode of administration, the pharmaceutical compositions can be in the form of solid, semi-solid or liquid dosage forms, preferably in unit dosage form suitable for single administration of a precise dosage. In addition to an effective amount of the active compound(s), the compositions can contain suitable pharmaceutically-acceptable excipients, including adjuvants which facilitate processing of the active compounds into preparations which can be used pharmaceutically.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered can also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

The term "administering" refers to administration by any route, including parenteral and transmucosal (e.g., buccal, sublingual, palatal, gingival, nasal, vaginal, rectal, or transdermal).

For oral administration, the composition will generally take the form of a tablet or capsule, or it can be an aqueous or nonaqueous solution, suspension, or syrup. Tablets and capsules for oral use will generally include one or more commonly used excipients such as lactose and corn starch. Lubricating agents, such as magnesium stearate, are also typically added. When liquid suspensions are used, the active agent can be combined with emulsifying and suspending excipients. If desired, flavoring, coloring and/or sweetening agents can be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation can also be a sterile injectable solution or a suspension in a nontoxic parenterally acceptable diluent or solvent. Among the acceptable vehicles and solvents that can be employed are water, Ringer's solution, and isotonic sodium chloride solution. In addition, sterile, fixed oils, fatty esters or polyols are conventionally employed as solvents or suspending media.

The pharmaceutical compositions of this invention can also be formulated in lyophilized form for parenteral administration. Lyophilized formulations can be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients can be added to enhance or stabilize the composition, or to facilitate preparation of the composition.

Typically, a pharmaceutical composition of the present invention is packaged in a container with a label, or instructions, or both, indicating use of the pharmaceutical composition in the treatment of the indicated disease.

The pharmaceutical composition can additionally contain one or more other pharmacologically active agents in addition to a compound of this invention.

Dosage forms containing effective amounts of the modulators are within the bounds of routine experimentation and within the scope of the invention. A therapeutically effective dose can vary depending upon the route of administration and dosage form. Certain compounds and formulations of the invention exhibit a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

IV. Methods of Use

In another aspect, the invention provides methods of inhibiting or decreasing JAK activity as well as treating or ameliorating a JAK associated state, symptom, condition, disorder or disease in a patient in need thereof (e.g., human or non-human). In one embodiment, the JAK associated state, symptom, condition, disorder or disease is mediated, at least in part by JAK activity. In more specific embodiments, the present invention provides a method for treating a condition or disorder mediated at least in part by JAK activity is cardiovascular disease, inflammatory disease or autoimmune disease.

The compounds described herein are also potent and/or selective inhibitors of JAKs. As a consequence of this activity, the compounds can be used in a variety of in vitro, in vivo, and ex vivo contexts to regulate or inhibit JAK activity, signaling cascades in which JAKs play a role, and the biological responses effected by such signaling cascades. For example, in one embodiment, the compounds can be used to inhibit JAK, either in vitro or in vivo, in virtually any cell type expressing the JAK, such as in hematopoietic cells in which, for example, JAK3 is predominantly expressed. They may also be used to regulate signal transduction cascades in which JAKs, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/Ramos CD23 up-regulation and IL-2 mediated T-cell proliferation. Importantly, the compounds can be used to inhibit JAKs in vivo as a therapeutic approach towards the treatment or prevention of diseases mediated, either wholly or in part, by a JAK activity (referred to herein as "JAK mediated diseases"). Non-limiting examples of JAK mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoriasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAKs that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas and some solid tumors.

In certain embodiments, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAKs play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compound can also be administered to a tissue or an organ prior to transplanting the tissue or organ in the transplant recipient.

In certain embodiments, the invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments, the autoimmune disease is multiple sclerosis (MS), psoriasis, or Sjogran's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, µLcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formula (I). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, µLcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth under the brand name RAPAMUNE; tacrolimus is currently available from Fujisawa under the brand name PROGRAF; cyclosporine is current available from Novartis under the brand name SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a Syk. Syk is a tyrosine kinase known to play a critical role in Fey receptor signaling, as well as in other signaling cascades, such as those involving B-cell receptor signaling (Turner et al., (2000), Immunology Today 21:148-154) and integrins beta(1), beta (2), and beta (3) in neutrophils (Mocsai et al., (2002), Immunity 16:547-558). For example, syk plays a pivotal role in high affinity IgE receptor signaling in mast cells that leads to activation and subsequent release of multiple chemical mediators that trigger allergic attacks. However, unlike the JAKs, which help regulate the pathways involved in delayed or cell-mediated Type IV hypersensitivity reactions, syk helps regulate the pathways involved in immediate IgE-mediated, Type I hypersensitivity reactions. Certain compounds that affect the syk pathway may or may not also affect the JAK pathways.

Suitable syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The compounds described herein and syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a JAK inhibitory compound or one of the other current treatments for the particular disease. The compounds could also be used in combination with syk inhibitory compounds in patients that are JAK-compound resistant or non-responsive. Suitable JAK-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits JAK with an $IC_{50}$ in the range of at least 10 µM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 plays a role, comprising contacting a cell expressing a receptor involved in such a signaling cascade with a compound wherein the compound is selected from the compounds of this invention, as described herein.

In another embodiment, this invention provides a method of treating or preventing a JAK-mediated disease, comprising administering to a subject an amount of compound effective to treat or prevent the JAK-mediated disease, wherein the compound is selected from the compounds of this invention, as described herein.

In another embodiment, this invention provides a method of treating or preventing a JAK-mediated disease, in which the JAK-disease is HVGR or GVHR, comprising administering to a subject an amount of compound effective to treat or prevent the JAK-mediated disease, wherein the compound is selected from the compounds of the invention, as described herein.

In another embodiment, this invention provides a method of treating or preventing a JAK-mediated disease, in which the JAK-disease is acute allograft rejection, comprising administering to a subject an amount of compound effective to treat or prevent the JAK-mediated disease, wherein the compound is selected from the compounds of the invention, as described herein.

In another embodiment, this invention provides a method of treating or preventing a JAK-mediated disease, in which the JAK-mediated disease is chronic allograft rejection, comprising administering to a subject an amount of compound effective to treat or prevent the JAK-mediated disease, wherein the compound is selected from the compounds of the invention, as described herein.

Active compounds of the invention typically inhibit the JAK/Stat pathway. The activity of a specified compound as an inhibitor of a JAK can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express JAK. Examples of mammals include mice, rats, cows, sheep, pigs, goats, horses, bears, monkeys, dogs, cats and, preferably, humans. Transgenic organisms which express JAK are also included in this definition.

The inventive methods comprise administering an effective amount of a compound or composition described herein to a mammal or non-human animal. As used herein, "effective amount" of a compound or composition of the invention includes those amounts that antagonize or inhibit JAK. An amount which antagonizes or inhibits JAK is detectable, for example, by any assay capable of determining JAK activity, including the one described below as an illustrative testing method. Effective amounts may also include those amounts which alleviate symptoms of a JAK associated disorder treatable by inhibiting JAK. Accordingly, "antagonists of JAK" include compounds which interact with the JAK, respectively, and modulate, e.g., inhibit or decrease, the ability of a second compound, e.g., another JAK ligand, to interact with the JAK, respectively. The JAK binding compounds are preferably antagonists of JAK, respectively. The language "JAK-binding compound" (e.g., exhibits binding affinity to the receptor) includes those compounds which interact with JAK resulting in modulation of the activity of JAK, respectively. JAK binding compounds may be identified using an in vitro (e.g., cell and non-cell based) or in vivo method.

The amount of compound present in the methods and compositions described herein should be sufficient to cause a detectable decrease in the severity of the disorder, as measured by any of the assays described in the examples. The amount of JAK modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula (I), another therapeutic agent (e.g., methotrexate) or a pharmaceutically acceptable salt, ester or prodrug thereof, and a pharmaceutically acceptable excipient or carrier.

The invention comprises a compound having the formula (I), a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease (IBD), asthma, chronic obstructive pulmonary disease (COPD) and multiple schlerosis (MS). The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are either potent inhibitors of JAK kinases, exhibiting $IC_{50}$s in the respective assay in the range of less than 5 µM, with most being in the nanomolar, and several in the sub-nanomolar, range. In some embodiments, the compounds of the present invention may be "dual" syk/JAK inhibitors in that they inhibit both syk and JAK kinase to some degree. In other embodiments, the compounds of the present invention may selectively inhibit JAK kinase, but not appreciably inhibit syk kinase.

Accordingly, some embodiments of the invention provide a method for inhibiting JAK kinase or a signal transduction pathway mediated at least in part by JAK kinase activity. The method includes the step of contacting a cell with a compound of the invention. In certain embodiments of the methods described herein, the method is carried out in vivo.

The invention provides also provides methods for treating a condition or disorder mediated at least in part by JAK kinase activity in a subject. The methods include the step of administering to a subject in need of such treatment a therapeutically effective amount of a composition of the invention.

In some embodiments, the JAK is selected from the group consisting of JAK1, JAK2, and JAK3. In some embodiments, the JAK is JAK1 or JAK3. In some embodiments, the JAK is JAK3.

In some embodiments, the condition or disorder is selected from the group consisting of cardiovascular disease, inflammatory disease, immune-related disease, autoimmune disease and cell proliferative disorder.

In some embodiments, the inflammatory disease, immune-related disease, autoimmune disease is selected from the group consisting of organ transplants, asthma, COPD, systemic lupus, erythematosus, multiple sclerosis, rheumatoid arthritis, Crohn's disease, Type I diabetes, psoriasis.

In some embodiments, the sickle cell disease is selected from the group consisting of sickle cell anemia, sickle-hemoglobin C disease, sickle beta-plus thalassemia, and sickle beta-zero thalassemia.

V. Examples

Example 1

Synthesis of 6-((4-(4-acetylpiperazin-1-yl)phenyl) amino)-4-(benzylamino)-pyridazine-3-carboxamide (Compound 5)

Figure 5:
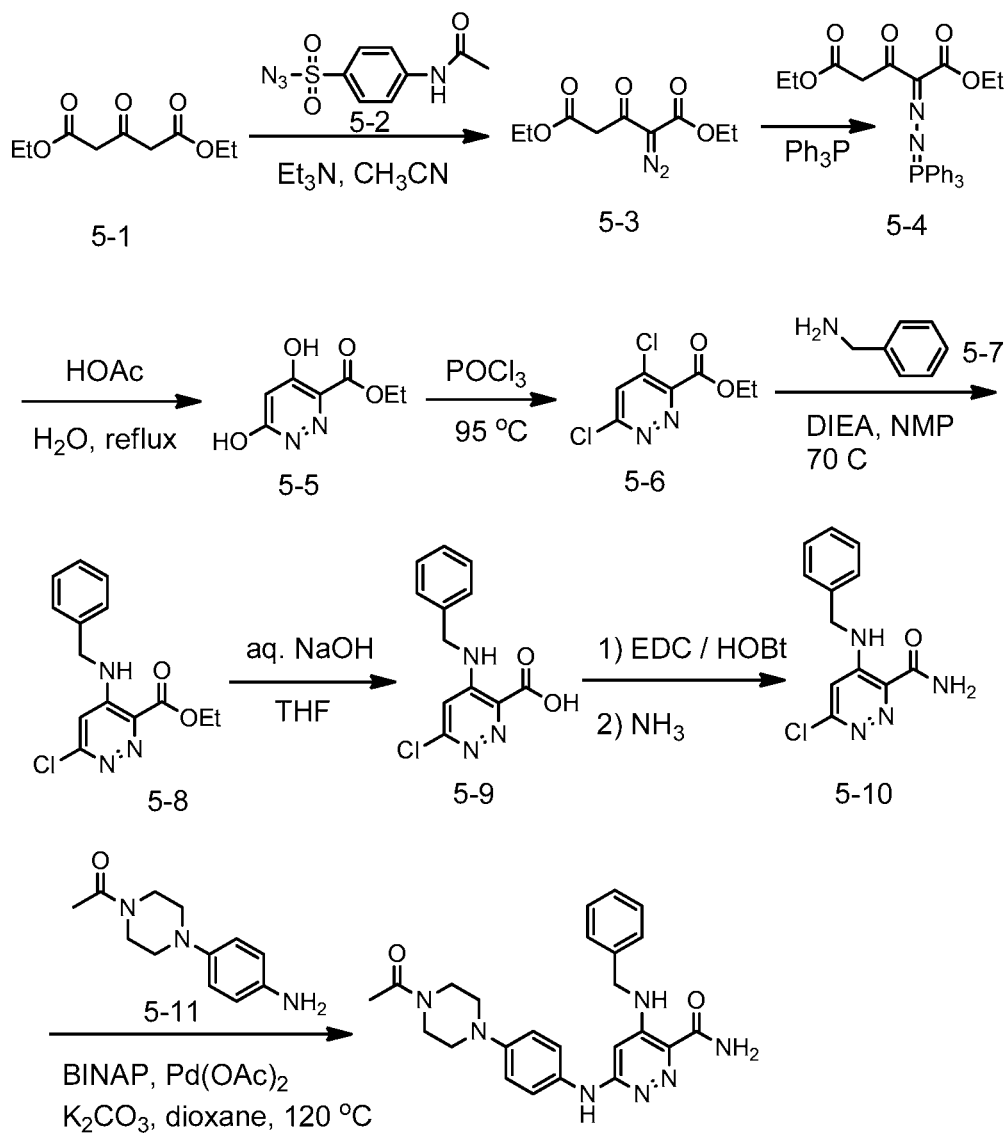
FIG. 5 shows a synthetic route for the preparation of 6-((4-(4-acetylpiperazin-1-yl)phenyl)amino)-4-(benzylamino)-pyridazine-3-carboxamide.

Compound 5 was synthesized as shown in FIG. 5.

To a solution of diethyl 1,3-acetonedicarboxylate (compound 5-1, 4.53 ml, 25 mmol) and triethylamine (3.82 mL, 27.5 mmol) in acetonitrile (100 ml) at 0° C., 4-acetamido benzenesulfonyl azide (compound 5-2, 6 g, 25 mmol) was added in small portions and stirred at room temperature for 4 hr. The solid precipitated was filtered, washed with 1:1 hexane/ether and the filtrate was concentrated in vacuum. The residue was redissolved in 1:1 hexane/ether and the insoluble material filtered off, the filtrate was concentrated to give desired compound 5-3 as an yellow oil (5.63 g).

A mixture of 5-3 (5.63 g, 24.7 mmol) and triphenyl phosphine (6.57 g, 25.1 mmol) in ether (50 ml) was stirred at room temperature for 21 hr followed by concentration in vacuum to afford crude 5-4. The residue 5-4 was dissolved in acetic acid (45 ml) and water (5 ml) and then refluxed at 135° C. overnight. The reaction mixture was concentrated and the crude residue was purified by column chromatography eluting with 0-20% MeOH in CH2Cl2 to give desired compound 5-5 as a yellow solid (3.38 g).

A mixture 5-5 (3.38 g, 18.3 mmol) in $POCl_3$ (35 ml) was heated at 95° C. for 5 hr. The excess $POCl_3$ was removed under vacuum, to the residue ice was added followed by ethyl acetate. The organic phase was separated, washed with 5% $NaHCO_3$, dried over $Na_2SO_4$, and concentrated to give compound 5-6 as an oil (3.27 g).

To a solution of 5-6 (221 mg, 1 mmol) was added benzylamine (5-7, 110 μL, 1 mmol) and DIEA (350 μL, 2.01 mmol) in NMP (3 ml) and heated the mixture at 70° C. for 3 hr. To this were added water and ethyl acetate. The organic phase was washed with 5% $NaHCO_3$, dried and concentrated to give 5-8 (327 mg).

To a solution of 5-8 (1 mmol) in THF (5 ml), aq 1N NaOH (4 ml, 4 mmol) was added and stirred for 4 hr. To this was added EtOAc and the phases were separated. The aqueous phase was acidified with 1N HCl to pH 2-3, and then the desired acid compound was extracted with 2-3 portions ethyl acetate. The ethyl acetate layer was dried and concentrated in vacuo to give a solid 5-9.

A solution of compound 5-9 (126 mg, 0.478 mmol), HOBt (90 mg, 0.588 mmol) and EDC (110 mg, 0.573 mmol) in DMF (5 ml) was stirred at room temperature for 40 min. Ammonium hydroxide (14N, 0.200 ml, 2.80 mmol) was added and the reaction mixture for was stirred for 6 hr. To this was then added water and ethyl acetate. The organic layer was separated, washed with 5% $NaHCO_3$, dried and concentrated to give solid 5-10(90 mg).

A mixture of 5-10 (90 mg, 0.342 mmol), 1-(4-(4-aminophenyl)piperazin-1-yl)ethanone (aniline, 78 mg, 0.356 mmol), $K_2CO_3$ (100 mg, 0.724 mmol), BINAP (32 mg, 0.051 mmol) and $Pd(OAc)_2$ (18 mg, 0.080 mmol) in dioxane (2 ml) was degassed with argon and then heated at 120° C. overnight. The reaction mixture was concentrated and then purified by RP-HPLC to give the desired compound 1, 6-((4-(4-acetylpiperazin-1-yl)phenylamino)-4-(benzylamino)pyridazine-3-carboxamide, 5.

Alternately, a mixture of 5-10 (90 mg), 1-(4-(4-aminophenyl)piperazin-1-yl)ethanone (78 mg, 0.356 mmol) and $pTsOH.H_2O$ (18 mg, 0.094 mmol) in n-BuOH (3 ml) was stirred at 100° C. for 2 hr. The reaction mixture was concentrated and purified by RP-HPLC to give desired compound 1, 6-((4-(4-acetylpiperazin-1-yl)phenylamino)-4-(benzylamino)pyridazine-3-carboxamide, 5. $MH^+$=446.4, UV 200.4, 249.2.

Example 2

Synthesis of 4-(cyclobutylamino)-6-((4-morpholinophenyl)amino)pyridazine-3-carboxamide (Compound 6)

Figure 6:
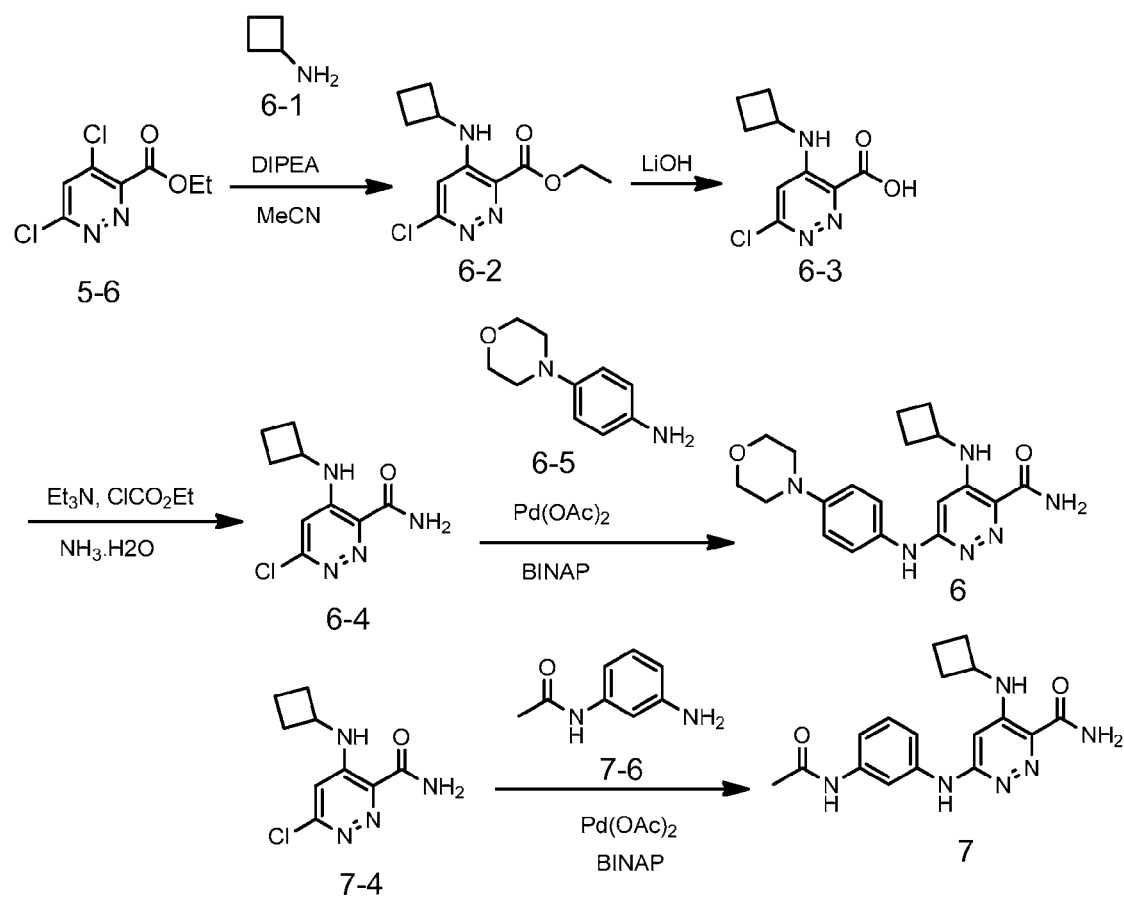
FIG. 6 shows a synthetic route for the preparation of 4-(cyclobutylamino)-6-((4-morpholinophenyl)amino) pyridazine-3-carboxamide and 6-((3-acetamidophenyl) amino)-4-(cyclobutylamino)pyridazine-3-carboxamide.

Compound 6 was synthesize according to FIG. 6.

To compound 5-6 (220 mg, 1 mmol) in acetonitrile (2 ml) was added cyclobutamine (102 μL, 1.2 mmol) and DIEA (213 μL, 1.2 mmol) and the reaction mixture stirred at room temperature for 3 hr. After work up and extraction with ethyl acetate the crude compound 6-2 was isolated. To the THF solution of crude 6-2 added LiOH (84 mg) and stirred for 4 hr. The reaction mixture was acidified and extracted the desired product 6-3 as white solid.

To the 6-3 (220 mg, 0.9 mmol) in THF (2 ml) at 0° C. was added triethylamine (143 μL, 1.02 mmol) and ethyl chloroformate (106 μL, 1.12 mmol). The mixture was stirred at room temperature for 15 mins followed by addition of concentrated aqueous ammonia (0.5 mL) after stirring for 15 min added water and the precipitate was collected by filtration to give desired compound 6-4.

A mixture of 6-4 (25 mg, 0.22 mmol), 4-morpholinaniline (58 mg, 0.265 mmol), $Cs_2CO_3$ (215 mg, 0.66 mmol), BINAP (26 mg, 0.044 mmol) and $Pd(OAc)_2$ (10 mg, 0.044 mmol) in dioxane (2 ml) was degassed with argon and then heated at 80° C. overnight. The reaction mixture was concentrated and then purified by RP-HPLC to give desired compound 6; MH+=369.5, UV 261.7, Rt: 1.63 min.

Example 3

Synthesis of 6-((3-acetamidophenyl)amino)-4-(cyclobutylamino)pyridazine-3-carboxamide (Compound 7)

Compound 7 was synthesized according to FIG. 6. Compound 7 was synthesized as described in for compound 6 where N-(3-aminophenyl)acetamide was added in place of 4-morpholinaniline to afford compound 7: MH+=341.5, UV 249.9, Rt: 1.55 min.

Example 4

Synthesis of Intermediates with Various Aliphatic Amines

Figure 7:
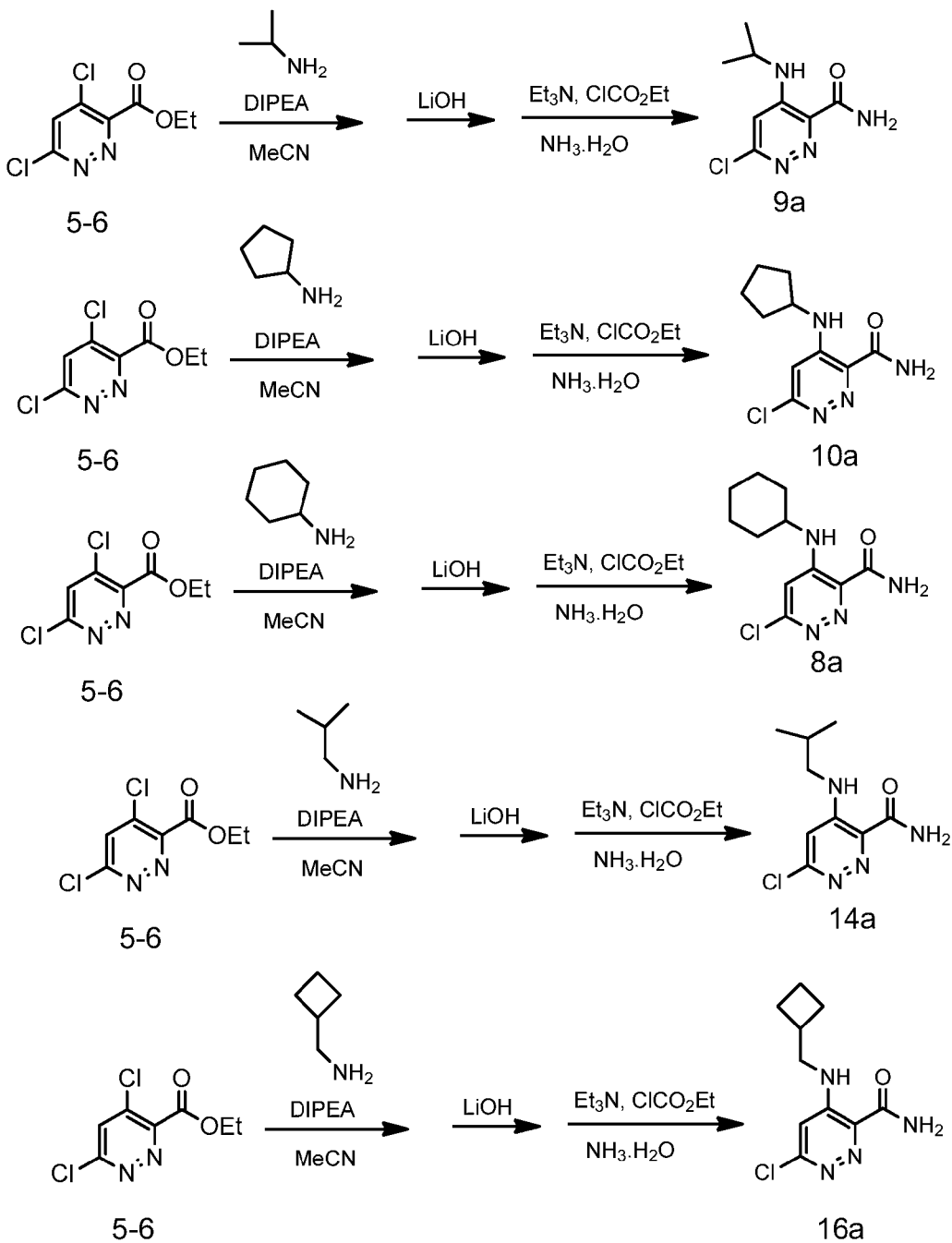
FIG. 7 shows a synthetic route for the preparation of various pyridazine intermediate compounds.

Various compound intermediates were synthesized from common material 5-6 according to FIG. 7. The intermediate 5-6 (1 equivalent) was treated with various aliphatic amines (1.2 equivalent) and DIEA (1.2 equivalent) in acetonitrile at room temperature. The intermediate in THF was then treated with LiOH (2 equivalent) to form the acid. To acid (1 equivalent) in THF was added triethylamine (1.05 equivalent) followed by ethyl chloroformate, ClCO2Et (1.15 equivalent) and the reaction mixture was stirred for 15 minutes. To this mixture was added concentrated aqueous ammonia (3 equivalent) and water to give precipitates of the desired amide intermediates, 8a, 9a, 10a, 14a and 16a. Synthesis of intermediate 10a, 8a, 14a and 16a was achieved as described for Compound 6.

Example 5

Synthesis of 6-((4-(4-acetylpiperazin-1-yl)phenyl) amino)-4-(cyclohexylamino)pyridazine-3-carboxamide (Compound 8) and 4-(cyclohexylamino)-6-((4-(piperazin-1-yl)phenyl)amino)pyridazine-3-carboxamide (Compound 11)

Figure 8:
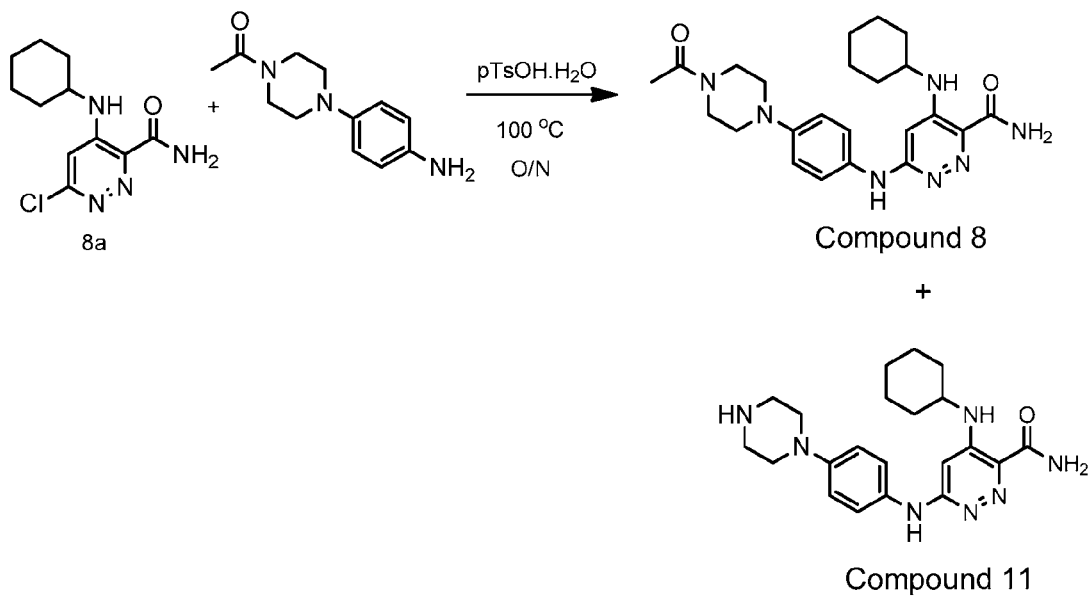
FIG. 8 shows a synthetic route for the preparation of 6-((4-(4-acetylpiperazin-1-yl)phenyl)amino)-4-(cyclohexylamino)pyridazine-3-carboxamide and 4-(cyclohexylamino)-6-((4-(piperazin-1-yl)phenyl)amino)pyridazine-3-carboxamide.

Compounds 8 and 11 were synthesized as shown in FIG. 8. A mixture of 8a (30 mg, 0.107 mmol), 1-(4-(4-aminophenyl)piperazin-1-yl)ethanone (28 mg, 0.128 mmol) and pTsOH.H$_2$O (24 mg, 0.12 mmol) in NMP (1 ml) was stirred at 100° C. for 2 hr. The reaction mixture was concentrated and purified by RP-HPLC to give compound 8 (4, 6-((4-(4-acetylpiperazin-1-yl)phenylamino)-4-(cyclohexylamino) pyridazine-3-carboxamide); MH+=438.7, UV 253.6, Rt=1.87 min and compound 11 (4-(cyclohexylamino)-6-((4-(piperazin-1-yl)phenyl)amino)pyridazine-3-carboxamide); MH+=396.6, UV 252.3, Rt=1.52 min The Compounds 9, 10, 12, 13, 14, 15, 16, and 17 were synthesized from the intermediates 9a, 10a, 14a, and 16a according to FIG. 9 and experimental description for Compounds 8 & 11.

Example 6

Synthesis of 6-((4-(4-acetylpiperazin-1-yl)phenyl) amino)-4-((2-fluorobenzyl)amino)pyridazine-3-carboxamide (Compound 18)

Figure 9:
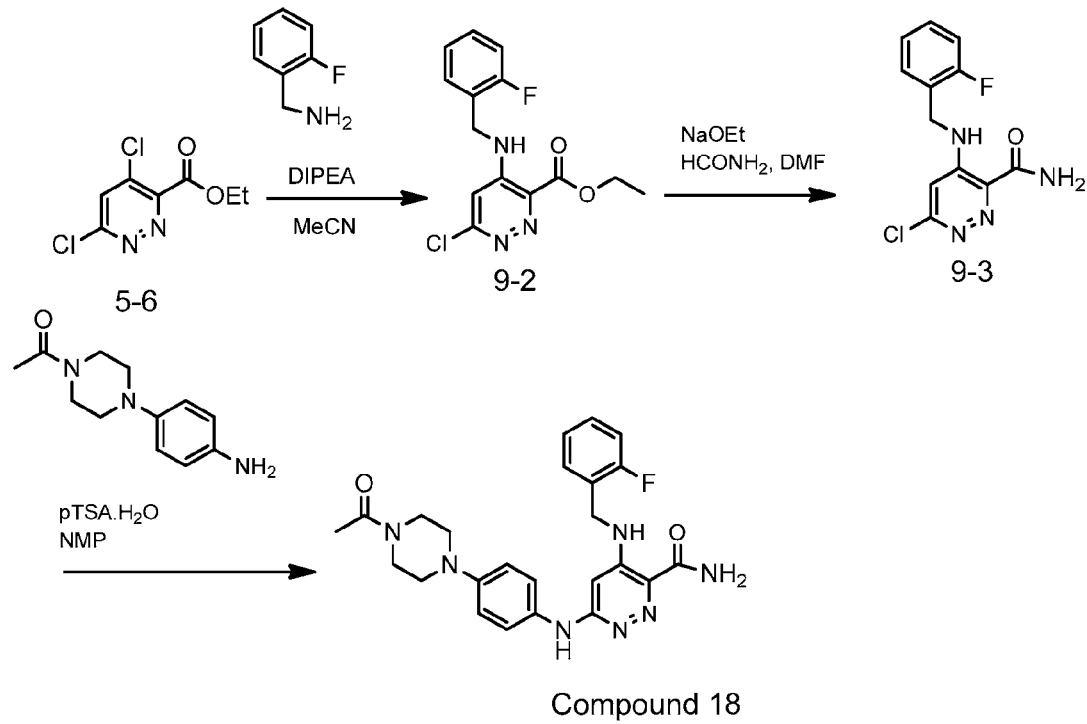
FIG. 9 shows a synthetic route for the preparation of 6-((4-(4-acetylpiperazin-1-yl)phenyl)amino)-4-((2-fluorobenzyl)amino)pyridazine-3-carboxamide.

Compound 18 was synthesized according to FIG. 9.
To compound 5-6 (170 mg, 0.77 mmol) in acetonitrile (2 ml) was added 2-fluoro benzylamine (106 mg, 0.85 mmol) and DIEA (151 µL, 0.85 mmol) and the reaction mixture was stirred at room temperature for 3 hr. After work up and extraction with ethyl acetate the compound 9-2 was isolated.
To 9-2 (205 mg, 0.66 mmol) in DMF (1.5 ml) was added formamide (267 mg, 5.94 mmol, 9 equivalent) and an ethanolic solution of sodium ethoxide (21% solution, 366 µL, 0.99 mmol, 1.5 equivalent). The mixture was stirred at 65° C. for 30 minutes during which time reaction was complete. To the reaction mixture added water and the desired amide 9-3 was precipitated. This was isolated by filtration to give 170 mg of intermediate 9-3.
A mixture of 9-3 (56 mg, 0.2 mmol), 1-(4-(4-aminophenyl)piperazin-1-yl)ethanone (48 mg, 0.22 mmol, 1.1 equivalent) and pTsOH.H$_2$O (57 mg, 0.3 mmol, 1.5 equiv) in NMP (1 ml) was stirred at 100° C. for 2 hr. The reaction mixture was concentrated and purified by RP-HPLC to give compound 18 (6-((4-(4-acetylpiperazin-1-yl)phenyl)amino)-4-((2-fluorobenzyl)amino)pyridazine-3-carboxamide); MH+=464.3, UV 246.3, Rt: 1.76 min.
The Compounds 19, 20, 21, 23, 25-66, 85, 86, 90, 96, 107, and 110 were synthesized following the FIG. 9 and the experimental description for Compound 18.

Example 7

Synthesis of Additional Pyridazine Compounds (Compounds 68-72)

Figure 10:
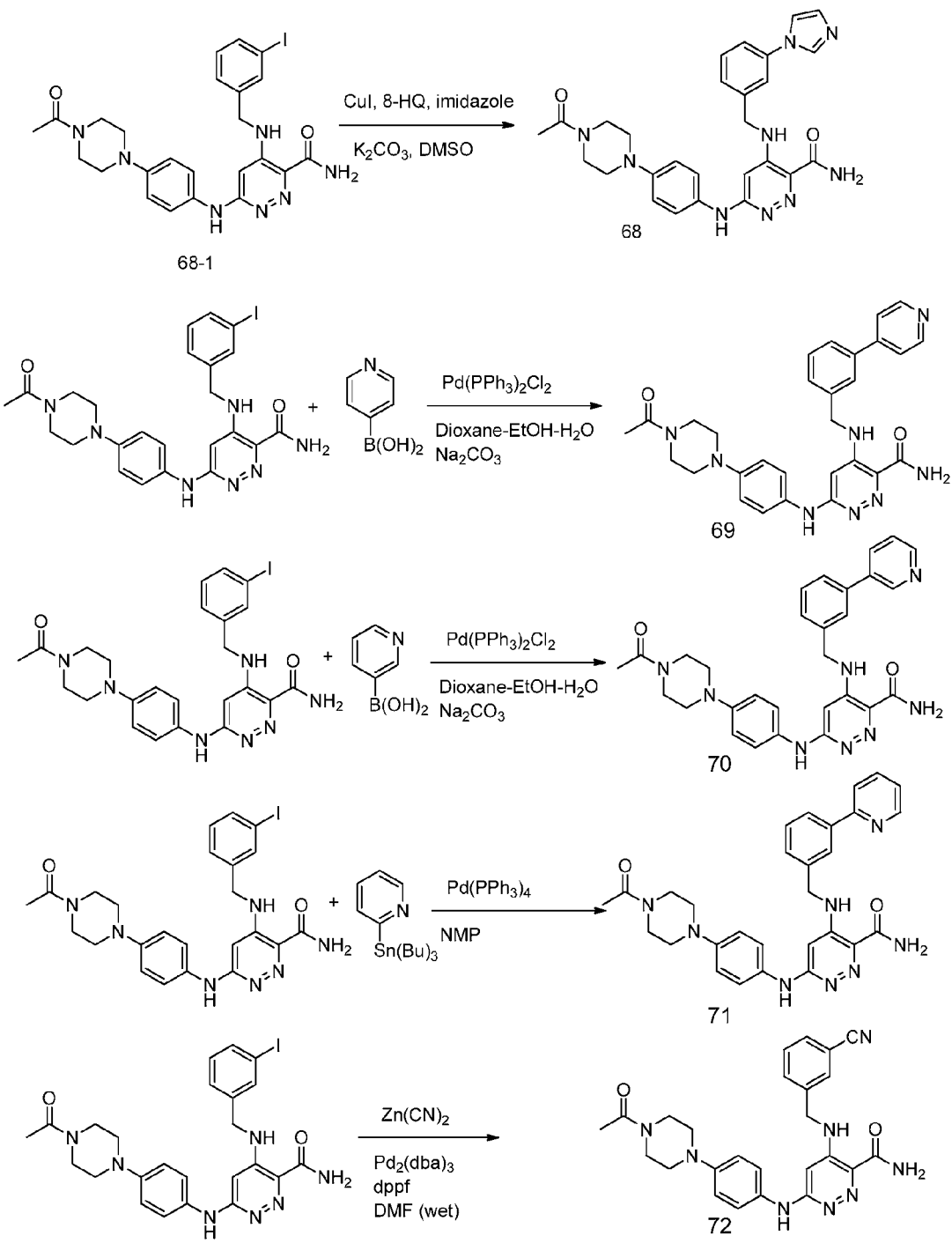
FIG. 10 shows synthetic routes for the preparation of various pyridazine compounds.
Figure 11:
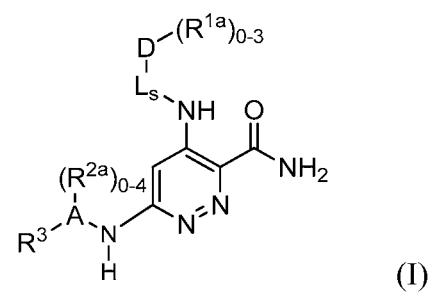
FIG. 11 shows the molecular formula of certain compounds of the invention, as described below.

The compound 68-1 was synthesized using as described for compound 18 and shown in FIG. 9 using compound 5-6 (170 mg, 0.77 mmol) in acetonitrile (2 ml) and 3-iodo benzylamine (106 mg, 0.85 mmol) and DIEA (151 µL, 0.85 mmol).
To the degassed DMSO (1 ml) solution of 68-1 (70 mg, 0.122 mmol) was added 8-hydroxyquinoline (12 mg, 0.08 mmol, 0.66 equiv), copper iodide (12 mg, 0.061 mmol, 0.5 equiv), K$_2$CO$_3$ (34 mg, 0.244 mmol, 2 equiv), imidazole (16 mg, 0.244 mmol, 2 equiv) and heated at 125° C. for 6 hr. After workup the crude residue was purified by RP-HPLC to afford desired compound 68. MH+=512.3, UV 242.8, Rt: 1.34 min.
Compound 69 was synthesized as shown in FIG. 10. To the compound 68-1 (70 mg, 0.122 mmol, 1 equiv) in dioxane (1 ml) added PdCl$_2$(PPh$_3$)Cl$_2$ (17 mg, 0.024 mmol, 0.2 equiv), Na$_2$CO$_3$ (1M aqueous solution, 0.4 ml, 0.366 mmol, 3 equiv), pyridyl-4-boronic acid (22 mg, 0.183 mmol, 1.5 equiv) and heated at 100° C. for 3 hr. After work up with water, the crude residue was purified by RP-HPLC to afford the desired compound 69. MH+=523.3, UV 248.7, 274.8, Rt: 1.40 min.
Compound 70 was synthesized using the similar process as Compound 69 using pyridyl-3-boronic acid. MH+=523.3, UV 251.1, 274.8, Rt: 1.42 min.
Compound 71 was synthesized as shown in FIG. 10. To the compound 68-1 (70 mg, 0.122 mmol, 1 equiv) in NMP (1 ml) were added pyridyl-2-tributylstannane (90 mg, 0.244 mmol, 2 equiv) and tetrakis(triphenylphoshine)palladium (28 mg, 0.0244 mmol, 0.2 equiv). The mixture was heated at 95° C. for 5 hr. The desired compound 71 was isolated by RP-HPLC as a white solid. MH+=523.4, UV 244.0, 290.2, Rt: 1.439 min.

Compound 72 was synthesized as shown in FIG. 10. To the compound 68-1 (70 mg, 0.122 mmol, 1 equiv) in wet DMF (1 ml) were added zinc dicyanide (14 mg, 0.122 mmol, 1 equiv), Pd$_2$(dba)$_3$ (11 mg, 0.0122 mmol, 0.1 equiv), and dppf (13.5 mg, 0.0244 mmol, 0.2 equiv). The mixture was heated at 95° C. for 5 hr. The desired compound 68 was isolated by RP-HPLC as white solid. MH+=471.3, UV 231.0, Rt: 1.63 min.

Example 8

Purified Kinase Assay

JAK and TYK2 tyrosine phosphorylation activity is measured using the Z'-LYTE™ Technology developed by Invitrogen Corporation (Carlsbad, Calif.). For JAK1, JAK2 and JAK3 the Z'-LYTE™ Kinase Assay Kit-Tyr6 Peptide (part number PV4122) was used. For TYK2 the Z'-LYTE™ Kinase Assay Kit-Tyr6 Peptide (part number PV3192) was used. The Z'-LYTE™ biochemical assay employs a fluorescence resonance energy transfer (FRET) coupled-enzyme format and is based on the differential sensitivity of phosphorylated and non-phosphorylated peptides to proteolytic cleavage. The assay uses a synthetic peptide substrate that is labeled with a donor fluorophore (coumarin) and an acceptor fluorophore (fluorescein) that make up a FRET pair. In the primary reaction (the Kinase Reaction), the kinase transfers the γ-phosphate of ATP to a single tyrosine residue on the substrate, while the presence of a kinase inhibitor in the primary reaction suppresses phosphorylation. In the secondary reaction (the Development Reaction), a site-specific protease (the Development Reagent) is added. The development buffer quenches the Kinase Reaction, while the protease recognizes and cleaves non-phosphorylated Z'-LYTE™ peptide substrate. Cleavage disrupts FRET between the donor and acceptor fluorophores on the non-phosphorylated substrate, while uncleaved, phosphorylated substrate maintains FRET.

To test the ability of candidate molecules to inhibit JAK tyrosine phosphorylation activity, molecules are reconstituted in 100% DMSO and serially diluted 1:10 in polypropylene v-bottom microtiter plates. The candidate molecules are then diluted 1:25 into kinase buffer and 2.5 μl transferred into duplicate wells of a 384 well low volume black microtiter assay plate (Corning, USA). The final DMSO concentration in the assay is 1%. The kinase reaction contains 2.5 μl of a candidate molecule, 5 μl of catalytic domain recombinant Kinase enzyme+Tyr peptide substrate (Invitrogen, CA) and ATP (Invitrogen, CA). The kinase reaction is allowed to proceed for 1 hour at room temperature. The protease reaction is initiated by the addition of Development Reagent (Invitrogen, CA). After 1 hour incubation at room temperature the fluorescence is measured using a FlexStation plate reader (Molecular Devices, Sunnyvale, Calif.). The reader settings used are as follows: Fluorescence mode, endpoint, top read, excitation 400 nm, emission 445 nm and 520 nm, Auto Cutoff 435 nm and 515 nm, PMT sensitivity high, 6 reads per well Inhibition of JAK activity is calculated as the percent phosphorylation of substrate in the presence of inhibitor compared to the percent phosphorylation of substrate in the absence of inhibitor. IC50's were derived using Xlfit 4.3 (IDBS, UK), 4 parameter logistic model 205: $Y=(A+((B-A)/(1+((C/x)^{\wedge}D))))$.

In Table 1 below, activity in the JAK assays is provided as follows: +++++=IC$_{50}$<0.0010 μM; ++++=0.0010 μM<IC$_{50}$<0.010 μM; +++=0.010 μM<IC$_{50}$<0.10 μM; ++=0.10 μM<IC$_{50}$<1.0 μM; +=IC$_{50}$>1 μM.

TABLE 1

| | JAK inhibition activity of compound of the invention | | | | | | |
|---|---|---|---|---|---|---|---|
| No. | Structure | MW (g/mol) | MS | JAK1 IC50 (μM) | JAK2 IC50 (μM) | JAK3 IC50 (μM) | Tyk2 IC50 (μM) |
| 5 | 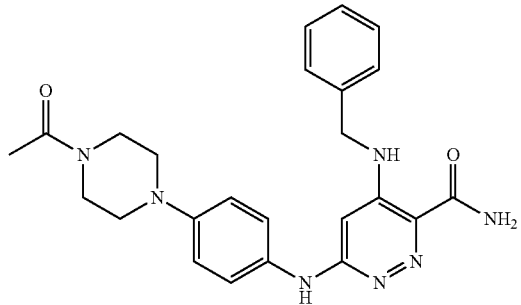 [SMILES: CC(=O)N1CCN(c2ccc(Nc3cc(NCc4ccccc4)c(C(N)=O)nn3)cc2)CC1] | 445.53 | 446.4 | + | ++ | +++ | ++ |
| 6 | 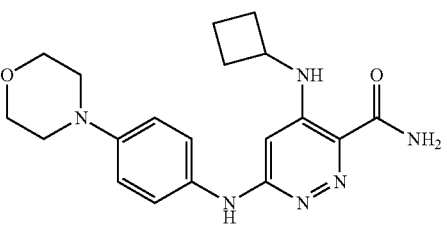 [SMILES: NC(=O)c1nnc(Nc2ccc(N3CCOCC3)cc2)cc1NC1CCC1] | 368.44 | 369.5 | + | ++ | ++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 7 | 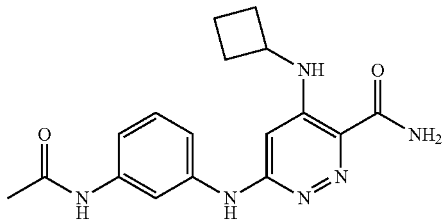 [SMILES: CC(=O)Nc1cccc(Nc2cc(NC3CCC3)c(C(N)=O)nn2)c1] | 340.39 | 341.5 | + | ++ | ++ | |
| 8 | 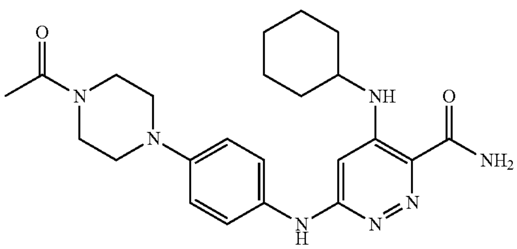 [SMILES: CC(=O)N1CCN(c2ccc(Nc3cc(NC4CCCCC4)c(C(N)=O)nn3)cc2)CC1] | 437.55 | 438.7 | ++ | ++ | +++ | |
| 9 | 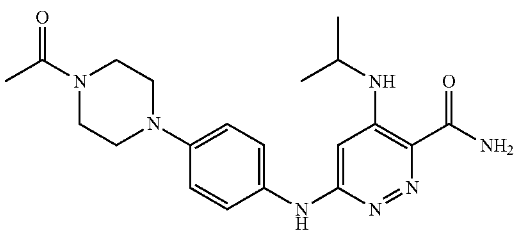 [SMILES: CC(=O)N1CCN(c2ccc(Nc3cc(NC(C)C)c(C(N)=O)nn3)cc2)CC1] | 397.48 | 398.6 | + | + | + | |
| 10 | 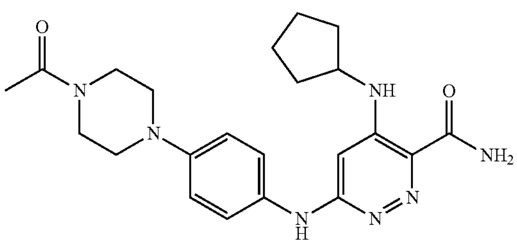 [SMILES: CC(=O)N1CCN(c2ccc(Nc3cc(NC4CCCC4)c(C(N)=O)nn3)cc2)CC1] | 423.52 | 424.6 | ++ | ++ | ++ | |
| 11 | 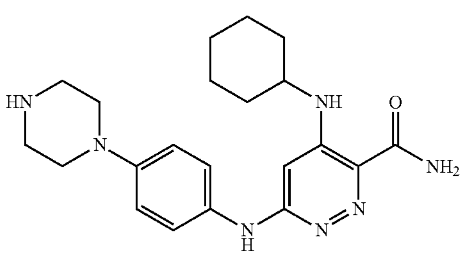 [SMILES: NC(=O)c1nnc(Nc2ccc(N3CCNCC3)cc2)cc1NC1CCCCC1] | 395.51 | 396.6 | + | ++ | ++ | |
| 12 | 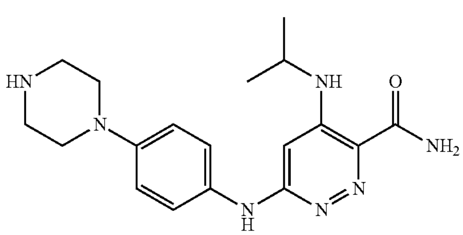 [SMILES: CC(C)Nc1cc(Nc2ccc(N3CCNCC3)cc2)nnc1C(N)=O] | 355.45 | 356.6 | + | + | + | |

TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 13 | 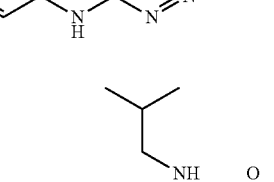 | 381.48 | 382.6 | + | ++ | ++ | |
| 14 | 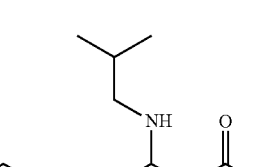 | 411.51 | 412.5 | + | ++ | ++ | |
| 15 | 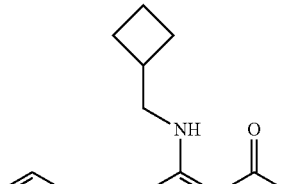 | 369.47 | 370.4 | + | + | ++ | |
| 16 | 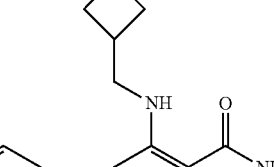 | 423.52 | 424.5 | + | ++ | +++ | |
| 17 | 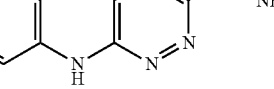 | 381.48 | 382.4 | + | + | ++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 18 | 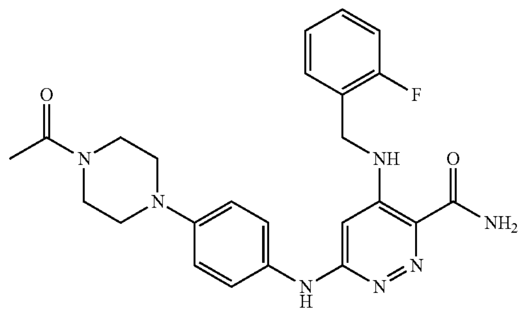 [SMILES: CC(=O)N1CCN(c2ccc(Nc3cc(NCc4ccccc4F)c(C(N)=O)nn3)cc2)CC1] | 463.52 | 464.3 | ++ | ++ | ++++ | ++ |
| 19 | 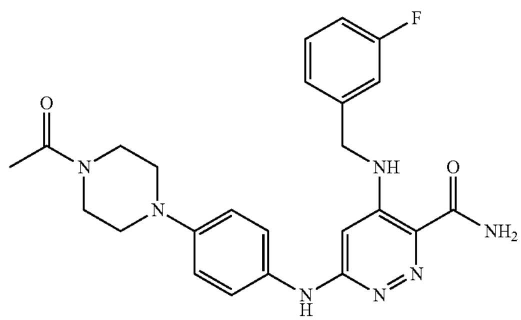 [SMILES: CC(=O)N1CCN(c2ccc(Nc3cc(NCc4cccc(F)c4)c(C(N)=O)nn3)cc2)CC1] | 463.52 | 464.3 | + | ++ | ++++ | ++ |
| 20 | 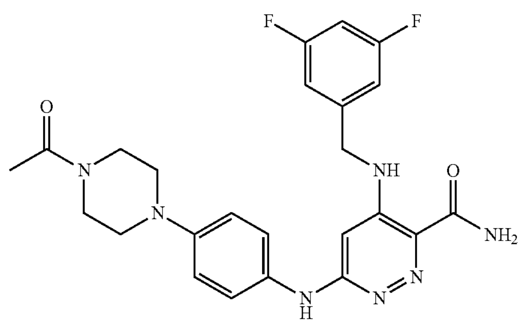 [SMILES: CC(=O)N1CCN(c2ccc(Nc3cc(NCc4cc(F)cc(F)c4)c(C(N)=O)nn3)cc2)CC1] | 481.51 | 482.3 | ++ | +++ | ++++ | ++ |
| 21 | 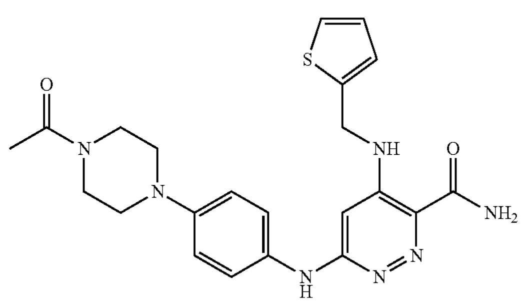 [SMILES: CC(=O)N1CCN(c2ccc(Nc3cc(NCc4cccs4)c(C(N)=O)nn3)cc2)CC1] | 451.55 | 452.3 | + | ++ | +++ | ++ |

TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 22 | 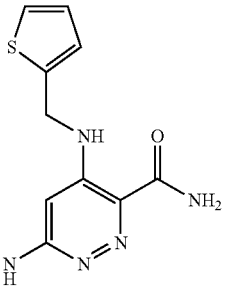 | 409.52 | 410.2 | + | + | +++ | |
| 23 | 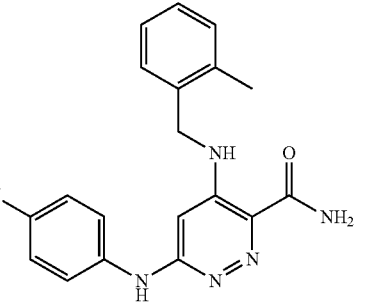 | 459.55 | 460.4 | ++ | ++ | ++++ | ++ |
| 24 | 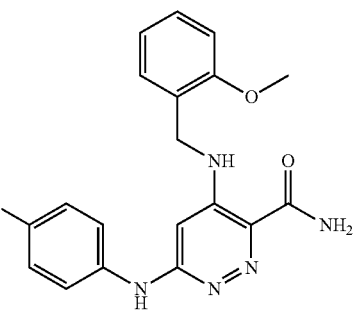 | 475.55 | 476.4 | ++ | +++ | +++ | |
| 25 | 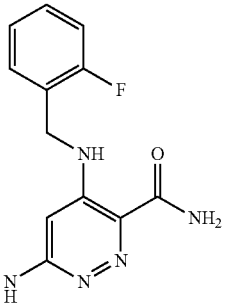 | 476.56 | 477.3 | + | + | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 26 | 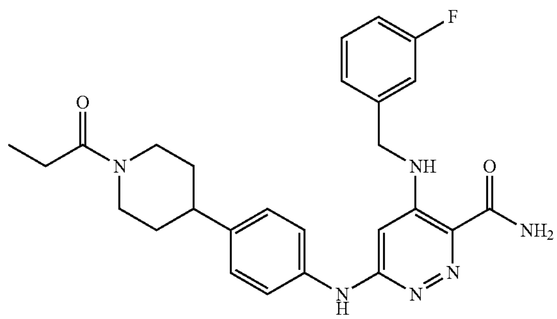 [SMILES: CCC(=O)N1CCC(c2ccc(Nc3cc(NCc4cccc(F)c4)c(C(N)=O)nn3)cc2)CC1] | 476.56 | 477.3 | + | + | +++ | |
| 27 | 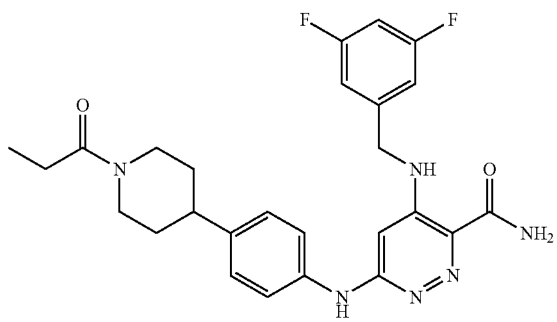 [SMILES: CCC(=O)N1CCC(c2ccc(Nc3cc(NCc4cc(F)cc(F)c4)c(C(N)=O)nn3)cc2)CC1] | 494.55 | 495.3 | + | + | +++ | |
| 28 | 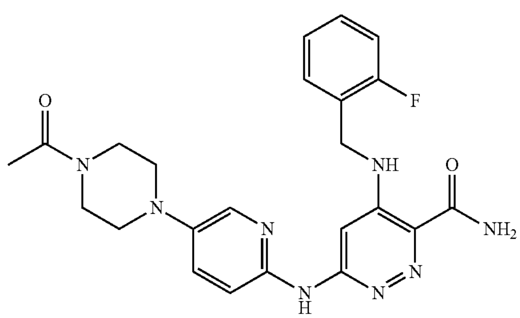 [SMILES: CC(=O)N1CCN(c2ccc(Nc3cc(NCc4ccccc4F)c(C(N)=O)nn3)nc2)CC1] | 464.51 | 465.3 | ++ | +++ | ++++ | |
| 29 | 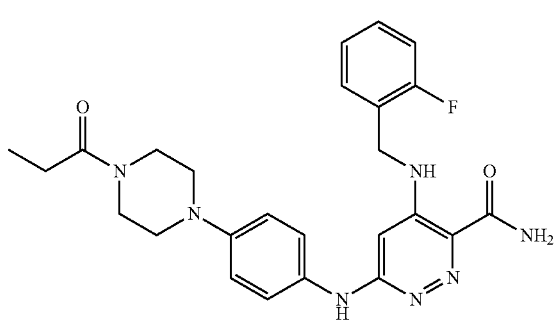 [SMILES: CCC(=O)N1CCN(c2ccc(Nc3cc(NCc4ccccc4F)c(C(N)=O)nn3)cc2)CC1] | 477.54 | 478.3 | + | ++ | +++ | ++ |

TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 30 | 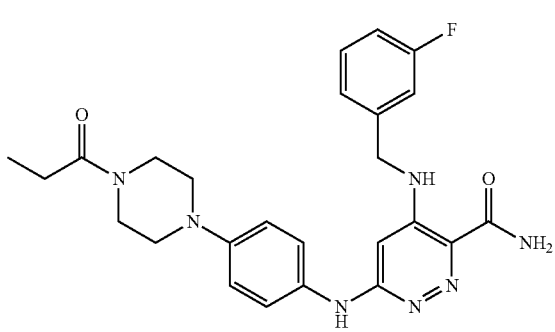 [SMILES: CCC(=O)N1CCN(c2ccc(Nc3cc(NCc4cccc(F)c4)c(C(N)=O)nn3)cc2)CC1] | 477.54 | 478.3 | + | ++ | +++ | |
| 31 | 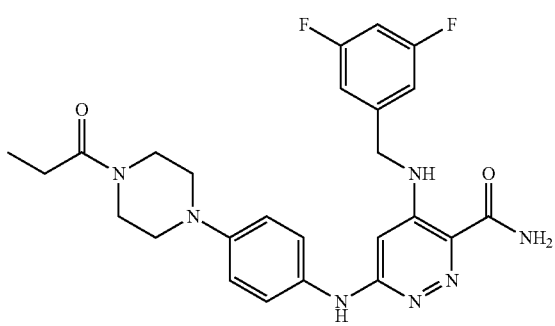 [SMILES: CCC(=O)N1CCN(c2ccc(Nc3cc(NCc4cc(F)cc(F)c4)c(C(N)=O)nn3)cc2)CC1] | 495.53 | 496.3 | + | ++ | ++++ | |
| 32 | 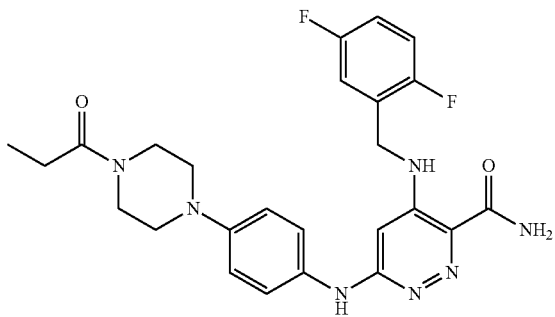 [SMILES: CCC(=O)N1CCN(c2ccc(Nc3cc(NCc4cc(F)ccc4F)c(C(N)=O)nn3)cc2)CC1] | 495.53 | 496.3 | + | +++ | ++++ | |
| 33 | 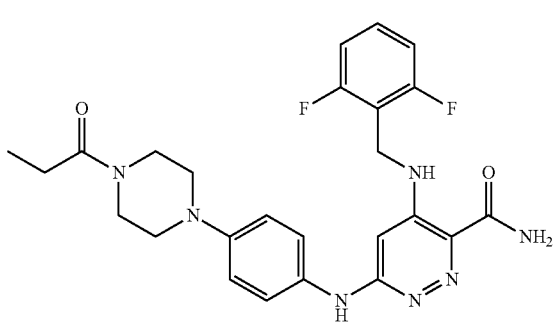 [SMILES: CCC(=O)N1CCN(c2ccc(Nc3cc(NCc4c(F)cccc4F)c(C(N)=O)nn3)cc2)CC1] | 495.53 | 496.3 | ++ | +++ | ++++ | +++ |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 34 | 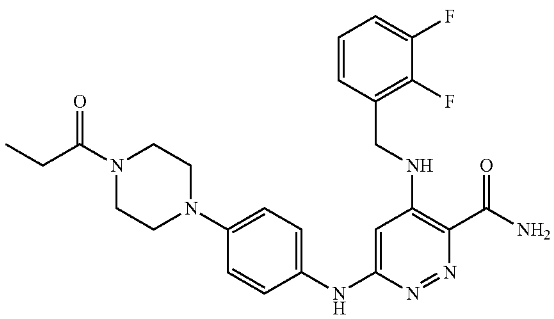 [SMILES: CCC(=O)N1CCN(c2ccc(Nc3cc(NCc4cccc(F)c4F)c(C(N)=O)nn3)cc2)CC1] | 495.53 | 496.4 | + | +++ | ++++ | |
| 35 | 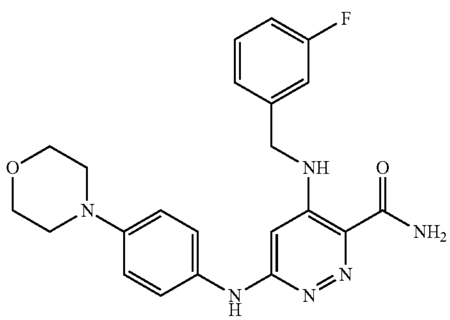 [SMILES: NC(=O)c1nnc(Nc2ccc(N3CCOCC3)cc2)cc1NCc1cccc(F)c1] | 422.46 | 423.3 | + | ++ | +++ | |
| 36 | 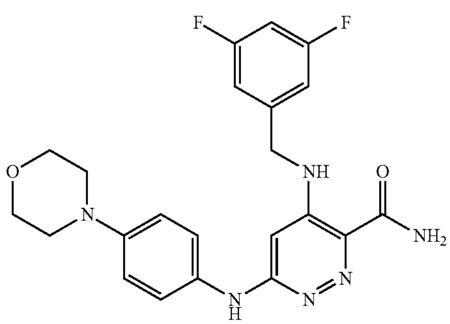 [SMILES: NC(=O)c1nnc(Nc2ccc(N3CCOCC3)cc2)cc1NCc1cc(F)cc(F)c1] | 440.45 | 441.1 | + | ++ | +++ | |
| 37 | 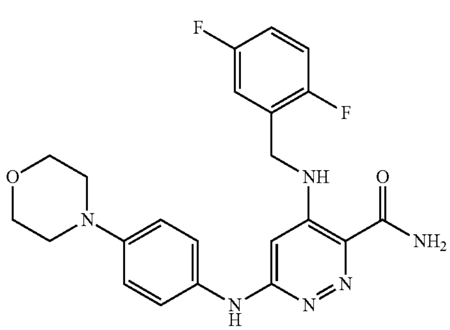 [SMILES: NC(=O)c1nnc(Nc2ccc(N3CCOCC3)cc2)cc1NCc1cc(F)ccc1F] | 440.45 | 441.3 | + | +++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 38 | 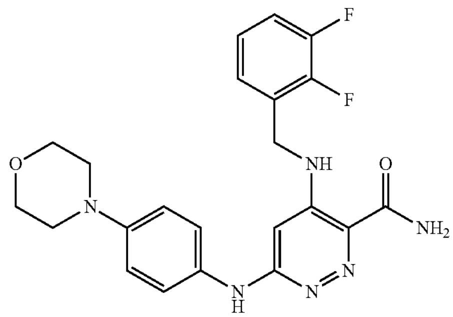 [SMILES: NC(=O)c1nnc(Nc2ccc(N3CCOCC3)cc2)cc1NCc1cccc(F)c1F] | 440.45 | 441.3 | + | ++ | +++ | |
| 39 | 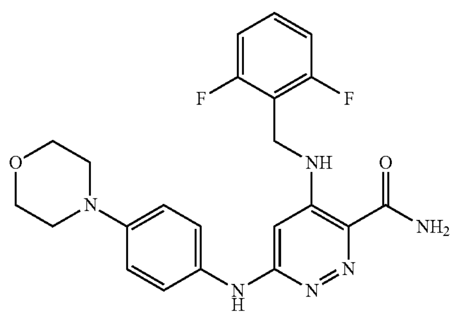 [SMILES: NC(=O)c1nnc(Nc2ccc(N3CCOCC3)cc2)cc1NCc1c(F)cccc1F] | 440.45 | 441.3 | ++ | +++ | ++++ | |
| 40 | 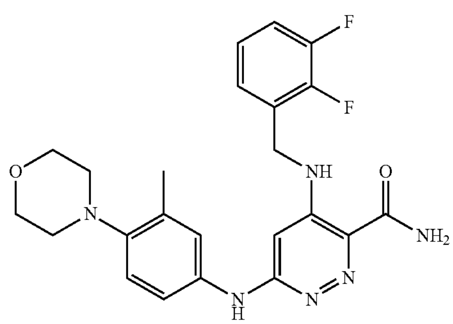 [SMILES: Cc1cc(Nc2cc(NCc3cccc(F)c3F)c(C(N)=O)nn2)ccc1N1CCOCC1] | 454.48 | 455.3 | + | + | +++ | |
| 41 | 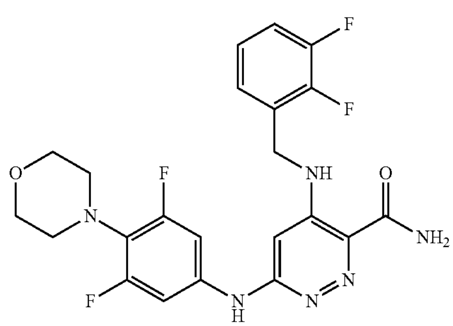 [SMILES: NC(=O)c1nnc(Nc2cc(F)c(N3CCOCC3)c(F)c2)cc1NCc1cccc(F)c1F] | 476.43 | 477.3 | + | + | + | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 42 | 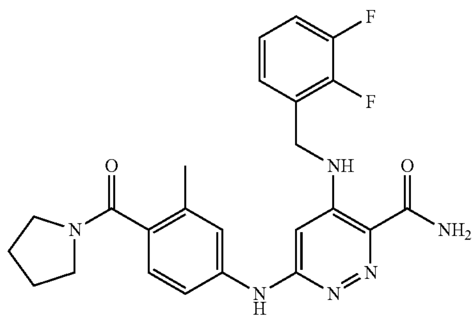 [SMILES: Cc1cc(Nc2cc(NCc3cccc(F)c3F)c(C(N)=O)nn2)ccc1C(=O)N1CCCC1] | 466.49 | 467.3 | ++ | +++ | ++++ | ++ |
| 43 | 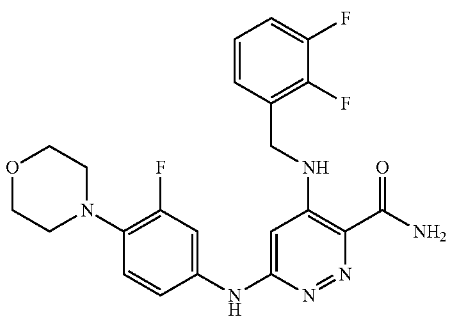 [SMILES: NC(=O)c1nnc(Nc2ccc(N3CCOCC3)c(F)c2)cc1NCc1cccc(F)c1F] | 458.44 | 459.3 | + | + | +++ | |
| 44 | 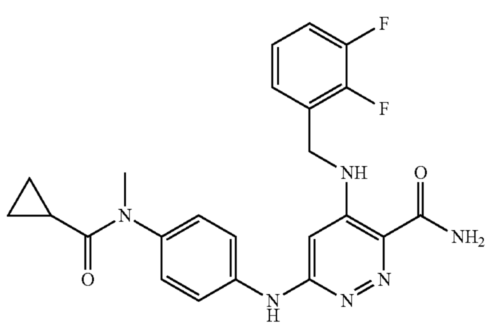 [SMILES: CN(C(=O)C1CC1)c1ccc(Nc2cc(NCc3cccc(F)c3F)c(C(N)=O)nn2)cc1] | 452.47 | 453.3 | + | + | +++ | |
| 45 | 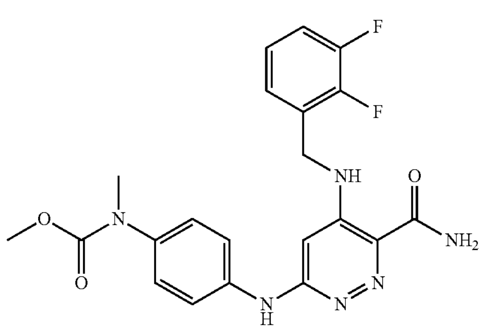 [SMILES: COC(=O)N(C)c1ccc(Nc2cc(NCc3cccc(F)c3F)c(C(N)=O)nn2)cc1] | 442.43 | 443.3 | + | + | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 46 | 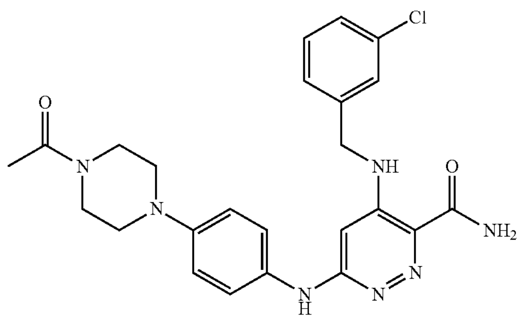 [SMILES: CC(=O)N1CCN(c2ccc(Nc3cc(NCc4cccc(Cl)c4)c(C(N)=O)nn3)cc2)CC1] | 479.97 | 480.2 | ++ | ++ | +++ | |
| 47 | 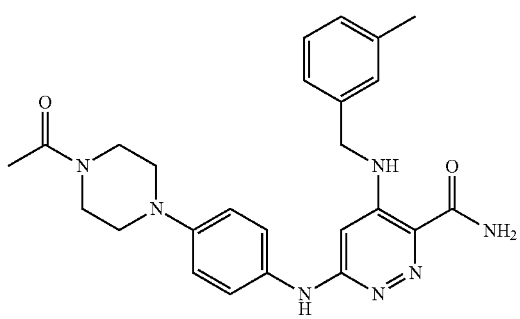 [SMILES: CC(=O)N1CCN(c2ccc(Nc3cc(NCc4cccc(C)c4)c(C(N)=O)nn3)cc2)CC1] | 459.55 | 460.3, 461.3 | + | ++ | +++ | |
| 48 | 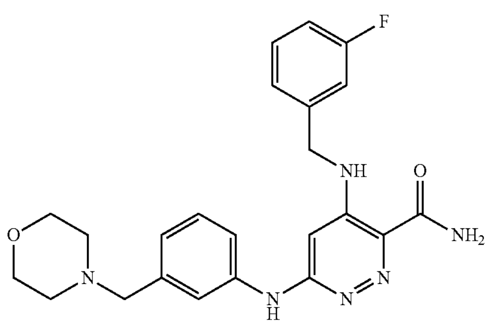 [SMILES: NC(=O)c1nnc(Nc2cccc(CN3CCOCC3)c2)cc1NCc1cccc(F)c1] | 436.49 | 437.3 | + | ++ | +++ | |
| 49 | 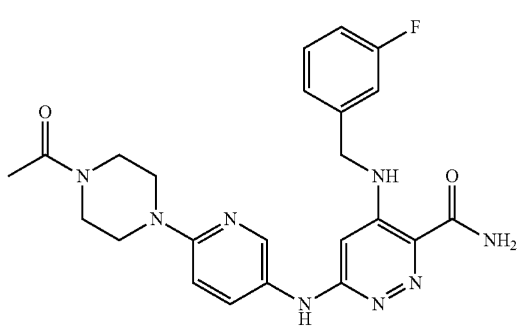 | 464.51 | 465.3 | + | + | ++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|-----|-----------|------------|-----|----------------|----------------|----------------|----------------|
| 50 | 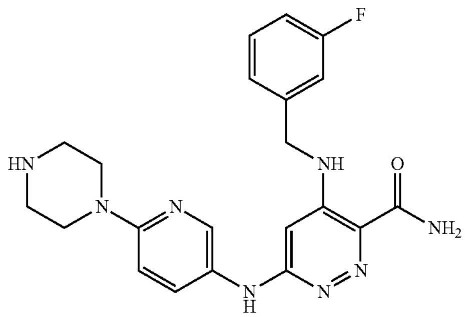 [SMILES: NC(=O)c1nnc(Nc2ccc(N3CCNCC3)nc2)cc1NCc1cccc(F)c1] | 422.47 | 423.3 | + | + | ++ | |
| 51 | 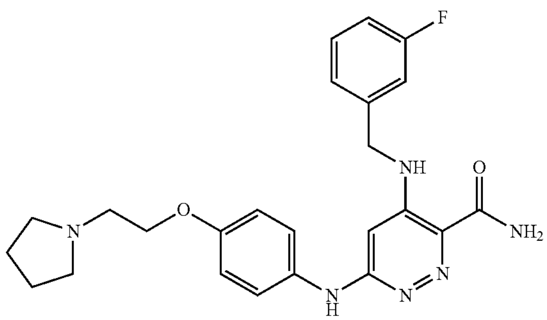 [SMILES: NC(=O)c1nnc(Nc2ccc(OCCN3CCCC3)cc2)cc1NCc1cccc(F)c1] | 450.52 | 451.3 | + | ++ | +++ | |
| 52 | 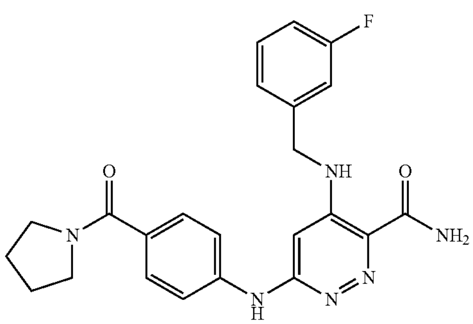 [SMILES: NC(=O)c1nnc(Nc2ccc(C(=O)N3CCCC3)cc2)cc1NCc1cccc(F)c1] | 434.48 | 435.3 | + | ++ | +++ | |
| 53 | 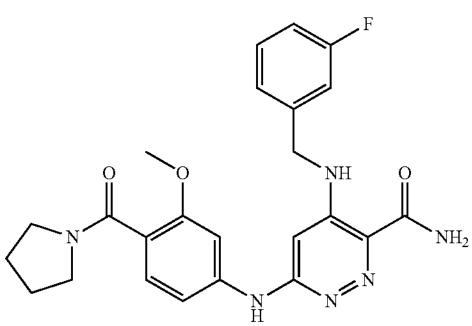 [SMILES: COc1cc(Nc2cc(NCc3cccc(F)c3)c(C(N)=O)nn2)ccc1C(=O)N1CCCC1] | 464.50 | 465.2 | + | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 54 | 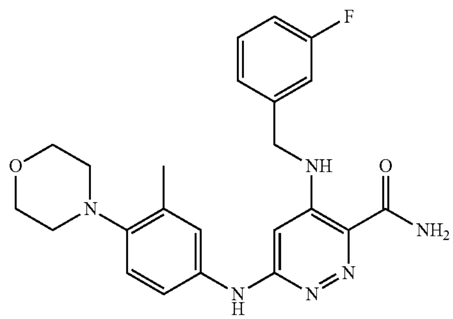 [SMILES: Cc1cc(Nc2cc(NCc3cccc(F)c3)c(C(N)=O)nn2)ccc1N1CCOCC1] | 436.49 | 437.4 | + | + | +++ | |
| 55 | 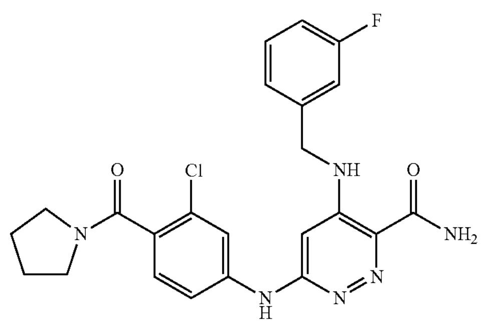 [SMILES: NC(=O)c1nnc(Nc2ccc(C(=O)N3CCCC3)c(Cl)c2)cc1NCc1cccc(F)c1] | 468.92 | 469.2, 471.2 | + | ++ | +++ | |
| 56 | 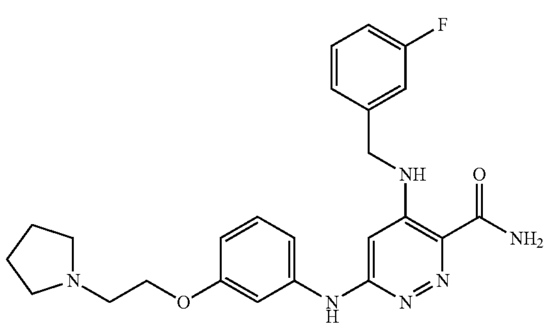 [SMILES: NC(=O)c1nnc(Nc2cccc(OCCN3CCCC3)c2)cc1NCc1cccc(F)c1] | 450.52 | 451.3 | + | ++ | +++ | + |
| 57 | 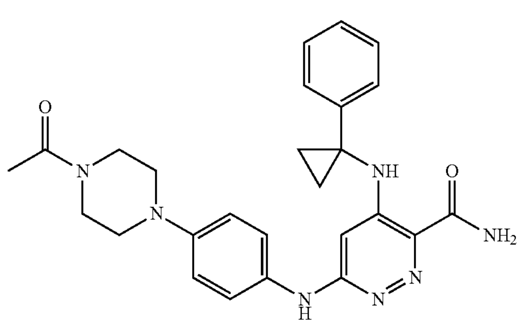 [SMILES: CC(=O)N1CCN(c2ccc(Nc3cc(NC4(c5ccccc5)CC4)c(C(N)=O)nn3)cc2)CC1] | 471.57 | 472.4 | + | + | +++ | + |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|-----|-----------|------------|-----|----------------|----------------|----------------|----------------|
| 58  | 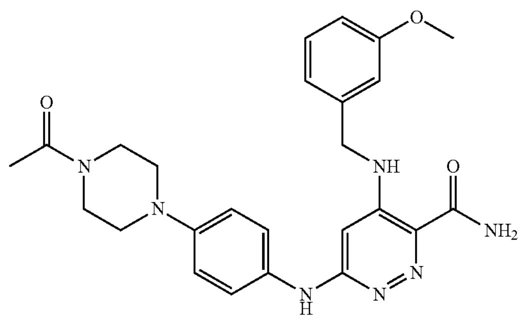 [SMILES: COc1cccc(CNc2cc(Nc3ccc(N4CCN(C(C)=O)CC4)cc3)nnc2C(N)=O)c1]          | 475.55     | 476.4 | +            | ++             | +++            | +              |
| 59  | 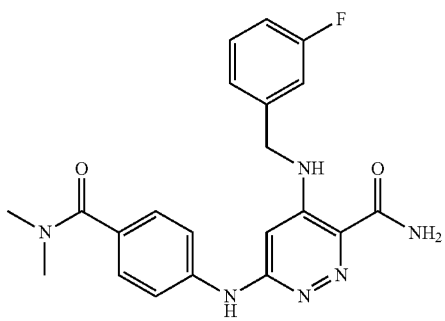 [SMILES: CN(C)C(=O)c1ccc(Nc2cc(NCc3cccc(F)c3)c(C(N)=O)nn2)cc1]          | 408.44     | 409.2 | +            | ++             | +++            | +              |
| 60  | 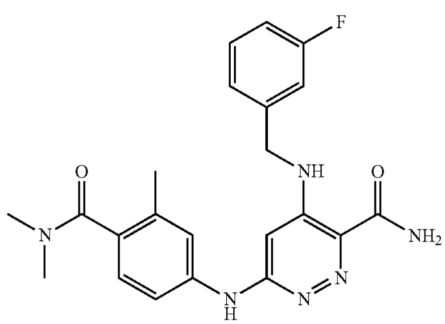 [SMILES: Cc1cc(Nc2cc(NCc3cccc(F)c3)c(C(N)=O)nn2)ccc1C(=O)N(C)C]          | 422.46     | 423.3 | +            | ++             | +++            | +              |
| 61  | 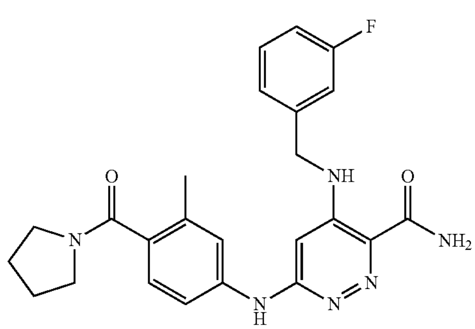 [SMILES: Cc1cc(Nc2cc(NCc3cccc(F)c3)c(C(N)=O)nn2)ccc1C(=O)N1CCCC1]          | 448.50     | 449.3 | +            | +++            | ++++           | ++             |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 62 | 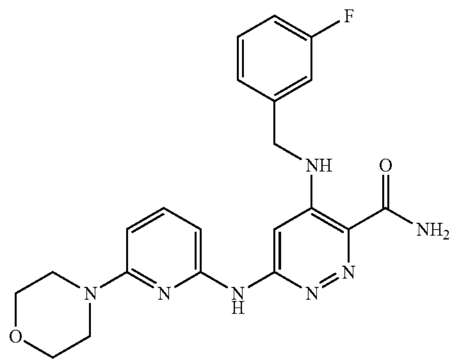 [SMILES: NC(=O)c1nnc(Nc2cccc(N3CCOCC3)n2)cc1NCc1cccc(F)c1] | 423.45 | 424.3 | + | + | + | |
| 63 | 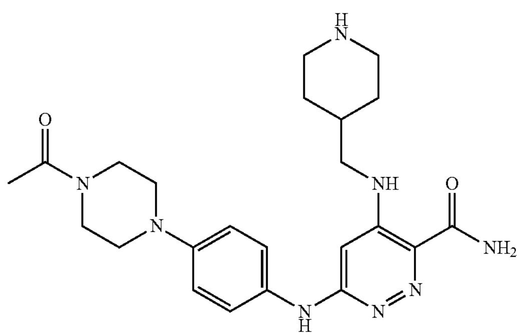 [SMILES: CC(=O)N1CCN(c2ccc(Nc3cc(NCC4CCNCC4)c(C(N)=O)nn3)cc2)CC1] | 452.56 | 453.3 | + | + | ++ | |
| 64 | 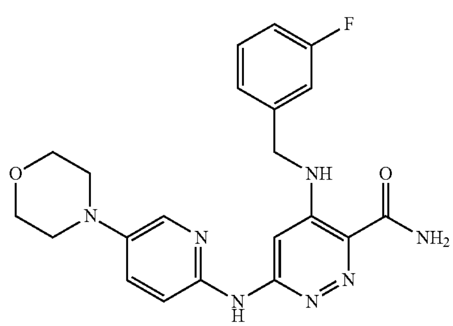 [SMILES: NC(=O)c1nnc(Nc2ccc(N3CCOCC3)cn2)cc1NCc1cccc(F)c1] | 423.45 | 424.3 | + | +++ | ++++ | |
| 65 | 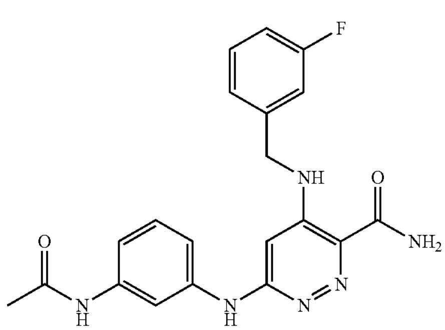 [SMILES: CC(=O)Nc1cccc(Nc2cc(NCc3cccc(F)c3)c(C(N)=O)nn2)c1] | 394.41 | 395.2 | + | ++ | +++ | ++ |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 66 | 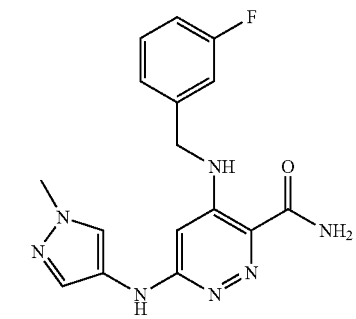 [SMILES: Cn1cc(Nc2cc(NCc3cccc(F)c3)c(C(N)=O)nn2)cn1] | 341.35 | 342.2 | + | ++ | +++ | + |
| 67 | 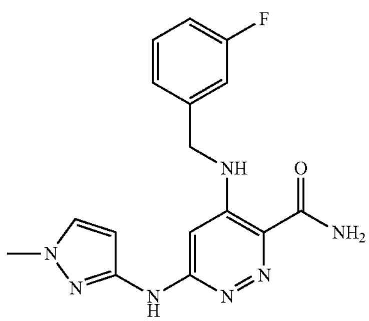 [SMILES: Cn1ccc(Nc2cc(NCc3cccc(F)c3)c(C(N)=O)nn2)n1] | 341.35 | 342.2 | + | ++ | +++ | |
| 68 | 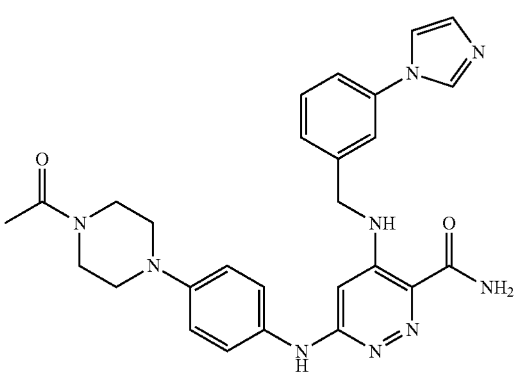 [SMILES: CC(=O)N1CCN(c2ccc(Nc3cc(NCc4cccc(-n5ccnc5)c4)c(C(N)=O)nn3)cc2)CC1] | 511.59 | 512.3 | + | + | +++ | |
| 69 | 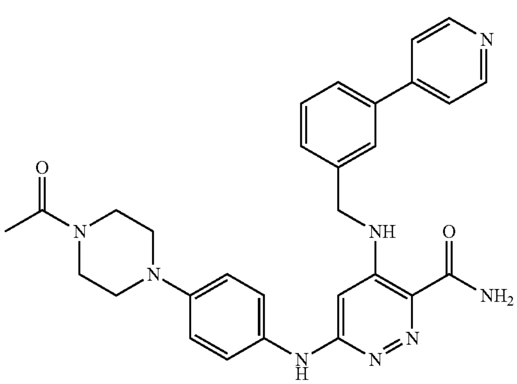 [SMILES: CC(=O)N1CCN(c2ccc(Nc3cc(NCc4cccc(-c5ccncc5)c4)c(C(N)=O)nn3)cc2)CC1] | 522.61 | 523.3 | + | + | +++ | |

TABLE 1-continued

| | | | | JAK1 IC50 (μM) | JAK2 IC50 (μM) | JAK3 IC50 (μM) | Tyk2 IC50 (μM) |
|---|---|---|---|---|---|---|---|
| No. | Structure | MW (g/mol) | MS | | | | |
| 70 | | 522.61 | 523.3 | + | ++ | +++ | |
| 71 | | 522.61 | 523.4 | + | + | ++ | |
| 72 | | 470.54 | 471.3 | + | ++ | +++ | |
| 73 | | 435.46 | 436.3 | ++ | +++ | ++++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 74 | 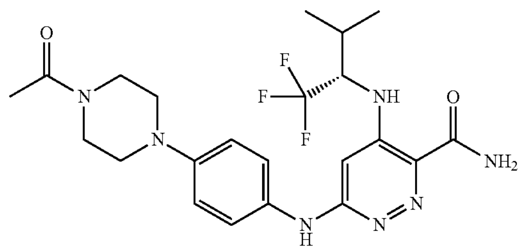 [SMILES: CC(=O)N1CCN(c2ccc(Nc3cc(N[C@@H](C(C)C)C(F)(F)F)c(C(N)=O)nn3)cc2)CC1] | 493.53 | 440.3 | +++ | +++ | +++ | |
| 75 | 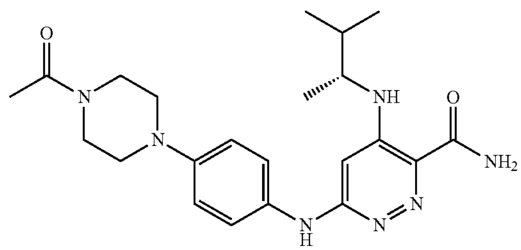 [SMILES: CC(=O)N1CCN(c2ccc(Nc3cc(N[C@H](C)C(C)C)c(C(N)=O)nn3)cc2)CC1] | 425.54 | 426.3 | ++ | +++ | +++ | |
| 76 | 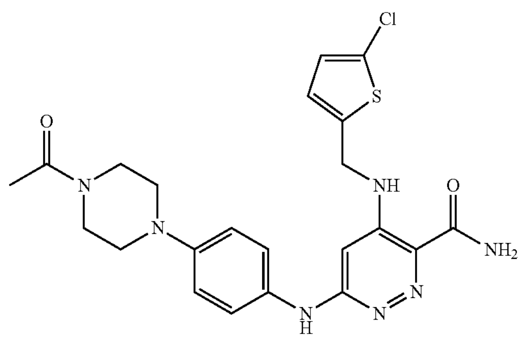 [SMILES: CC(=O)N1CCN(c2ccc(Nc3cc(NCc4ccc(Cl)s4)c(C(N)=O)nn3)cc2)CC1] | 486.00 | 486.2, 488.2 | + | + | +++ | |
| 77 | 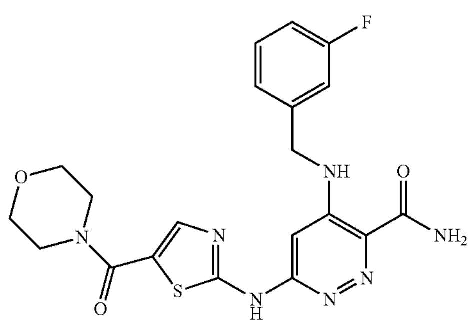 [SMILES: NC(=O)c1nnc(Nc2ncc(C(=O)N3CCOCC3)s2)cc1NCc1cccc(F)c1] | 457.49 | 458.2 | + | + | +++ | |
| 78 | 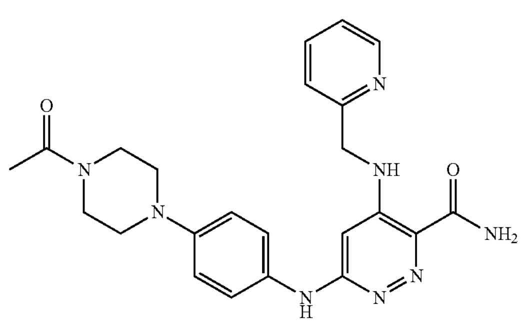 [SMILES: CC(=O)N1CCN(c2ccc(Nc3cc(NCc4ccccn4)c(C(N)=O)nn3)cc2)CC1] | 446.52 | 447.4 | + | + | ++ | |

TABLE 1-continued

JAK inhibition activity of compound of the invention

| No. | Structure | MW (g/mol) | MS | JAK1 IC50 (µM) | JAK2 IC50 (µM) | JAK3 IC50 (µM) | Tyk2 IC50 (µM) |
|---|---|---|---|---|---|---|---|
| 79 | 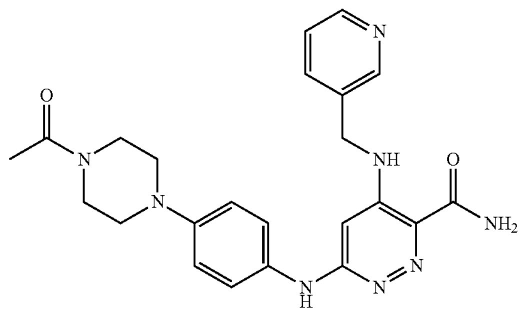 [SMILES: CC(=O)N1CCN(c2ccc(Nc3cc(NCc4cccnc4)c(C(N)=O)nn3)cc2)CC1] | 446.52 | 447.4 | + | + | ++ | |
| 80 | 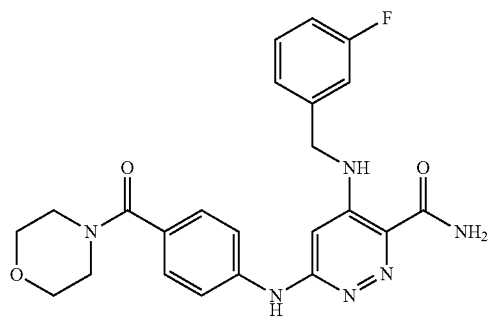 [SMILES: NC(=O)c1nnc(Nc2ccc(C(=O)N3CCOCC3)cc2)cc1NCc1cccc(F)c1] | 450.47 | 451.3 | + | ++ | +++ | |
| 81 | 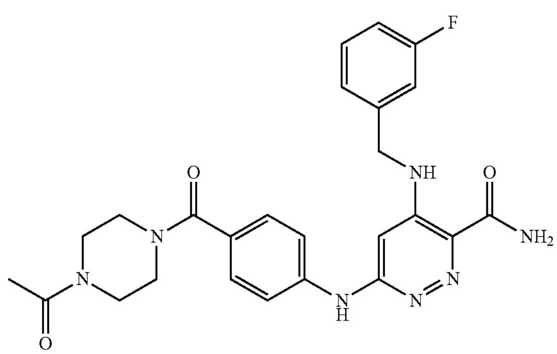 [SMILES: CC(=O)N1CCN(C(=O)c2ccc(Nc3cc(NCc4cccc(F)c4)c(C(N)=O)nn3)cc2)CC1] | 491.53 | 492.3 | + | ++ | +++ | |
| 82 | 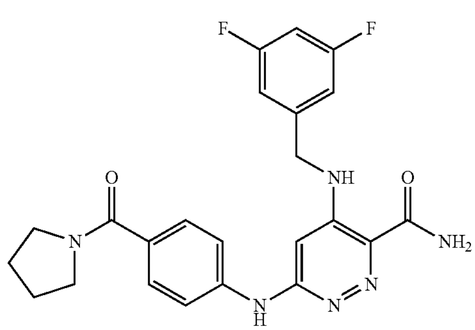 [SMILES: NC(=O)c1nnc(Nc2ccc(C(=O)N3CCCC3)cc2)cc1NCc1cc(F)cc(F)c1] | 452.47 | 453.4 | ++ | ++ | ++++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 83 | 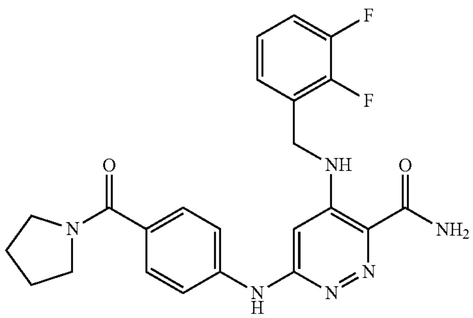 [SMILES: NC(=O)c1nnc(Nc2ccc(C(=O)N3CCCC3)cc2)cc1NCc1cccc(F)c1F] | 452.47 | 453.3 | + | ++ | ++++ | |
| 84 | 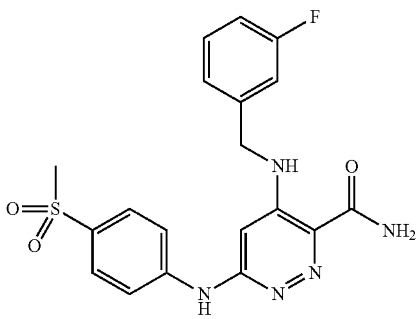 [SMILES: CS(=O)(=O)c1ccc(Nc2cc(NCc3cccc(F)c3)c(C(N)=O)nn2)cc1] | 415.45 | 416.2 | + | + | ++ | |
| 85 | 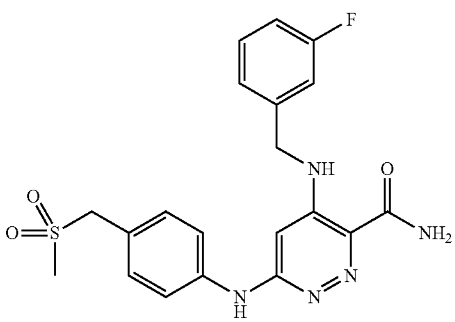 [SMILES: CS(=O)(=O)Cc1ccc(Nc2cc(NCc3cccc(F)c3)c(C(N)=O)nn2)cc1] | 429.47 | 430.2 | ++ | ++ | +++ | |
| 86 | 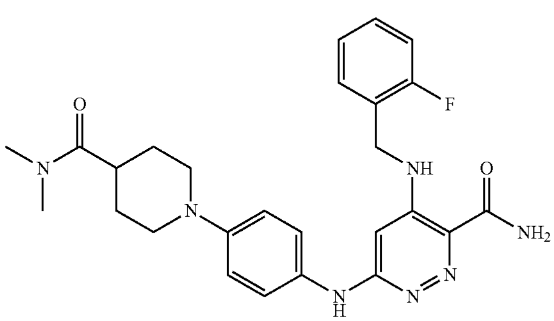 [SMILES: CN(C)C(=O)C1CCN(c2ccc(Nc3cc(NCc4ccccc4F)c(C(N)=O)nn3)cc2)CC1] | 491.57 | 492.4 | + | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 87 | 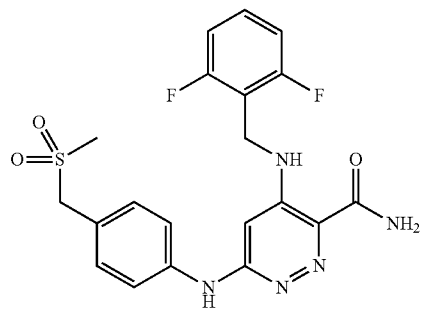 [SMILES: CS(=O)(=O)Cc1ccc(Nc2cc(NCc3c(F)cccc3F)c(C(N)=O)nn2)cc1] | 447.46 | 448.3 | ++ | ++ | ++++ | |
| 88 | 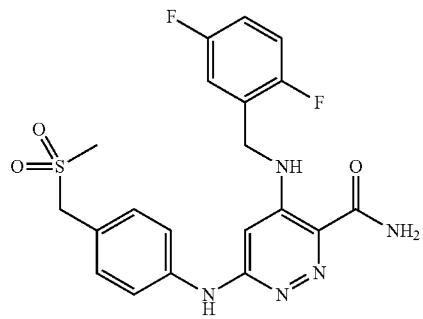 [SMILES: CS(=O)(=O)Cc1ccc(Nc2cc(NCc3cc(F)ccc3F)c(C(N)=O)nn2)cc1] | 447.46 | 448.3 | ++ | ++ | ++++ | |
| 89 | 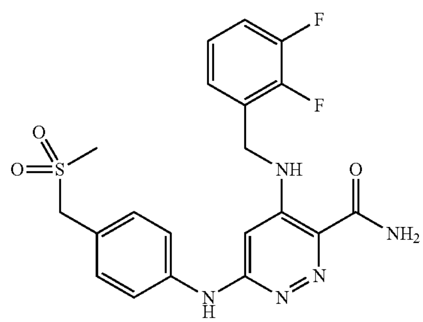 [SMILES: CS(=O)(=O)Cc1ccc(Nc2cc(NCc3cccc(F)c3F)c(C(N)=O)nn2)cc1] | 447.46 | 448.3 | ++ | ++ | ++++ | ++ |
| 90 | 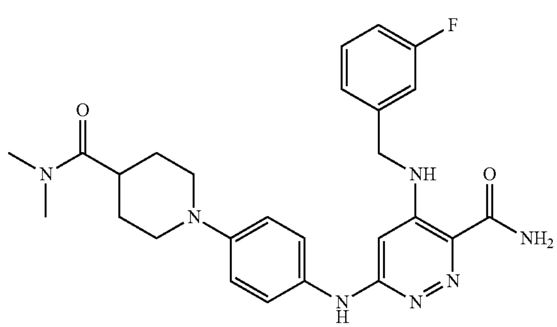 [SMILES: CN(C)C(=O)C1CCN(c2ccc(Nc3cc(NCc4cccc(F)c4)c(C(N)=O)nn3)cc2)CC1] | 491.57 | 492.4 | + | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 91 | 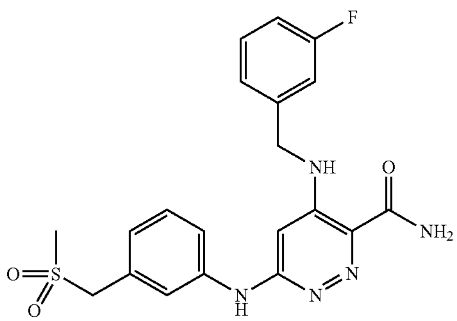 [SMILES: CS(=O)(=O)Cc1cccc(Nc2cc(NCc3cccc(F)c3)c(C(N)=O)nn2)c1] | 429.47 | 430.3 | + | + | +++ | |
| 92 | 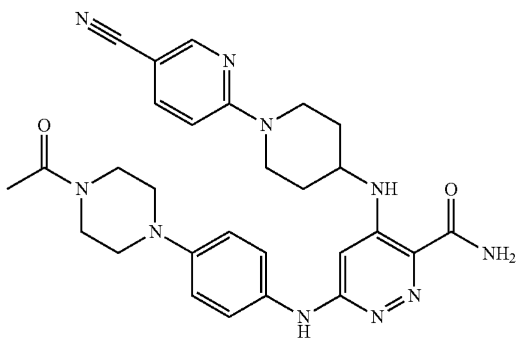 [SMILES: CC(=O)N1CCN(c2ccc(Nc3cc(NC4CCN(c5ccc(C#N)cn5)CC4)c(C(N)=O)nn3)cc2)CC1] | 540.63 | 541.4 | +++ | +++ | +++ | |
| 93 | 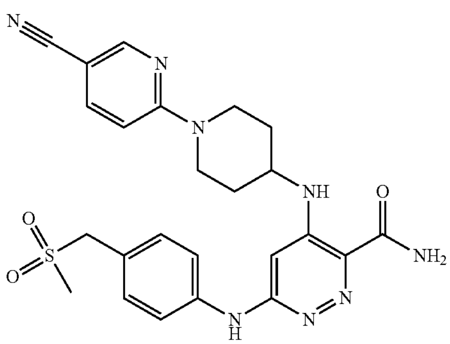 [SMILES: CS(=O)(=O)Cc1ccc(Nc2cc(NC3CCN(c4ccc(C#N)cn4)CC3)c(C(N)=O)nn2)cc1] | 506.59 | 507.4 | +++ | +++ | +++ | |
| 94 | 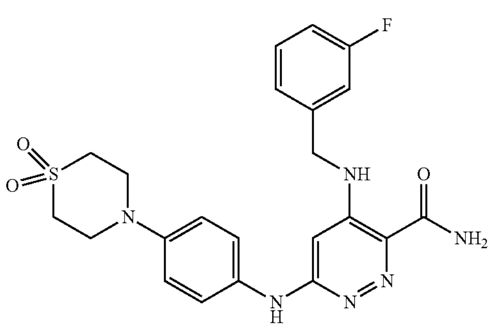 [SMILES: NC(=O)c1nnc(Nc2ccc(N3CCS(=O)(=O)CC3)cc2)cc1NCc1cccc(F)c1] | 470.53 | 471.3 | + | ++ | ++++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 95 | 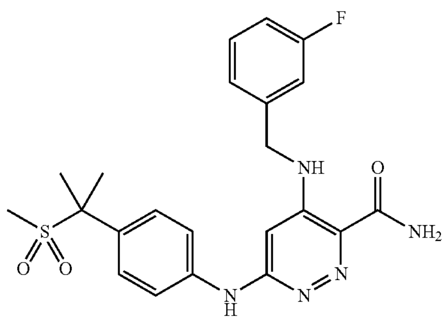 [SMILES: CC(C)(c1ccc(Nc2cc(NCc3cccc(F)c3)c(C(N)=O)nn2)cc1)S(C)(=O)=O] | 457.53 | 458.3 | + | ++ | +++ | |
| 96 | 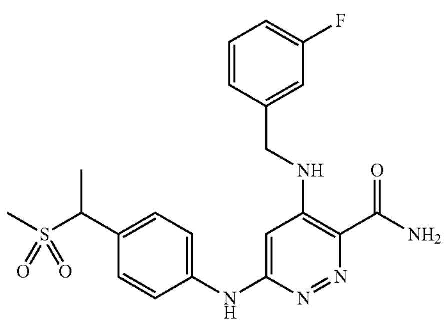 [SMILES: CC(c1ccc(Nc2cc(NCc3cccc(F)c3)c(C(N)=O)nn2)cc1)S(C)(=O)=O] | 443.50 | 444.3 | ++ | ++ | +++ | |
| 97 | 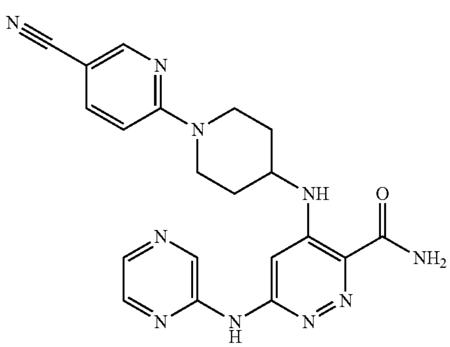 [SMILES: N#Cc1ccc(N2CCC(Nc3cc(Nc4cnccn4)nnc3C(N)=O)CC2)nc1] | 416.45 | 417.3 | ++++ | ++++ | ++++ | |
| 98 | 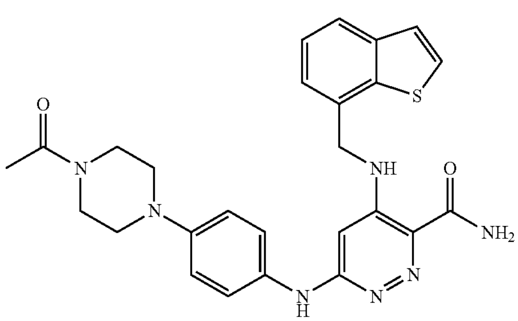 [SMILES: CC(=O)N1CCN(c2ccc(Nc3cc(NCc4cccc5ccsc45)c(C(N)=O)nn3)cc2)CC1] | 501.61 | 502.3 | ++ | +++ | ++++ | + |

TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 99 | 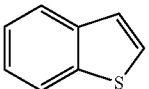 | 459.58 | 460.3 | ++ | +++ | ++++ | ++ |
| 100 | 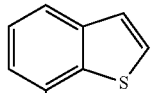 | 467.57 | 468.2 | ++ | ++ | ++++ | |
| 101 | 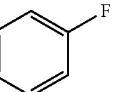 | 408.44 | 409.4 | + | ++ | ++ | |
| 102 | 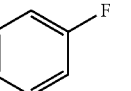 | 444.49 | 445.3 | + | ++ | +++ | |

113 114
TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 103 | 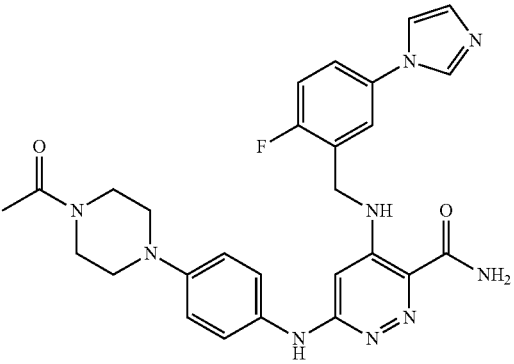 [SMILES: CC(=O)N1CCN(c2ccc(Nc3cc(NCc4cc(-n5ccnc5)ccc4F)c(C(N)=O)nn3)cc2)CC1] | 529.58 | 530.4 | + | ++ | +++ | |
| 104 | 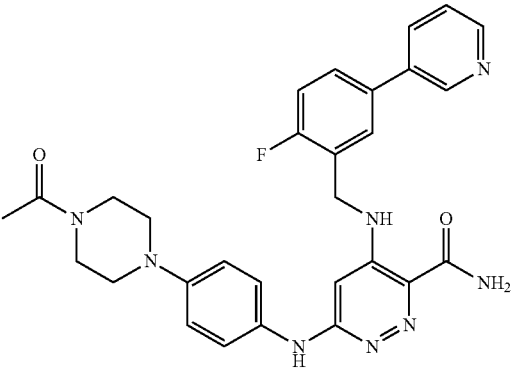 [SMILES: CC(=O)N1CCN(c2ccc(Nc3cc(NCc4cc(-c5cccnc5)ccc4F)c(C(N)=O)nn3)cc2)CC1] | 540.60 | 541.4 | + | ++ | +++ | |
| 105 | 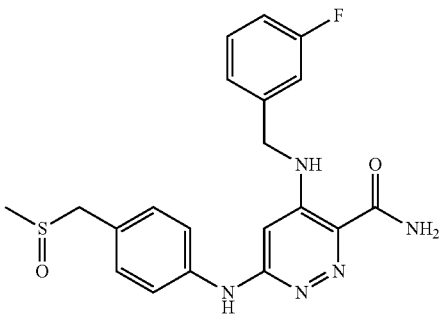 [SMILES: CS(=O)Cc1ccc(Nc2cc(NCc3cccc(F)c3)c(C(N)=O)nn2)cc1] | 413.48 | 414.3 | ++ | ++ | +++ | |
| 106 | 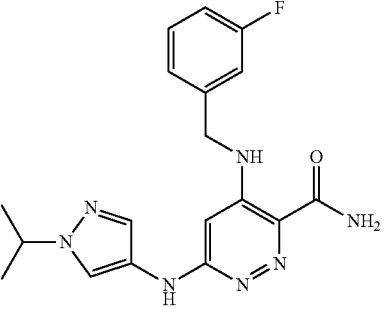 [SMILES: CC(C)n1cc(Nc2cc(NCc3cccc(F)c3)c(C(N)=O)nn2)cn1] | 369.40 | 370.3 | + | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 107 | 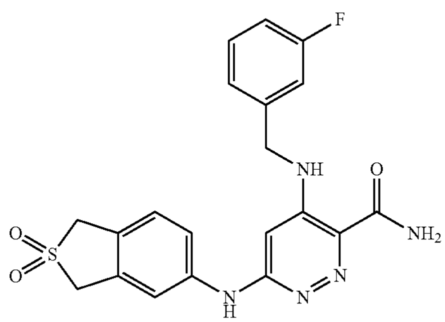 [SMILES: NC(=O)c1nnc(Nc2ccc3c(c2)CS(=O)(=O)C3)cc1NCc1cccc(F)c1] | 427.46 | 428.2 | + | ++ | +++ | |
| 108 | 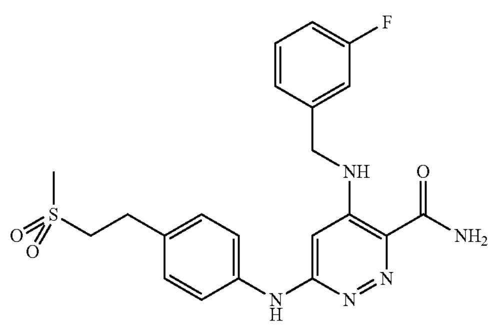 [SMILES: CS(=O)(=O)CCc1ccc(Nc2cc(NCc3cccc(F)c3)c(C(N)=O)nn2)cc1] | 443.50 | 444.3 | + | ++ | +++ | |
| 109 | 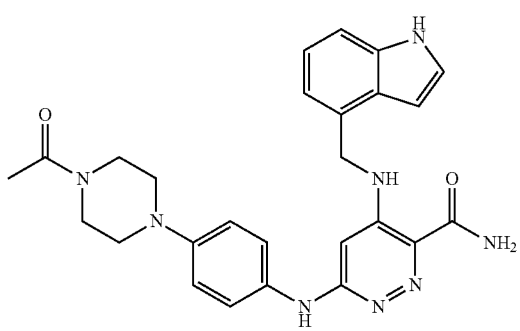 [SMILES: CC(=O)N1CCN(c2ccc(Nc3cc(NCc4cccc5[nH]ccc45)c(C(N)=O)nn3)cc2)CC1] | 484.56 | 485.3 | +++ | +++ | +++++ | |
| 110 | 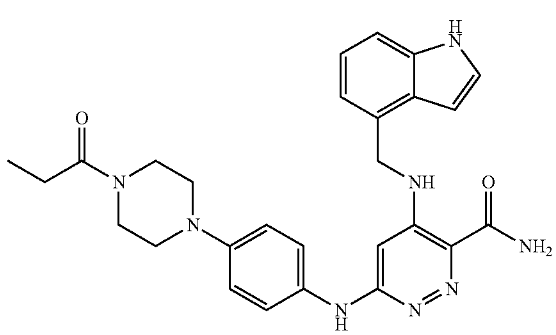 [SMILES: CCC(=O)N1CCN(c2ccc(Nc3cc(NCc4cccc5[nH]ccc45)c(C(N)=O)nn3)cc2)CC1] | 498.59 | 499.3 | +++ | +++ | ++++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
| --- | --- | --- | --- | --- | --- | --- | --- |
| 111 | 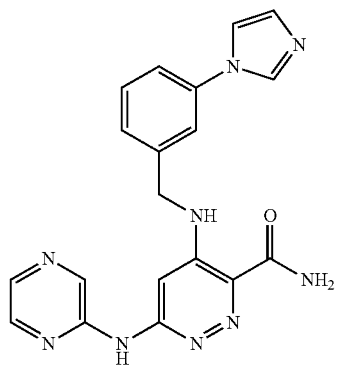 [SMILES: NC(=O)c1nnc(Nc2cnccn2)cc1NCc1cccc(-n2ccnc2)c1] | 387.41 | 388.3 | + | + | ++ | |
| 112 | 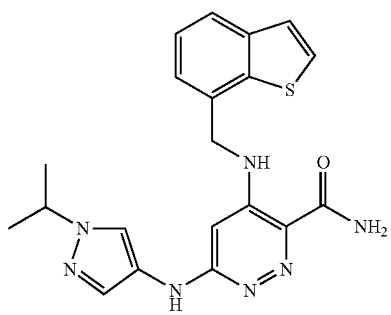 [SMILES: CC(C)n1cc(Nc2cc(NCc3cccc4ccsc34)c(C(N)=O)nn2)cn1] | 407.50 | 408.3 | ++ | +++ | ++++ | |
| 113 | 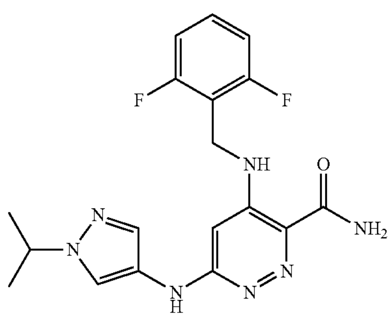 [SMILES: CC(C)n1cc(Nc2cc(NCc3c(F)cccc3F)c(C(N)=O)nn2)cn1] | 387.39 | 388.3 | ++ | +++ | ++++ | |
| 114 | 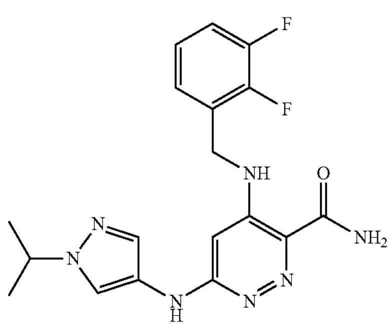 [SMILES: CC(C)n1cc(Nc2cc(NCc3cccc(F)c3F)c(C(N)=O)nn2)cn1] | 387.39 | 388.3 | ++ | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 115 | 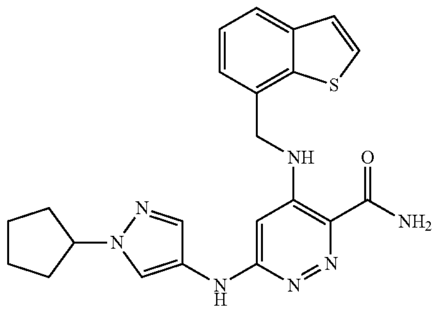 [SMILES: NC(=O)c1nnc(Nc2cnn(C3CCCC3)c2)cc1NCc1cccc2ccsc12] | 433.54 | 434.26 | + | +++ | +++ | |
| 116 | 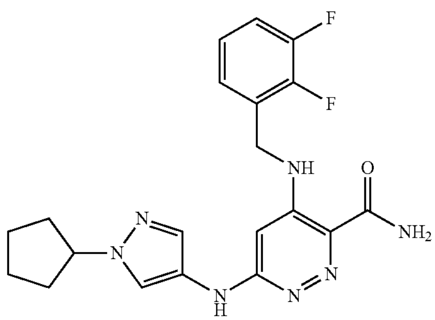 [SMILES: NC(=O)c1nnc(Nc2cnn(C3CCCC3)c2)cc1NCc1cccc(F)c1F] | 413.43 | 414.3 | + | ++ | +++ | |
| 117 | 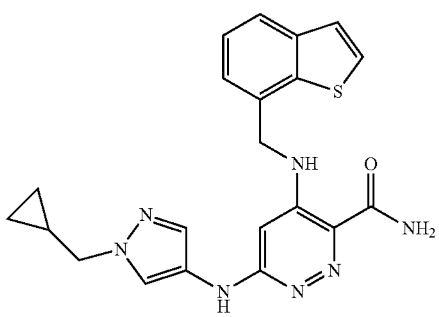 [SMILES: NC(=O)c1nnc(Nc2cnn(CC3CC3)c2)cc1NCc1cccc2ccsc12] | 419.51 | 420.3 | ++ | +++ | +++ | |
| 118 | 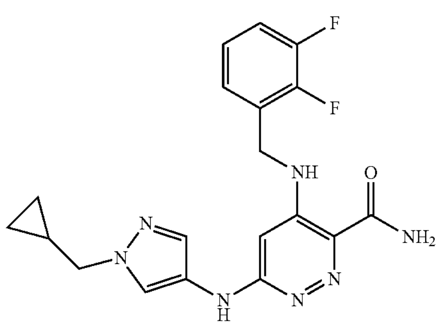 [SMILES: NC(=O)c1nnc(Nc2cnn(CC3CC3)c2)cc1NCc1cccc(F)c1F] | 399.41 | 400.3 | ++ | ++ | +++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
| --- | --- | --- | --- | --- | --- | --- | --- |
| 119 | 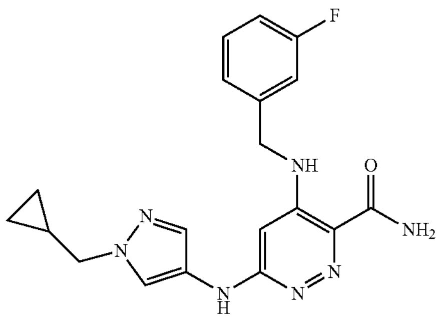 [SMILES: NC(=O)c1nnc(Nc2cnn(CC3CC3)c2)cc1NCc1cccc(F)c1] | 381.42 | 382.3 | + | ++ | +++ | |
| 120 | 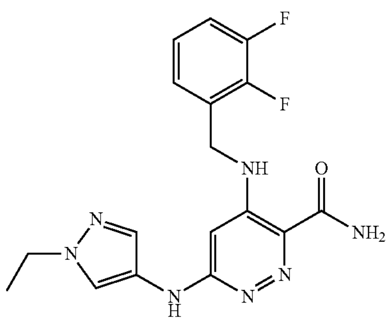 [SMILES: CCn1cc(Nc2cc(NCc3cccc(F)c3F)c(C(N)=O)nn2)cn1] | 373.37 | 374.2 | + | ++ | +++ | |
| 121 | 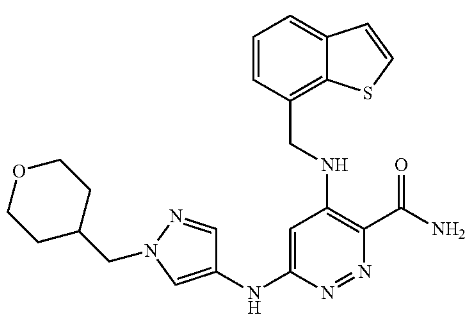 [SMILES: NC(=O)c1nnc(Nc2cnn(CC3CCOCC3)c2)cc1NCc1cccc2ccsc12] | 463.56 | 464.3 | ++ | +++ | ++++ | |
| 122 | 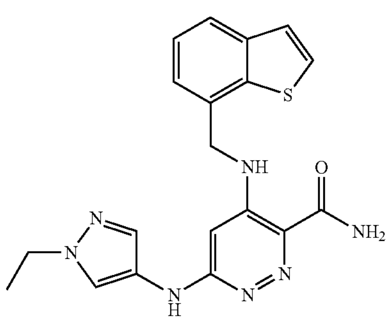 [SMILES: CCn1cc(Nc2cc(NCc3cccc4ccsc34)c(C(N)=O)nn2)cn1] | 393.47 | 394.3 | ++ | +++ | ++++ | |

TABLE 1-continued

JAK inhibition activity of compound of the invention

| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 123 | 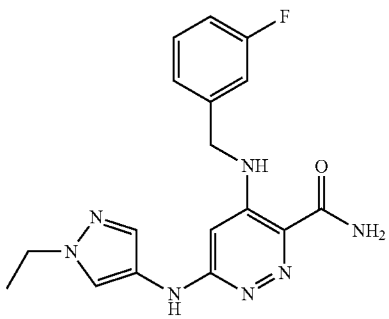 [SMILES: CCn1cc(Nc2cc(NCc3cccc(F)c3)c(C(N)=O)nn2)cn1] | 355.38 | 356.1 | + | ++ | +++ | |
| 124 | 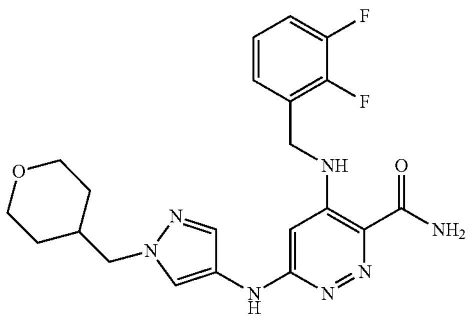 [SMILES: NC(=O)c1nnc(Nc2cnn(CC3CCOCC3)c2)cc1NCc1cccc(F)c1F] | 443.46 | 444.3 | + | ++ | ++++ | |
| 125 | 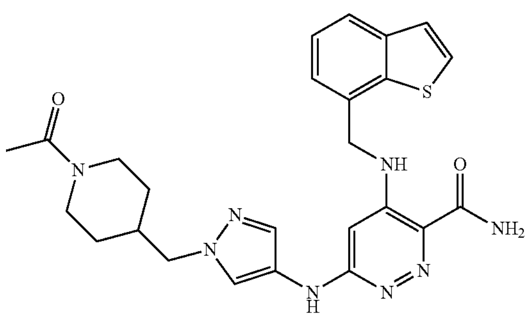 [SMILES: CC(=O)N1CCC(Cn2cc(Nc3cc(NCc4cccc5ccsc45)c(C(N)=O)nn3)cn2)CC1] | 504.62 | 505.3 | ++ | +++ | ++++ | |
| 126 | 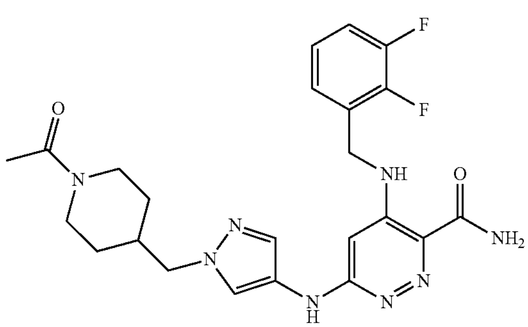 [SMILES: CC(=O)N1CCC(Cn2cc(Nc3cc(NCc4cccc(F)c4F)c(C(N)=O)nn3)cn2)CC1] | 484.51 | 485.3 | + | ++ | ++++ | |

TABLE 1-continued
JAK inhibition activity of compound of the invention
| No. | Structure | MW (g/mol) | MS | JAK1 IC50 (μM) | JAK2 IC50 (μM) | JAK3 IC50 (μM) | Tyk2 IC50 (μM) |
|---|---|---|---|---|---|---|---|
| 127 | 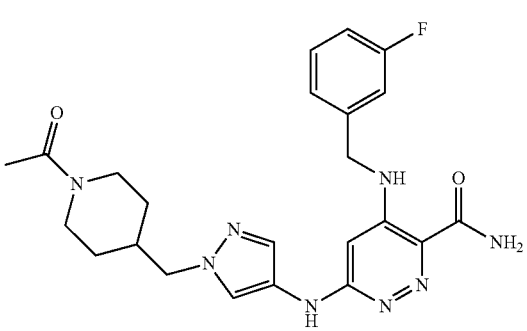 [SMILES: CC(=O)N1CCC(Cn2cc(Nc3cc(NCc4cccc(F)c4)c(C(N)=O)nn3)cn2)CC1] | 466.52 | 467.3 | + | ++ | +++ | |
| 128 | 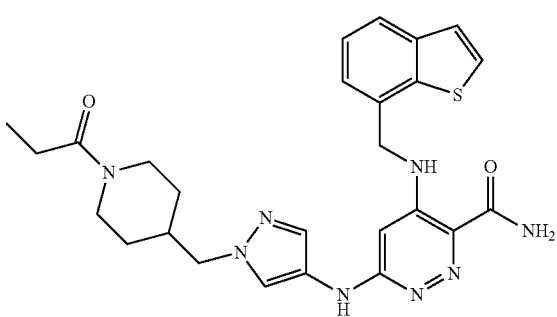 [SMILES: CCC(=O)N1CCC(Cn2cc(Nc3cc(NCc4cccc5ccsc45)c(C(N)=O)nn3)cn2)CC1] | 518.64 | 519.3 | ++ | +++ | ++++ | |
| 129 | 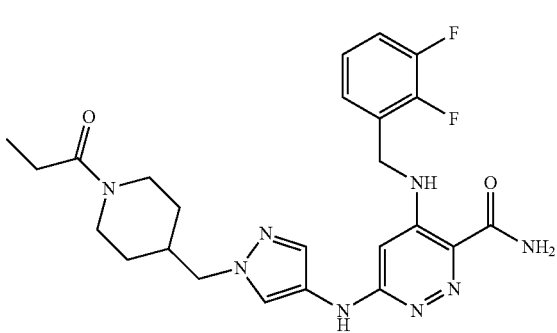 [SMILES: CCC(=O)N1CCC(Cn2cc(Nc3cc(NCc4cccc(F)c4F)c(C(N)=O)nn3)cn2)CC1] | 498.54 | 499.4 | ++ | ++ | ++++ | |
| 130 | 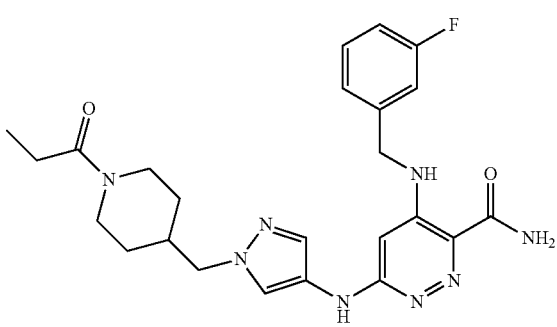 [SMILES: CCC(=O)N1CCC(Cn2cc(Nc3cc(NCc4cccc(F)c4)c(C(N)=O)nn3)cn2)CC1] | 480.55 | 481.4 | + | ++ | +++ | |

TABLE 1-continued

JAK inhibition activity of compound of the invention

| No. | Structure | MW (g/mol) | MS | JAK1 IC50 (µM) | JAK2 IC50 (µM) | JAK3 IC50 (µM) | Tyk2 IC50 (µM) |
|---|---|---|---|---|---|---|---|
| 131 | 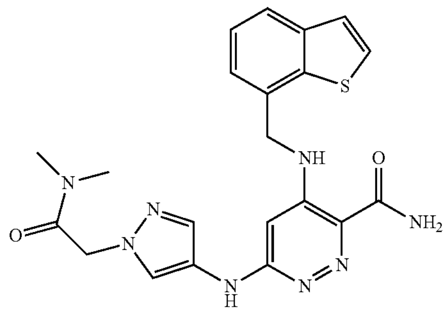 [SMILES: CN(C)C(=O)Cn1cc(Nc2cc(NCc3cccc4ccsc34)c(C(N)=O)nn2)cn1] | 450.53 | 451.3 | ++ | ++ | +++ | |
| 132 | 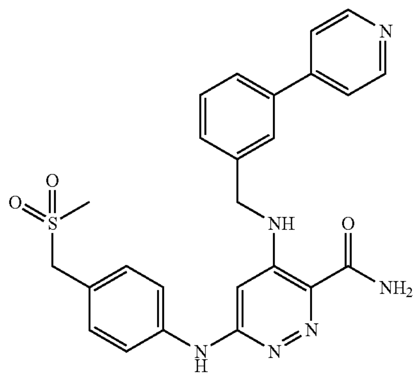 [SMILES: CS(=O)(=O)Cc1ccc(Nc2cc(NCc3cccc(-c4ccncc4)c3)c(C(N)=O)nn2)cc1] | 488.57 | 489.3 | + | + | +++ | |
| 133 | 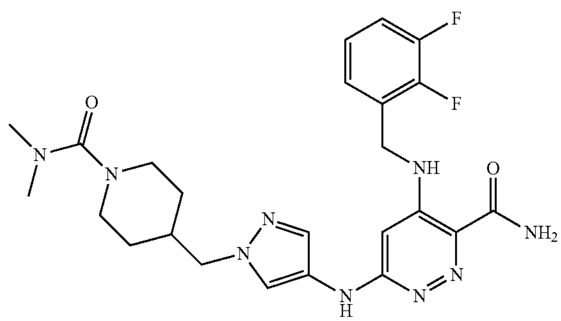 [SMILES: CN(C)C(=O)N1CCC(Cn2cc(Nc3cc(NCc4cccc(F)c4F)c(C(N)=O)nn3)cn2)CC1] | 513.55 | 514.4 | + | ++ | ++++ | |

Example 9

GMCSF-Induced pSTAT5 Formation in TF1 (JAK2 Cellular Assay)

100 µl aliquots of TF1 (2.5×10$^6$/ml) cells were pre-treated with various concentrations JAK inhibitors (0.04 to 5 µM, including 0.2 µM and 1 µM) for 1 hour at 37° C. Cells were then stimulated with 2 ng/ml GM-CSF for 10 minutes at 37° C. The reaction was terminated by the addition of 60 µl 16% paraformaldehyde followed by incubation for 10 minutes at room temperature. Cells were washed twice (centrifugation 5 minutes room temperature at 385×g) in PBS followed by re-suspension in −20° C. 50% methanol in PBS and storage at 4° C. overnight. The following day, cells were washed in PBS/BSA and re-suspended in the same buffer containing STAT5 Y694 specific antibody. Following incubation with antibodies, cells were washed and analyzed by flow cytometry (BD Biosciences; FACS Calibur). The gate was set on live cells in the SSC-FSC plot and 10,000 events were collected.

Example 10

Intracellular STAT Phosphorylation Following Cytokine Stimulation of Peripheral Blood Mononuclear Cells (PBMC). (JAK3/JAK1 Cellular Assay)

Human whole blood was collected into lithium heparin vacutainer tubes from the antecubital vein of human subjects. Peripheral blood mononuclear cells (PBMC) were prepared by layering 10 ml anti-coagulated blood over 5 ml lymphoprep in a 15 ml conical tube and centrifugation for 20 minutes at 400×g in a swinging bucket rotor. The lymphocyte layer was removed, washed twice in tissue culture media (RPMI containing 10% fetal bovine serum) prior to re-suspension in the same media at 2×10$^6$ cells/ml. 100 µl aliquots of PMBCs were incubated for 1 h at 37° C. with various concentrations of JAK inhibitors prior to stimulation for 15 minutes with 1.5 ng/ml of IL2 or IL4. The reaction was terminated by the addition of 60 µl 16% paraformaldehyde, followed by incubation at room temperature for 10 minutes. Fixed cells were washed twice in PBS, and then re-suspended in −20° C. 50% methanol diluted in PBS and stored at 4° C. overnight. Following permeabilization of the cell membrane in methanol, cells were washed twice in PBS containing 1% BSA and PBMCs were re-suspended in the same buffer containing CD3 and STAT5 Y694 specific antibodies (IL2 stimulations) or CD3, CD14, CD19, and STAT6 Y641 specific antibodies (IL4 stimulations) for 1 hour at room temperature. Cells were then washed and re-suspended in PBS/BSA buffer and assessed by flow cytometry (LSRII; BD Biosciences) for effect of JAK inhibitors on cytokine mediated STAT phosphorylation.

In Table 2 below, activity in the JAK assays is provided as follows: +++++=$IC_{50}$<0.0010 µM; ++++=0.0010 µM<$IC_{50}$<0.010 µM; +++=0.010 µM<$IC_{50}$<0.10 µM; ++=0.10 µM<$IC_{50}$<1.0 µM; +=$IC_{50}$>1 µM. Percent inhibition of STAT phosphorylation in the cellular assays is provided for the compounds at the given concentrations.

TABLE 2

Enzyme and cellular activity data for selected compounds of the invention.

| Assay | Compound 18 | Compound 20 | Compound 33 | Compound 98 | Compound 109 |
|---|---|---|---|---|---|
| JAK3 | ++++ | ++++ | ++++ | ++++ | ++++ |
| JAK2 | ++ | ++ | +++ | +++ | +++ |
| JAK1 | + | + | ++ | + | +++ |
| TYK2 | ++ | ++ | +++ | + | |
| IL2-STAT5 | | 32% at 0.2 µM | 31% at 0.2 µM | 13% at 0.2 µM | 69% at 0.2 µM |
| IL2-STAT5 | | 60% at 1.0 µM | 53% at 1.0 µM | 64% at 1.0 µM | 95% at 1.0 µM |
| TF1/GM-CSF | | 3% at 0.1 µM | 0% at 0.1 µM | | |
| TF1/GM-CSF | | 2% at 1.0 µM | 17% at 1.0 µM | | |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound according to formula I:

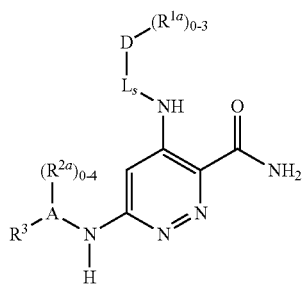

(I)

or a tautomer thereof or a pharmaceutically acceptable salt or hydrate thereof, wherein:

D is selected from the group consisting of $C_{1-8}$ alkyl, $C_{6-10}$ aryl, $C_{3-8}$ cycloalkyl, and 5- to 6-membered heteroaryl, each $R^{1a}$ is independently selected from the group consisting of halo, hydroxy, cyano, $C_{1-8}$ alkyl, $C_{1-8}$ alkoxy, $C_{3-8}$ cycloalkyl, $C_{6-10}$ aryl, 5- to 6-membered heteroaryl, and 5- to 8-membered heterocyclyl, or two $R^{1a}$ moieties, together with the atoms to which they are attached, form a fused 5- to 6-membered ring;

L is selected from the group consisting of 5- to 6-membered heterocyclyl, —C(R)$_2$—, and —[C(R)$_2$]$_2$—, wherein each R is independently selected from the group consisting of H and $C_{1-4}$ alkyl;

the subscript s is 0 or 1

A is selected from the group consisting of $C_{6-10}$ aryl and 5- to 6-membered heteroaryl, each $R^{2a}$ is independently selected from the group consisting of halo, hydroxy, cyano, $C_{1-8}$ alkyl, $C_{1-8}$ alkoxy, $C_{6-10}$ aryl, and 5- to 6-membered heterocyclyl, or two $R^{2a}$ moieties, together with the atoms to which they are attached, form a fused 5- to 6-membered ring;

$R^3$ is selected from hydrogen, $C_{1-8}$ alkyl, $C_{1-8}$ haloalkyl, $C_{1-8}$ alkoxy, $R^{3a}$—(SO)—($R^{3b}$)$_t$—, $R^{3a}$—(SO)$_2$—($R^{3b}$)$_t$—, $R^{3c}$—(CO)—($R^{3d}$)$_t$—, ($C_{3-8}$ cycloalkyl)-($R^{3e}$)$_t$—, and (5- to 8-membered heterocyclyl)-($R^{3e}$)$_t$—; wherein $R^{3a}$ is selected from the group consisting of OH, $C_{1-8}$ alkyl, and N(R°)$_2$, wherein each R° is independently H or $C_{1-4}$ alkyl;

$R^{3b}$ is selected from the group consisting of $C_{1-8}$ alkylene, and —NR°—, wherein R° is H or $C_{1-4}$ alkyl;

$R^{3c}$ is selected from the group consisting of $C_{1-8}$ alkyl, $C_{3-8}$ cycloalkyl, $C_{1-8}$ alkoxy, 5- to 8-membered heterocyclyl, and N(R°)$_2$, wherein each R° is independently H or $C_{1-4}$ alkyl;

$R^{3d}$ is selected from the group consisting of $C_{1-8}$ alkylene, and —NR°—, wherein R° is H or $C_{1-4}$ alkyl;

$R^{3e}$ is selected from the group consisting of $C_{1-8}$ alkylene, and $C_{1-8}$ heteroalkylene; and the subscript t is 0 or 1;

and wherein each heteroaryl group and each heterocyclic group are substituted with from 0 to 3 moieties independently selected from the group consisting of halo, cyano, $C_{1-4}$ alkyl, ($C_{1-4}$ alkyl)-(CO)—, and (R$^4$)$_2$N—

(CO)— wherein each $R^4$ is independently selected from the group consisting of H and $C_{1-4}$ alkyl.

2. The compound of claim 1, or a tautomer thereof or a pharmaceutically acceptable salt or hydrate thereof, wherein A is $C_{6-10}$ aryl.

3. The compound of claim 2, or a tautomer thereof or a pharmaceutically acceptable salt or hydrate thereof, wherein A is phenyl.

4. The compound of claim 1, or a tautomer thereof or a pharmaceutically acceptable salt or hydrate thereof, wherein A is 5- to 6-membered heteroaryl.

5. The compound of claim 4, or a tautomer thereof or a pharmaceutically acceptable salt or hydrate thereof, wherein A is selected from the group consisting of pyrazinyl, pyrazolyl, pyridinyl, and thiazolyl.

6. The compound of any one of claims 1-5, or a tautomer thereof or a pharmaceutically acceptable salt or hydrate thereof, wherein each $R^{2a}$ is independently selected from the group consisting of halo, $C_{1-8}$ alkyl, and $C_{1-8}$ alkoxy, or two $R^{2a}$ moieties, together with the atoms to which they are attached, form a fused 5- to 6-membered ring.

7. The compound of claim 1, or a tautomer thereof or a pharmaceutically acceptable salt or hydrate thereof, wherein D is $C_{1-8}$ alkyl.

8. The compound of claim 7, or a tautomer thereof or a pharmaceutically acceptable salt or hydrate thereof, wherein D is selected from the group consisting of methyl and isopropyl.

9. The compound of claim 1, or a tautomer thereof or a pharmaceutically acceptable salt or hydrate thereof, wherein D is $C_{6-10}$ aryl which is substituted with from 0 to 3 $R^{1a}$.

10. The compound of claim 9, or a tautomer thereof or a pharmaceutically acceptable salt or hydrate thereof, wherein D is phenyl.

11. The compound of claim 1, or a tautomer thereof or a pharmaceutically acceptable salt or hydrate thereof, wherein D is $C_{3-8}$ cycloalkyl.

12. The compound of claim 11, or a tautomer thereof or a pharmaceutically acceptable salt or hydrate thereof, wherein D is selected from the group consisting of cyclobutyl, cyclopentyl, and cyclohexyl.

13. The compound of claim 1, or a tautomer thereof or a pharmaceutically acceptable salt or hydrate thereof, wherein D is 5- to 6-membered heteroaryl.

14. The compound of claim 13, or a tautomer thereof or a pharmaceutically acceptable salt or hydrate thereof, wherein D is selected from the group consisting of pyridinyl and thiophenyl.

15. The compound of any one of claims 1 or 7-14, or a tautomer thereof or a pharmaceutically acceptable salt or hydrate thereof, wherein each $R^{1a}$ is independently selected from the group consisting of cyano, chloro, fluoro, methyl, methoxy, imidazolyl, and pyridinyl, or two $R^{1a}$ moieties, together with the atoms to which they are attached, form a fused 5- to 6-membered ring.

16. The compound of claim 1, or a tautomer thereof or a pharmaceutically acceptable salt or hydrate thereof, wherein $R^3$ is selected from the group consisting of $C_{1-8}$ alkyl, $C_{1-8}$ haloalkyl, and $C_{1-8}$ alkoxy.

17. The compound of claim 1, or a tautomer thereof or a pharmaceutically acceptable salt or hydrate thereof, wherein $R^3$ is selected from the group consisting of $R^{3a}$—(SO)—$(R^{3b})_t$—, $R^{3a}$—(SO)$_2$—$(R^{3b})_t$—, and $R^{3c}$—(CO)—$(R^{3d})_t$—.

18. The compound of claim 1, or a tautomer thereof or a pharmaceutically acceptable salt or hydrate thereof, wherein $R^3$ is selected from the group consisting of ($C_{3-8}$ cycloalkyl)-$(R^{3e})_t$— and (5- to 8-membered heterocyclyl)-$(R^{3e})_t$—.

19. The compound of claim 1, or a tautomer thereof or a pharmaceutically acceptable salt or hydrate thereof, wherein $R^3$ is selected from the group consisting of

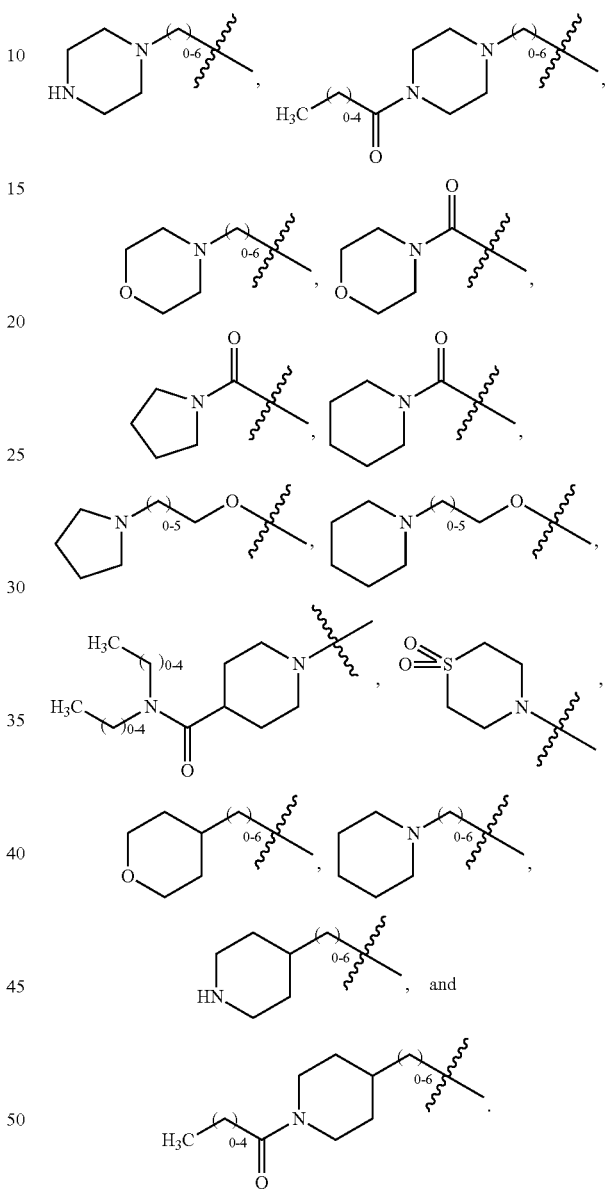

20. The compound of claim 1, or a tautomer thereof or a pharmaceutically acceptable salt or hydrate thereof, wherein $R^3$ is selected from the group consisting of

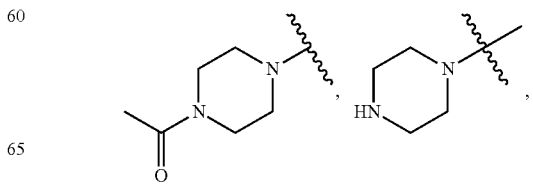

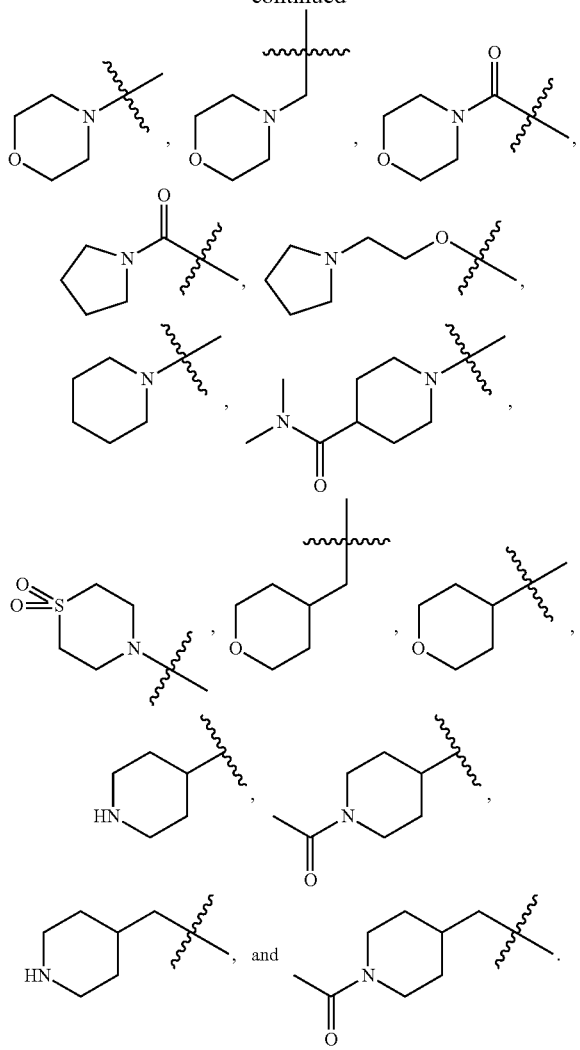

21. The compound of claim 1, or a tautomer thereof or a pharmaceutically acceptable salt or hydrate thereof, wherein the subscript s is 0.

22. The compound of claim 1, or a tautomer thereof or a pharmaceutically acceptable salt or hydrate thereof, wherein the subscript s is 1 and L is selected from the group consisting of —C(R)$_2$— and —[C(R)$_2$]$_2$—.

23. The compound of claim 1, or a tautomer thereof or a pharmaceutically acceptable salt or hydrate thereof, wherein the subscript s is 1 and L is 5- to 6-membered heterocyclyl.

24. The compound of claim 1, or a tautomer thereof or a pharmaceutically acceptable salt or hydrate thereof, wherein
A is phenyl which is substituted with from 0 to 2 R$^{2a}$; and
each R$^{2a}$ is independently selected from the group consisting of halo, C$_{1-4}$ alkyl, and C$_{1-4}$ alkoxy; or two R$^{2a}$ moieties, together with the carbon atoms to which they are attached, form a fused 5- to 6-membered ring.

25. The compound of claim 24, or a tautomer thereof or a pharmaceutically acceptable salt or hydrate thereof, wherein
D is selected from the group consisting of methyl, ethyl, n-propyl, isopropyl, n-butyl, tert-butyl, sec-butyl, cyclobutyl, cyclopentyl, cyclohexyl, phenyl, pyridinyl, and thiophenyl, each of which is substituted with from 0 to 2 R$^{1a}$, wherein each R$^{1a}$ is independently selected from the group consisting of halo, hydroxy, cyano, C$_{1-8}$ alkyl, C$_{1-8}$ alkoxy, C$_{3-8}$ cycloalkyl, C$_{6-10}$ aryl, 5- to 6-membered heteroaryl, and 5- to 8-membered heterocyclyl, or
two R$^{1a}$ moieties, together with the atoms to which they are attached, form a fused 5- to 6-membered ring.

26. The compound of claim 24 or claim 25, or a tautomer thereof or a pharmaceutically acceptable salt or hydrate thereof, wherein R$^3$ is selected from the group consisting of acetamido; (N-methylacetamido); dimethylcarbamoyl; N-methylcyclopropanecarboxamido; (N-methyl)methoxycarboxamido; (methylsulfonyl)methyl; (methylsulfinyl)methyl; (morpholino)methyl; methylsulfonyl; 1-(methylsulfonyl)ethyl; 1-methyl-1-(methylsulfonyl)ethyl; 2-(methylsulfonyl)ethyl; (methylsulfonyl)methylamino; morpholino; 4-acetylpiperazin-1-yl; piperazin-1-yl; 4-propionylpiperazin-1-yl; 4-(dimethylcarbamoyl)piperidin-1-yl; 1-propionylpiperidin-4-yl; 1,1-dioxidothiomorpholino; morpholine-4-carbonyl; pyrrolidine-1-carbonyl; and 2-(pyrrolidin-1-yl)ethoxy.

27. The compound of claim 25, or a tautomer thereof or a pharmaceutically acceptable salt or hydrate thereof, wherein A is phenyl with 0 R$^{2a}$ moieties.

28. The compound of claim 1, or a tautomer thereof or a pharmaceutically acceptable salt or hydrate thereof, wherein A is selected from the group consisting of pyrazolyl, pyridinyl, and thiazolyl.

29. The compound of claim 28, or a tautomer thereof or a pharmaceutically acceptable salt or hydrate thereof, wherein
D is selected from the group consisting of phenyl, pyridinyl, and piperidinyl, each of which is substituted with from 0 to 2 R$^{1a}$, wherein
each R$^{1a}$ is independently selected from the group consisting of halo, cyano, 5- to 6-membered heteroaryl, and 5- to 6-membered heterocyclyl, or
two R$^{1a}$ moieties, together with the atoms to which they are attached, form a fused 5- to 6-membered ring.

30. The compound of claim 28 or claim 29, or a tautomer thereof or a pharmaceutically acceptable salt or hydrate thereof, wherein R$^3$ is selected from the group consisting of hydrogen; methyl; ethyl; isopropyl; cyclopentyl; cyclopropylmethyl; 2-(dimethylamino)-2-oxoethyl; (tetrahydro-2H-pyran-4-yl)methyl; 1-(dimethylcarbamoyl)piperidin-4-yl)methyl; morpholino; morpholine-4-carbonyl; pyrrolidone-1-carbonyl; 1-propionylpiperidin-4-yl; piperazin-1-yl; and 4-acetylpiperazin-1-yl.

31. The compound of claim 1, or a tautomer thereof or a pharmaceutically acceptable salt or hydrate thereof, which is selected from the group consisting of:

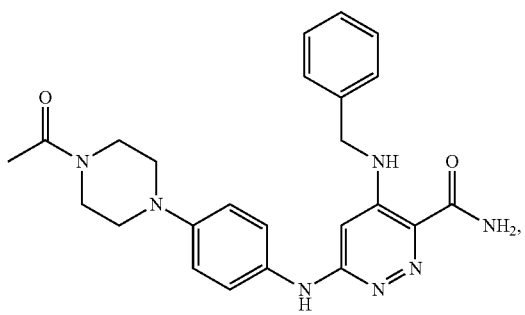

135
-continued
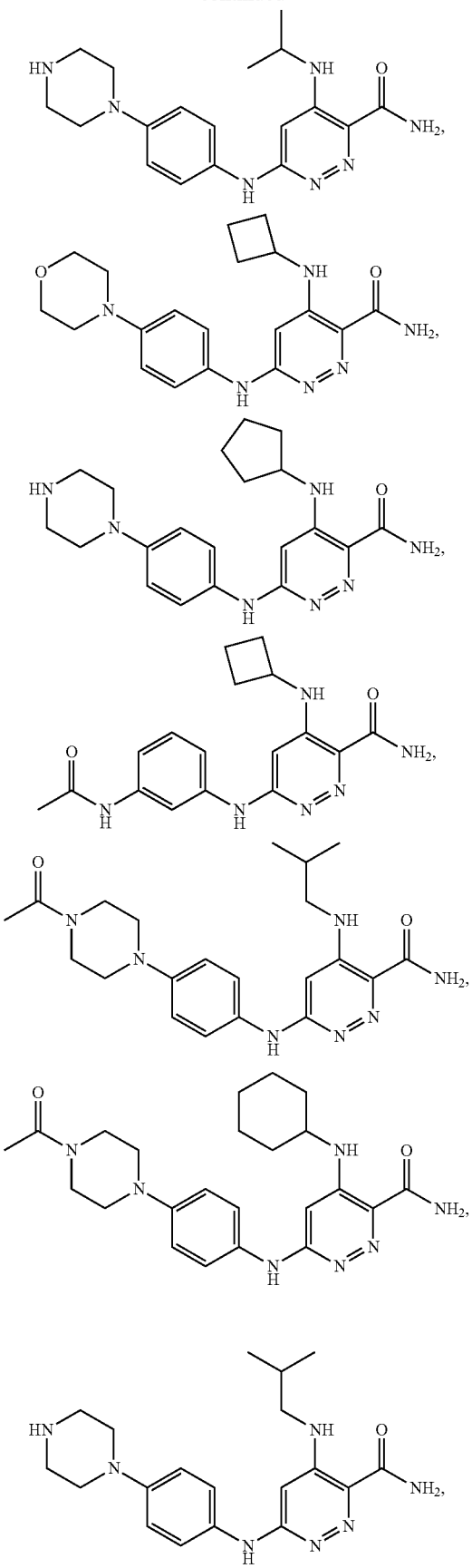
136
-continued
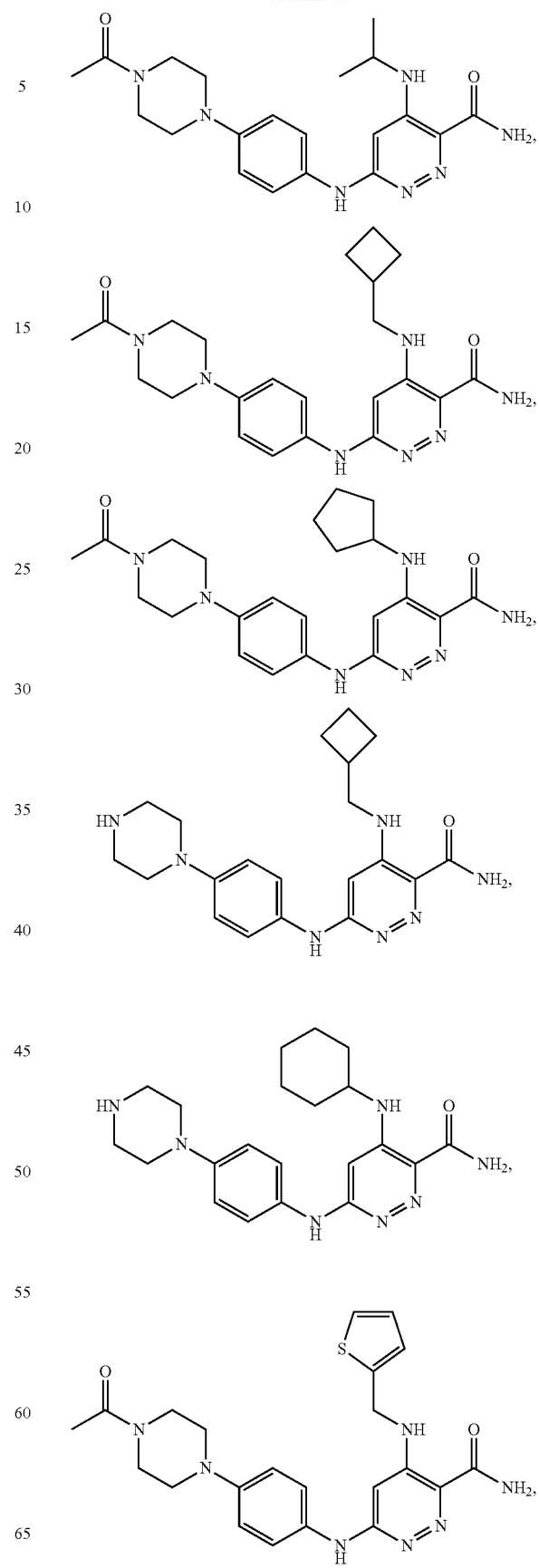

137
-continued
138
-continued
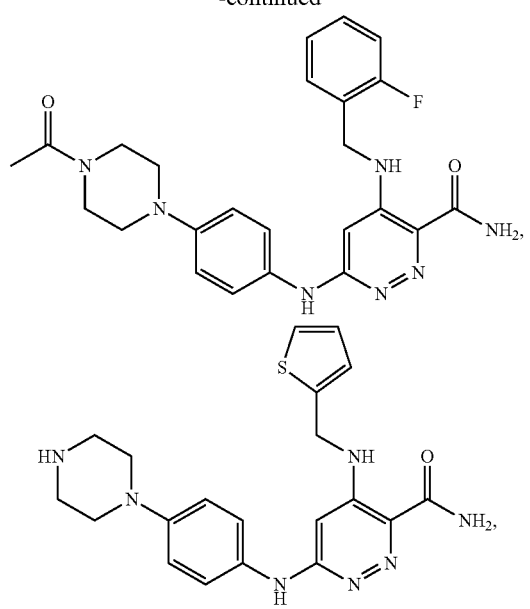
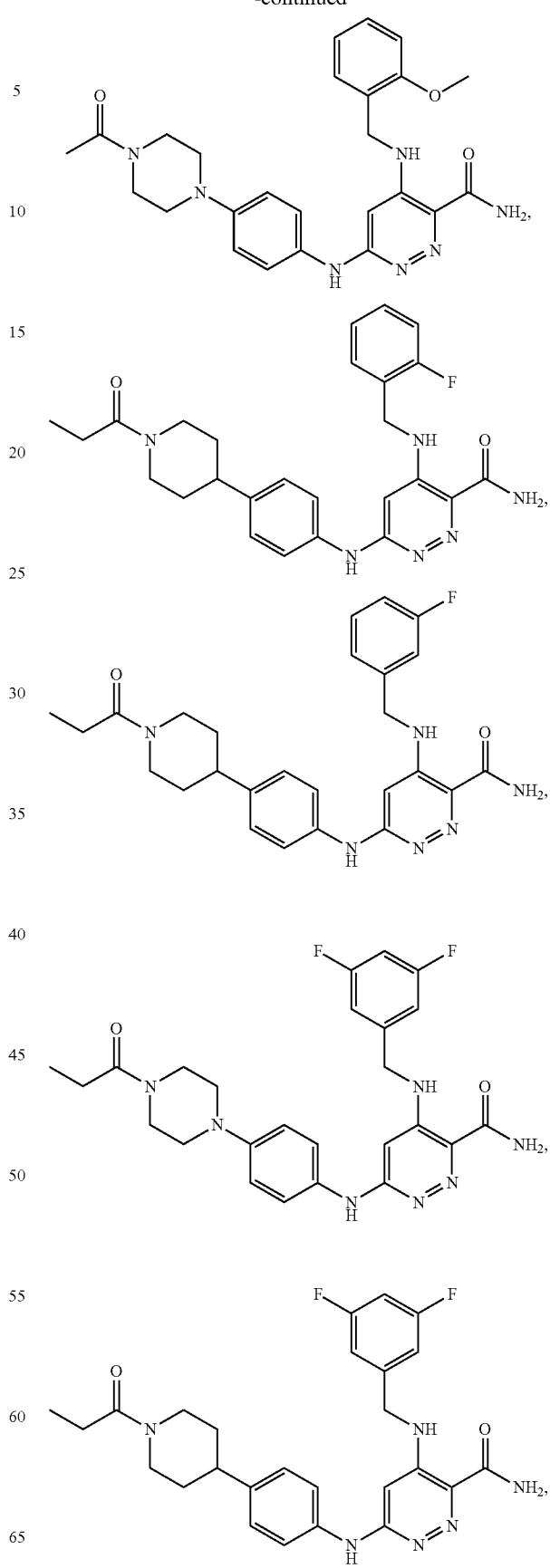

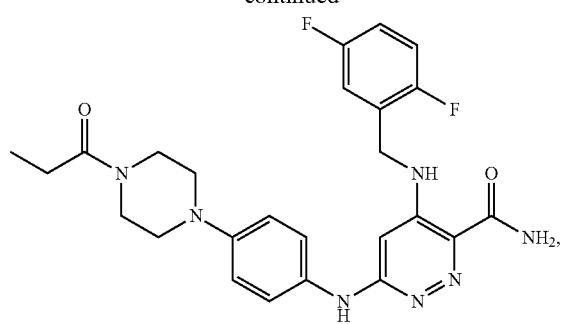
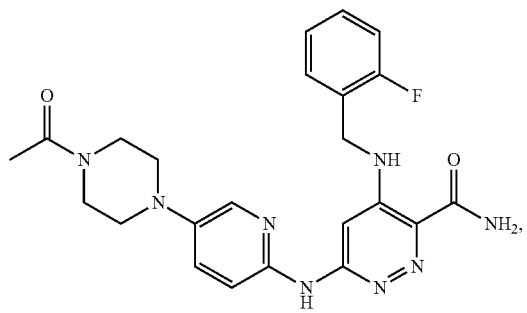
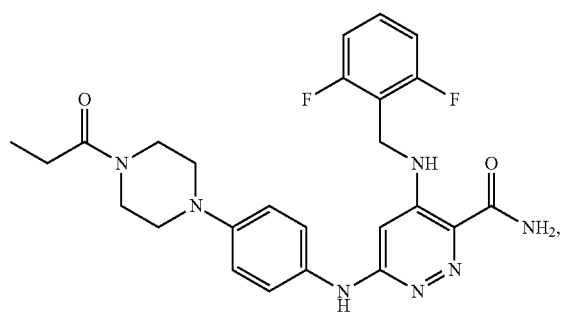
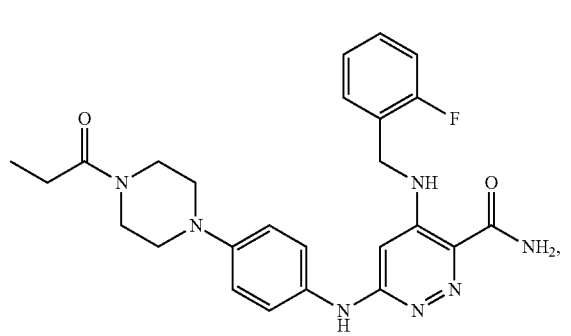
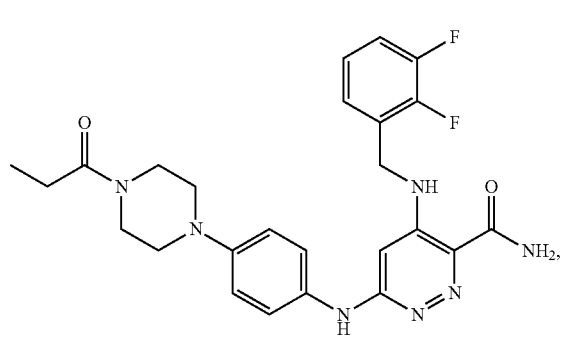
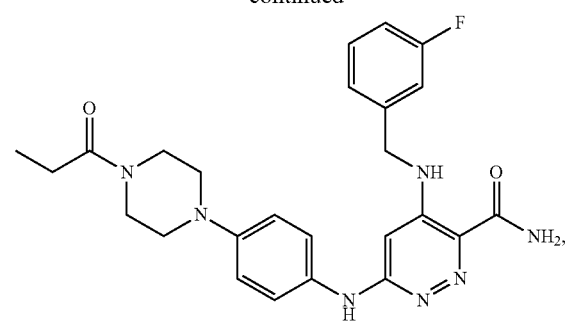
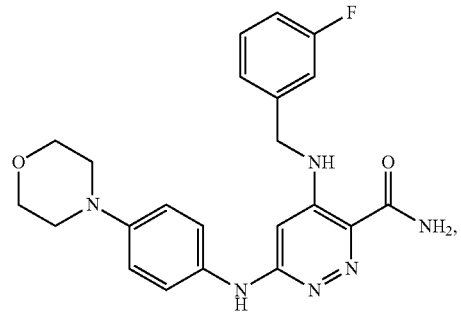
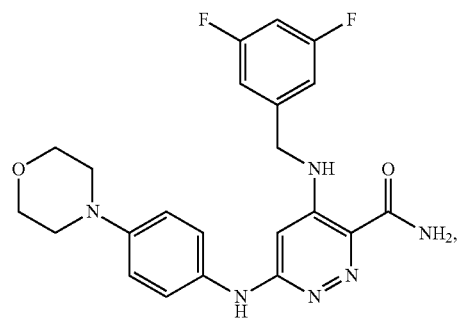
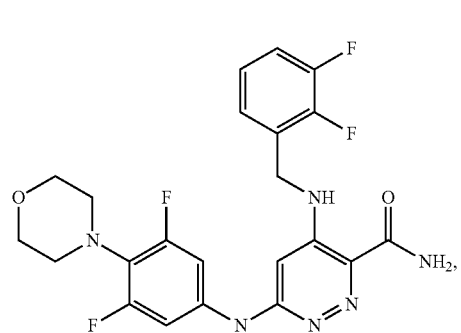
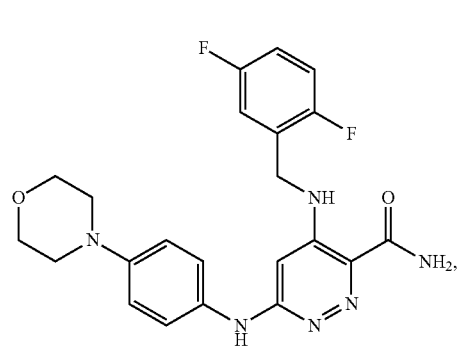

141
-continued
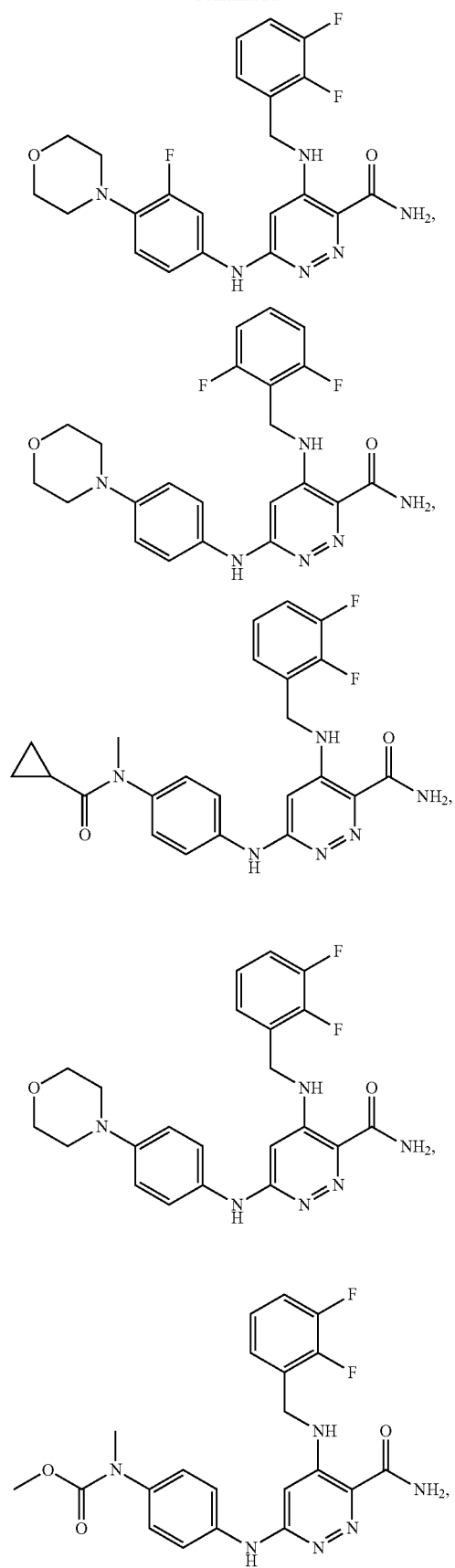
142
-continued
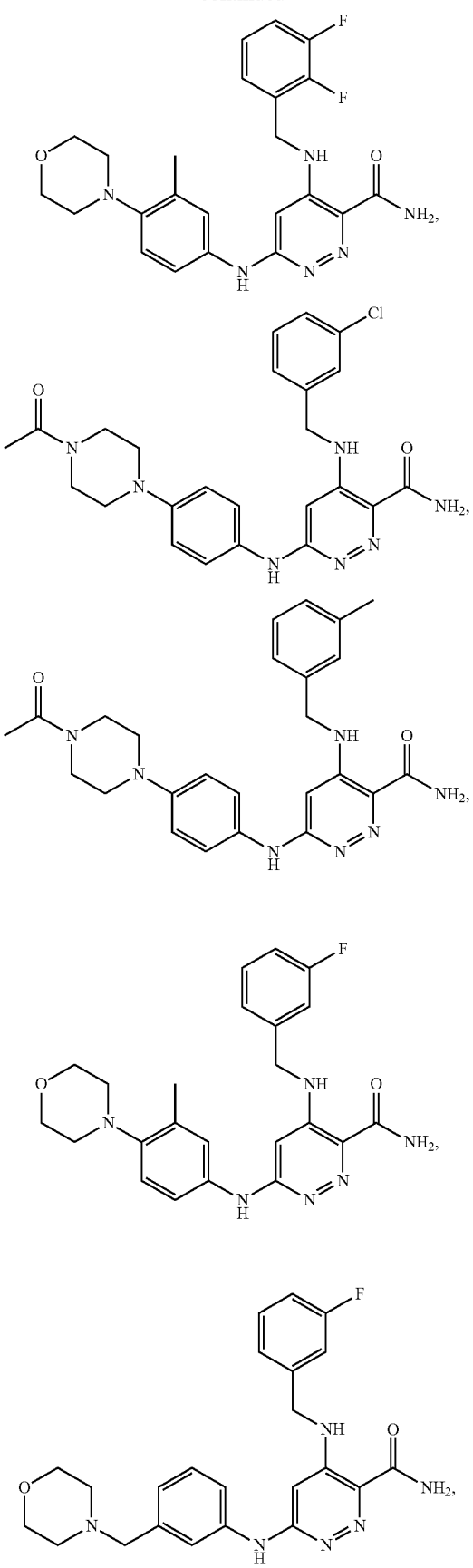

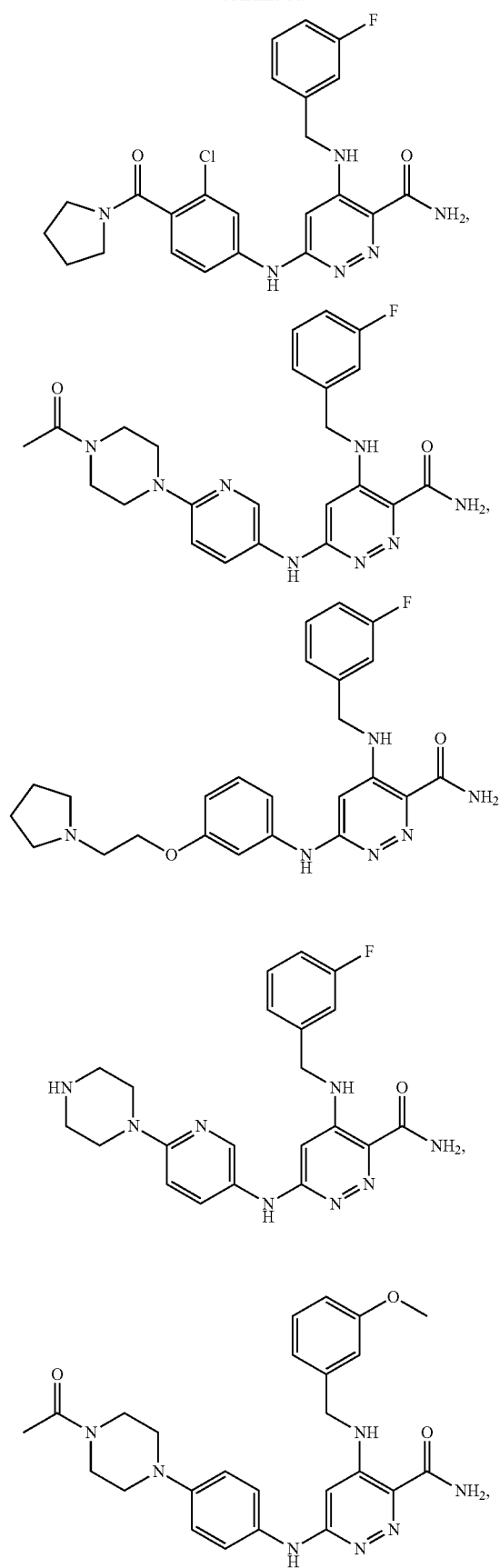
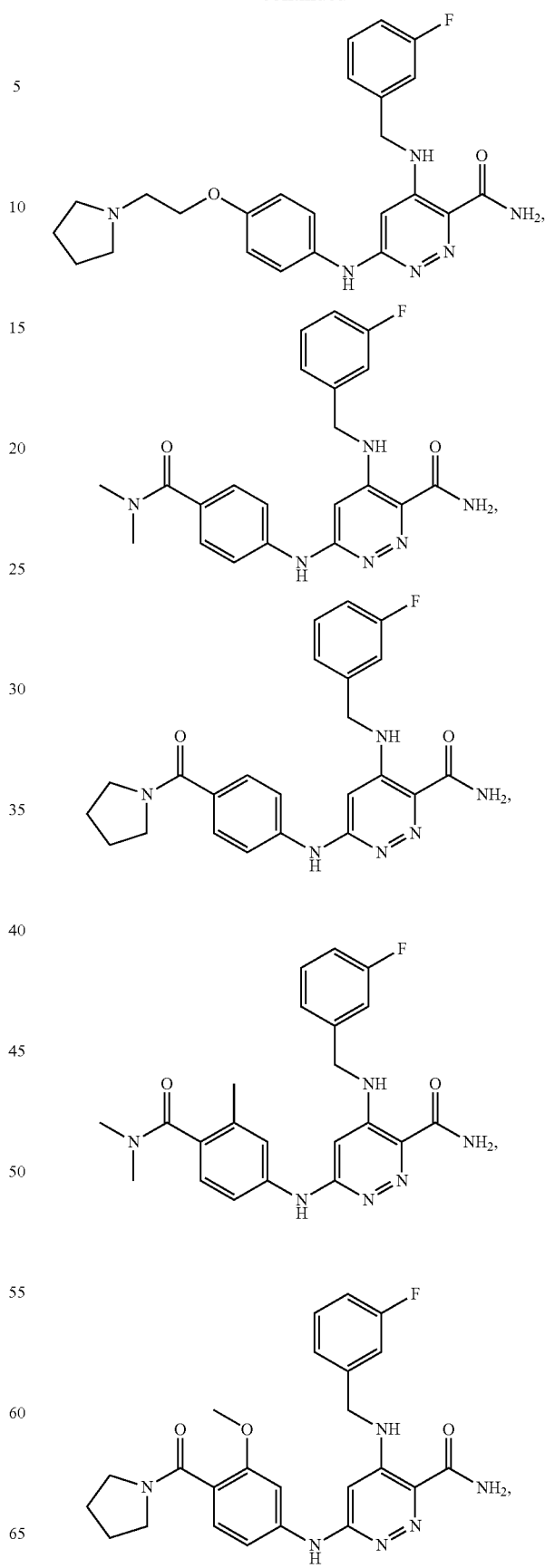

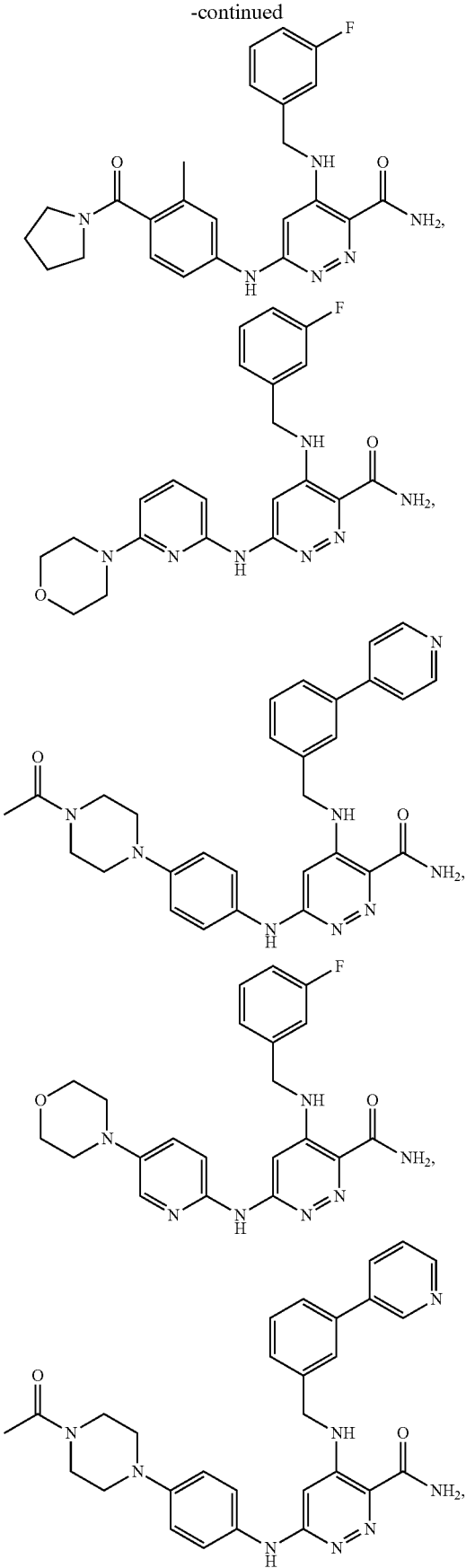
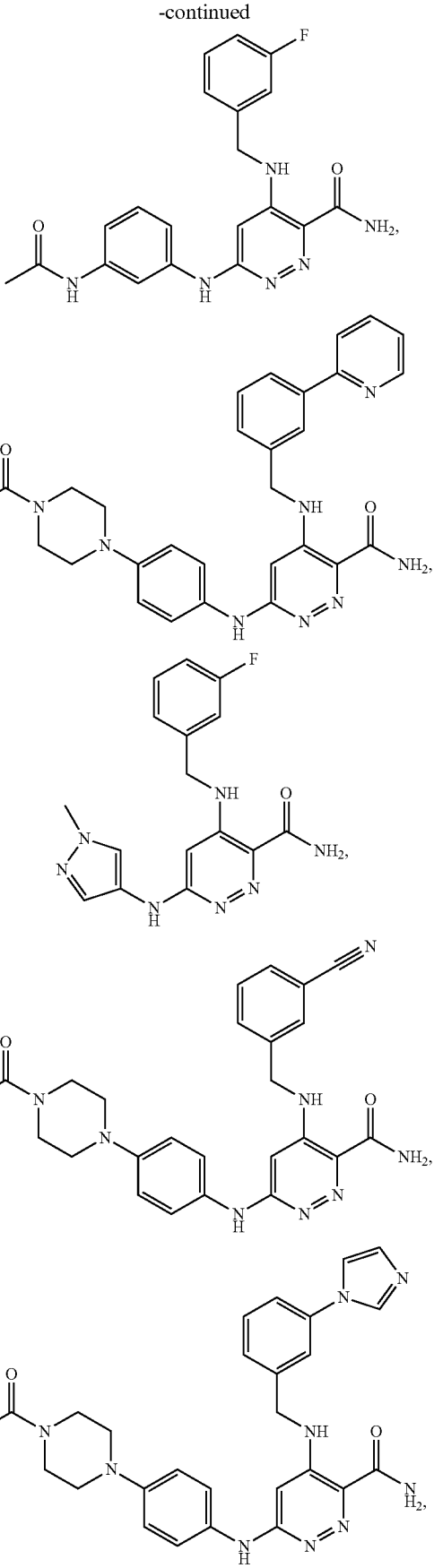

147
-continued
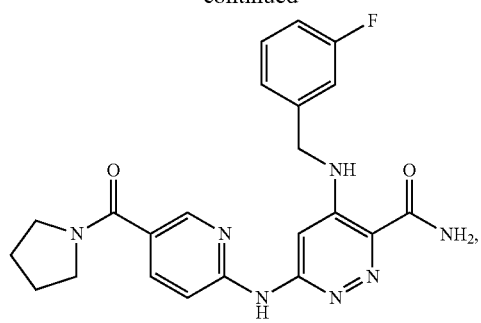
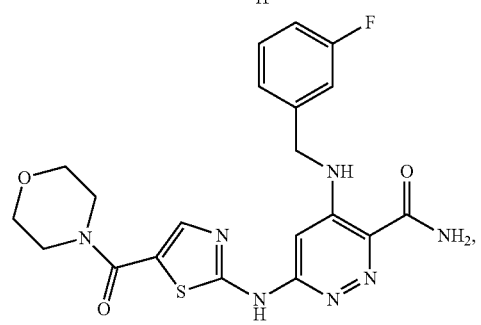
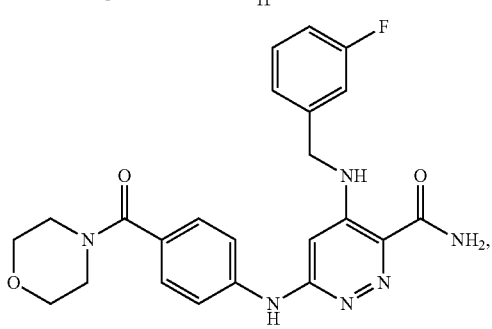
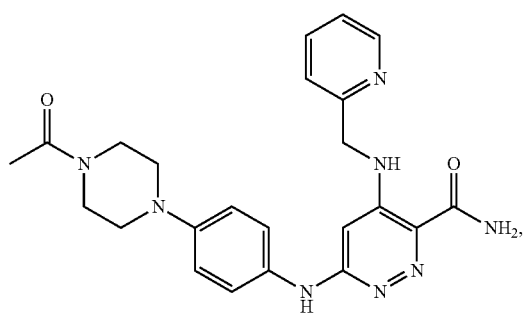
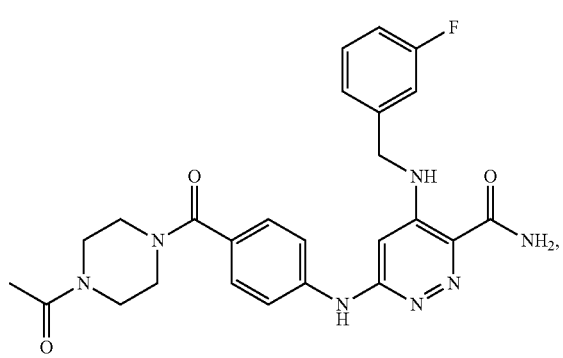
148
-continued
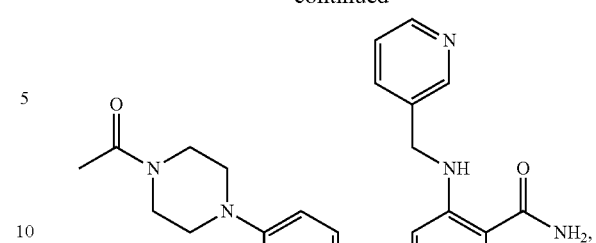
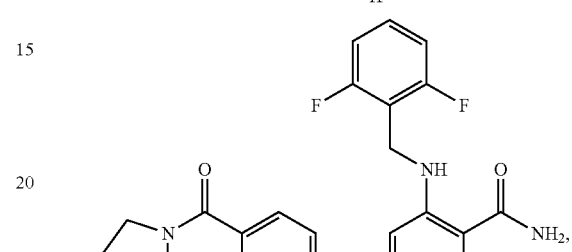
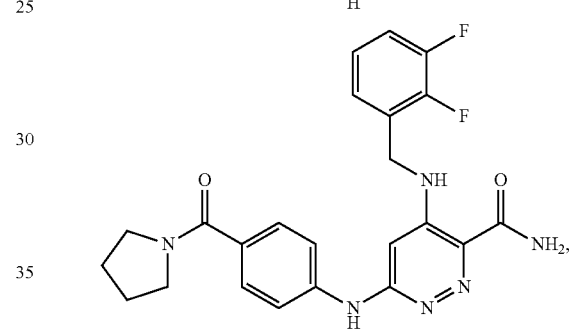
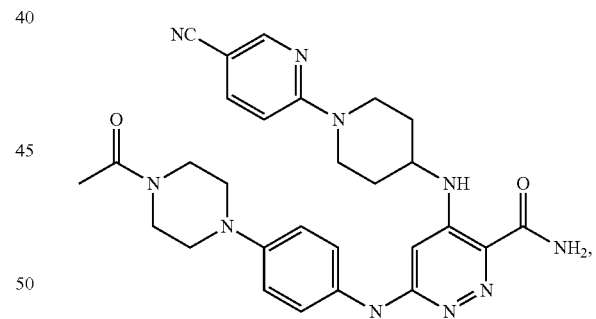
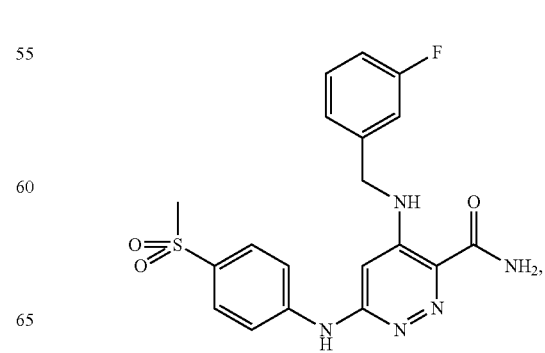

149
-continued
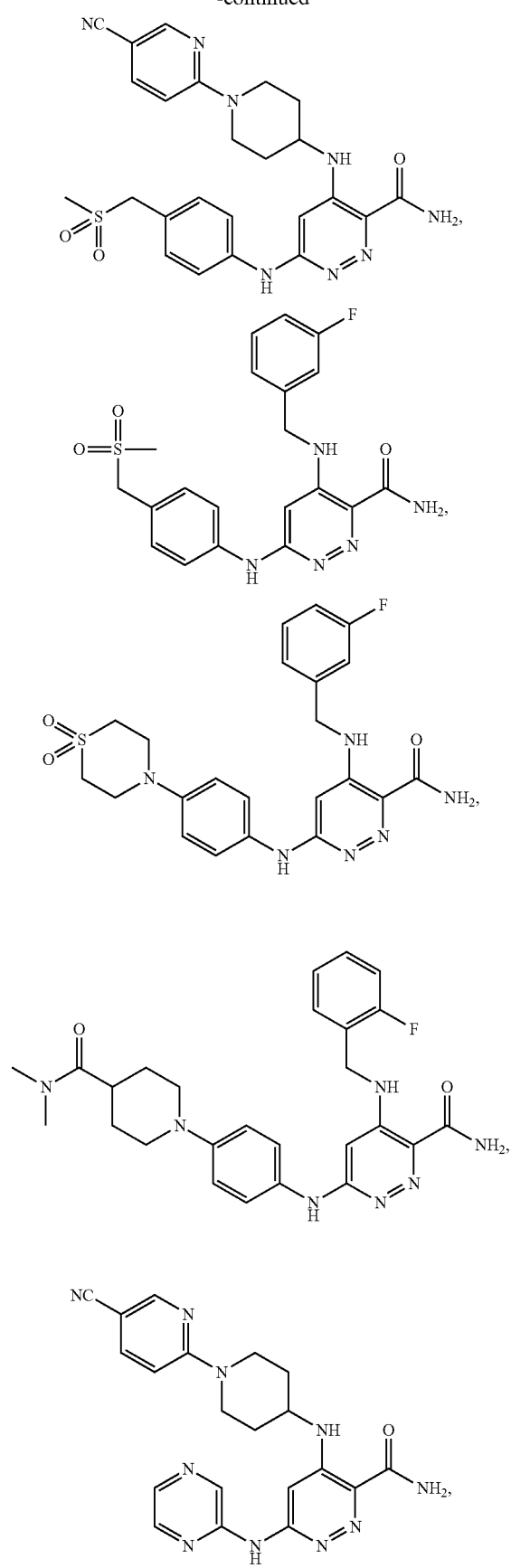
150
-continued
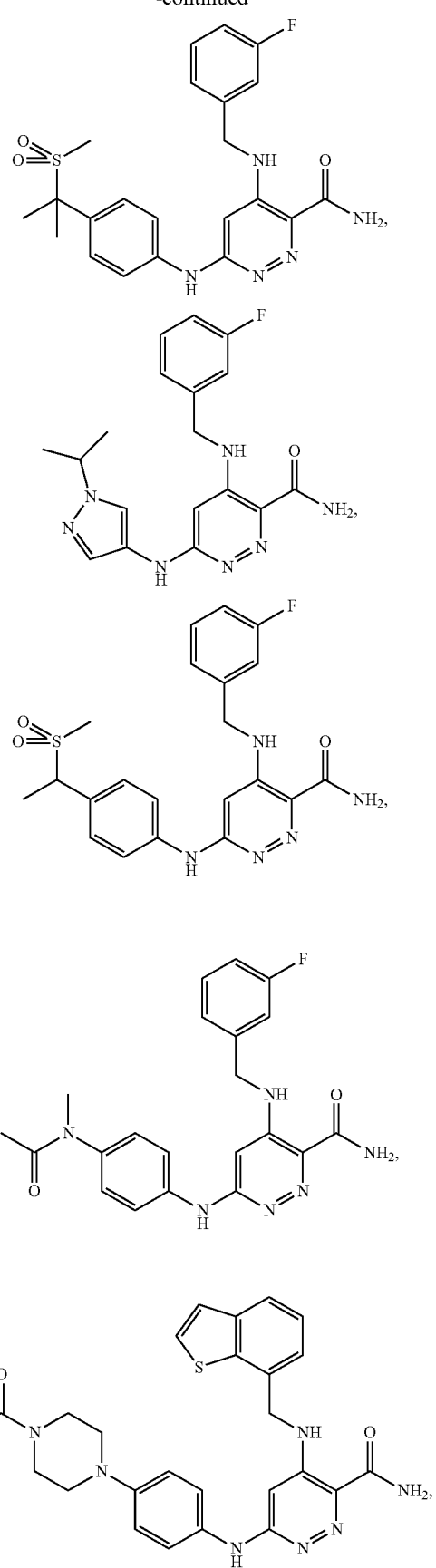

151
-continued
152
-continued
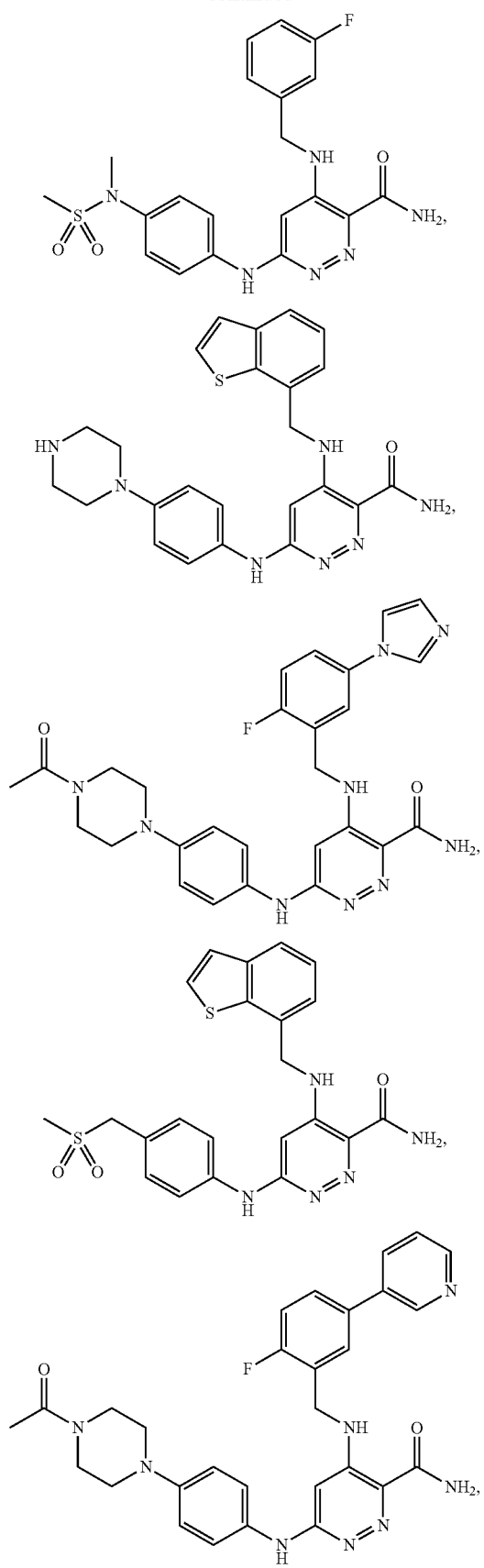
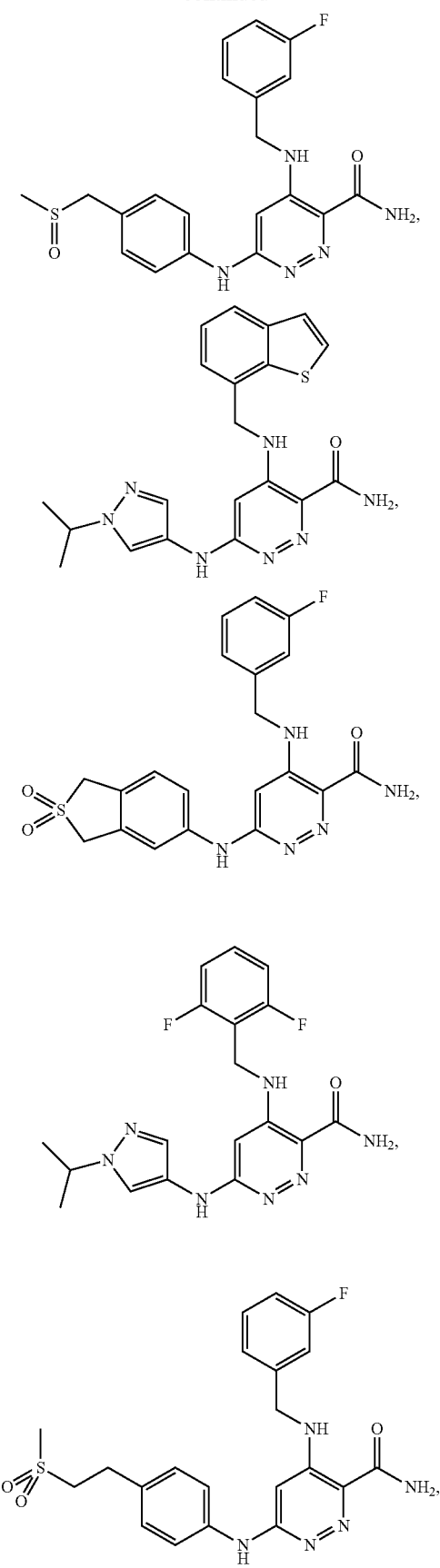

153
-continued
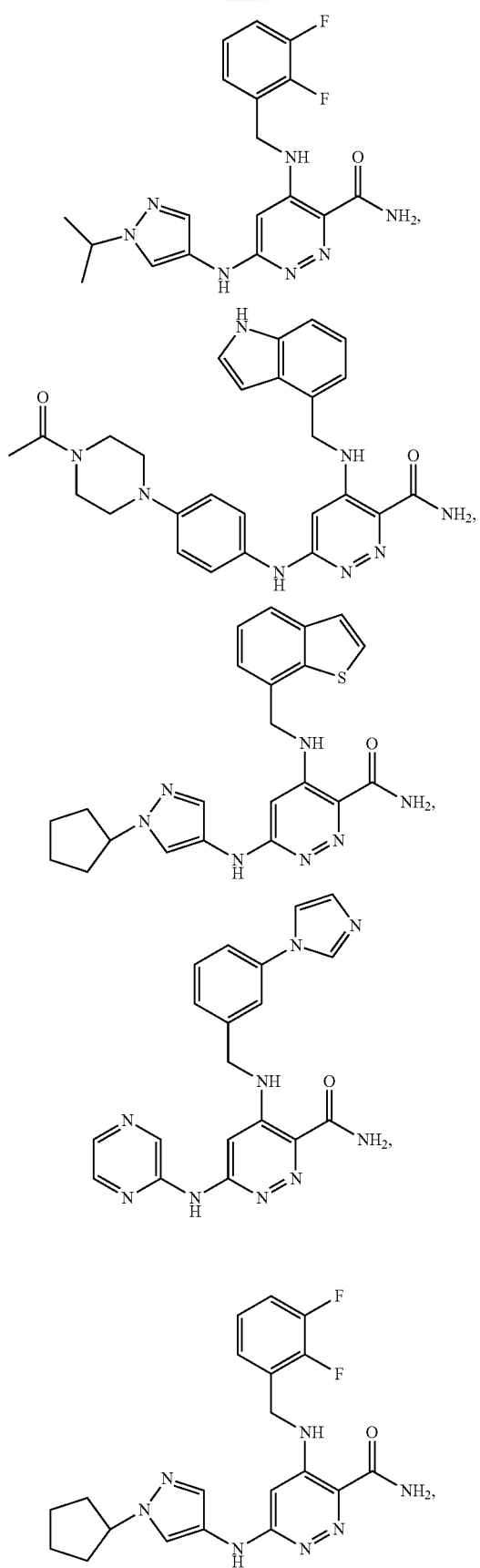
154
-continued
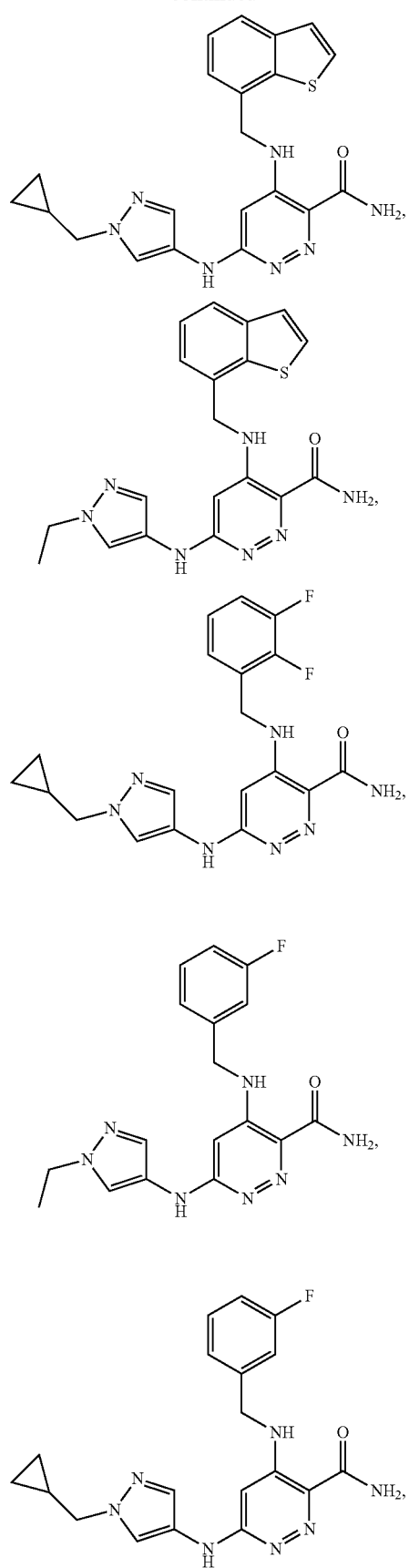

155
-continued
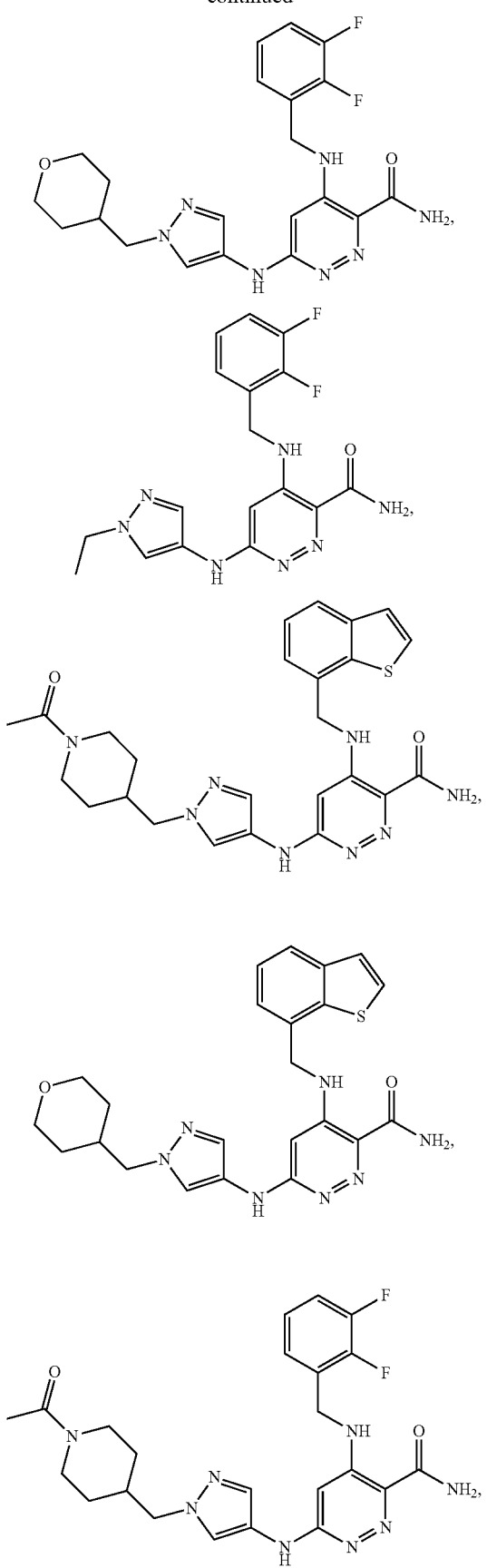
156
-continued
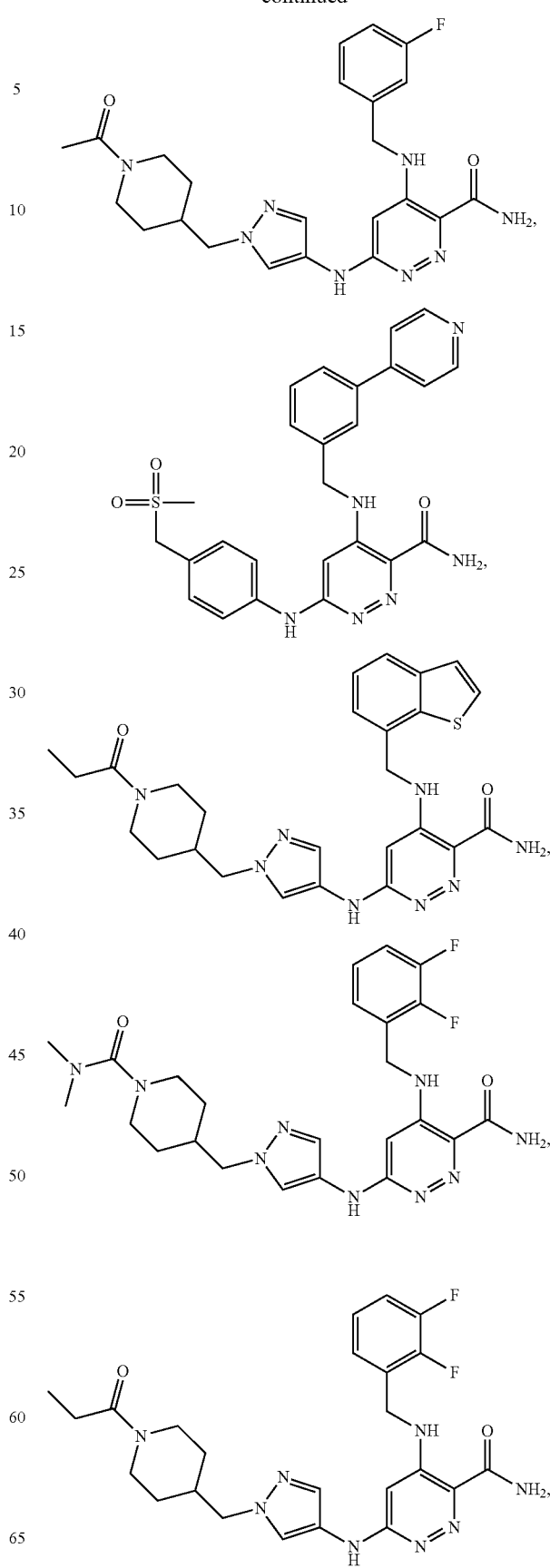

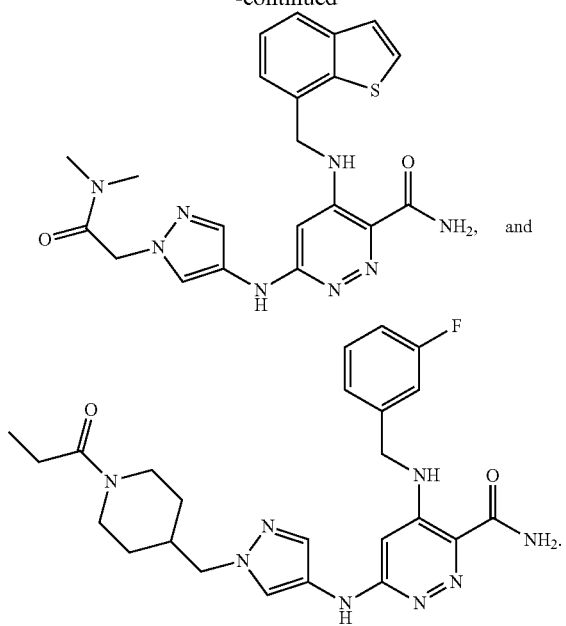
32. The compound of claim 1, or a tautomer thereof or a pharmaceutically acceptable salt or hydrate thereof, which is selected from the group consisting of:
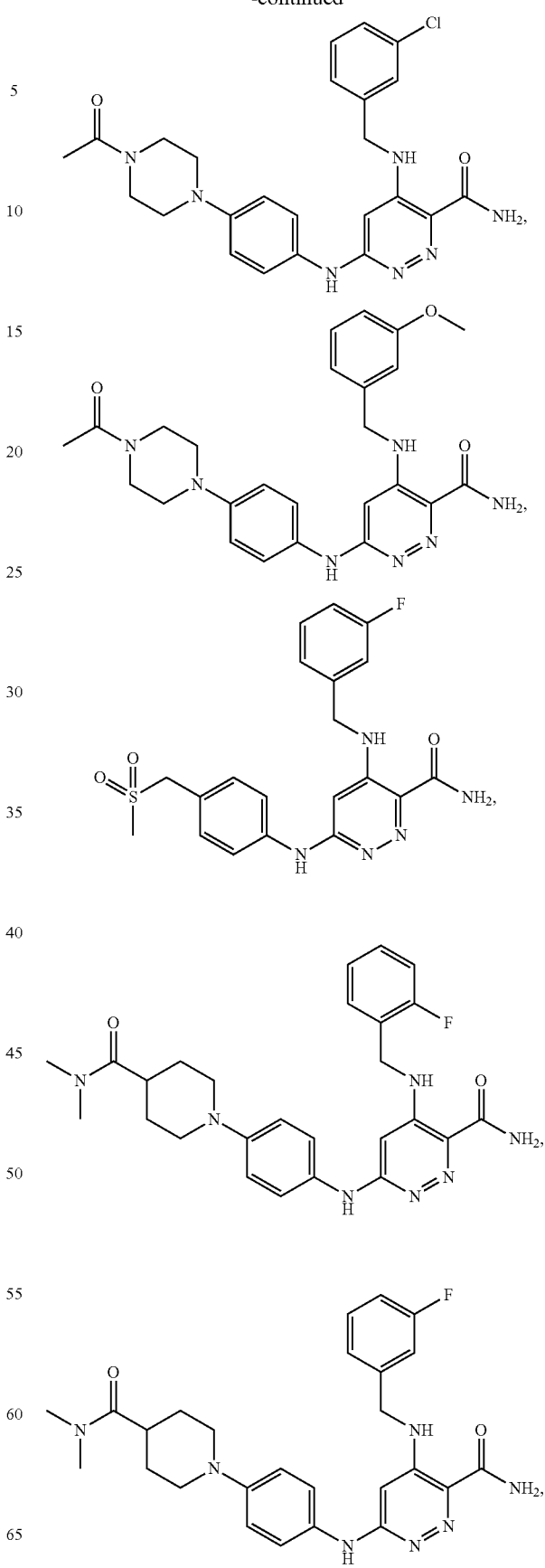

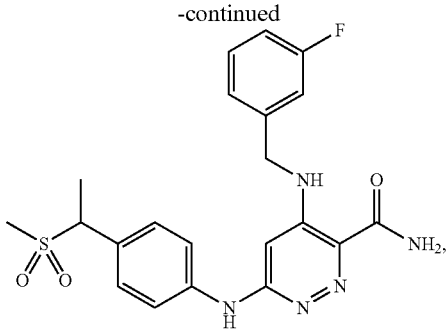

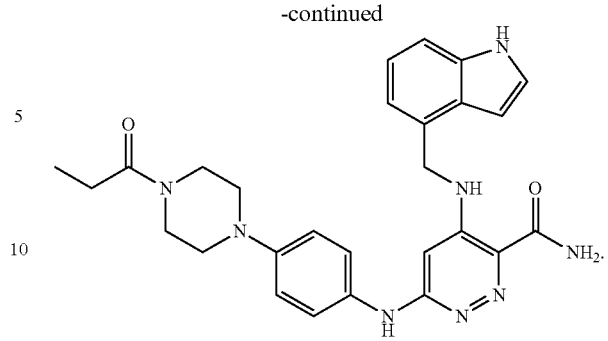

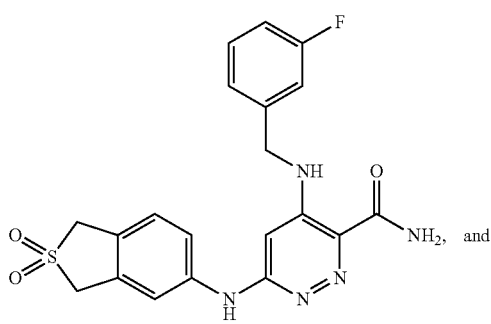

33. A composition comprising a compound of claim 1 in combination with a pharmaceutically acceptable carrier or diluent.

34. A method for treating cancer in a subject comprising the step administering to a subject in need of such treatment a therapeutically effective amount of a compound of claim 1 or claim 31.

35. A method for treating organ transplants, asthma, COPD, systemic lupus erythematosus, multiple sclerosis, rheumatoid arthritis, Crohn's disease, Type I diabetes, or psoriasis in a subject comprising the step of administering to a subject in need of such treatment a therapeutically effective amount of a compound of claim 1 or claim 31.

36. A method for treating sickle cell disease in a subject comprising the step of administering to a subject in need of such treatment a therapeutically effective amount of a compound of claim 1 or claim 31.

37. A kit comprising a composition of claim 33, packing and instruction for use.

38. The method of 36, wherein said sickle cell disease is selected from the group consisting of sickle cell anemia, sickle-hemoglobin C disease, sickle beta-plus thalassemia, and sickle beta-zero thalassemia.

* * * * *